US011505576B2

(12) United States Patent
Ekblad et al.

(10) Patent No.: US 11,505,576 B2
(45) Date of Patent: Nov. 22, 2022

(54) POLYPEPTIDES BASED ON A SCAFFOLD

(71) Applicant: AFFIBODY AB, Solna (SE)

(72) Inventors: Caroline Ekblad, Saltsjö-Boo (SE); Elin Gunneriusson, Saltsjöbaden (SE); Sophia Hober, Stockholm (SE); Sarah Lindbo, Lidingö (SE)

(73) Assignee: AFFIBODY AB, Solna (SE)

( * ) Notice: Subject to any disclaimer, the term of this patent is extended or adjusted under 35 U.S.C. 154(b) by 0 days.

(21) Appl. No.: 16/977,625

(22) PCT Filed: Mar. 12, 2019

(86) PCT No.: PCT/EP2019/056167
§ 371 (c)(1),
(2) Date: Sep. 2, 2020

(87) PCT Pub. No.: WO2019/175176
PCT Pub. Date: Sep. 19, 2019

(65) Prior Publication Data

US 2021/0047372 A1 Feb. 18, 2021

(30) Foreign Application Priority Data

Mar. 13, 2018 (EP) .................................... 18161507

(51) Int. Cl.
*C07K 14/00* (2006.01)
*C07K 1/14* (2006.01)
*C12N 15/10* (2006.01)

(52) U.S. Cl.
CPC ................ *C07K 14/00* (2013.01); *C07K 1/14* (2013.01); *C12N 15/10* (2013.01); *C07K 2319/00* (2013.01)

(58) Field of Classification Search
None
See application file for complete search history.

(56) References Cited

FOREIGN PATENT DOCUMENTS

WO 2013009539 A1 1/2013

OTHER PUBLICATIONS

International Search Report issued in Application No. PCT/EP2019/056167 dated Apr. 15, 2019, 5 pages.
Johan Nilvebrant et al., "The Albumin-Binding Domain as a Scaffold for Protein Engineering", Computational and Structural Biotechnology Journal, vol. 6, Issue 7, Mar. 2013, 8 pages.
Stefan Stahl et al., "Affibody Molecules in Biotechnological and Medical Applications", CelPress, Trends in Biotechnology, vol. 35, No. 8, Aug. 2017, 22 pages.
Written Opinion issued in Application No. PCT/EP2019/056167 dated Apr. 15, 2019, 6 pages.
International Preliminary Report on Patentability issued in Application No. PCT/EP2019/056167 dated Sep. 15, 2020, 7 pages.

*Primary Examiner* — Thomas S Heard
(74) *Attorney, Agent, or Firm* — Cantor Colburn LLP

(57) ABSTRACT

The disclosure provides a population of polypeptide variants based on a common scaffold, each polypeptide in the population comprising the scaffold amino acid sequence $X_{sc1}$AELD$X_{sc2}X_{sc3}$GVG AXXIKXIX$_{sc4}$XA XXVEXVQXXK QXILAX. The disclosure also provides methods for selecting and identifying polypeptides from the population, as well as such polypeptides themselves.

18 Claims, 8 Drawing Sheets

Specification includes a Sequence Listing.

Figure 1A-B
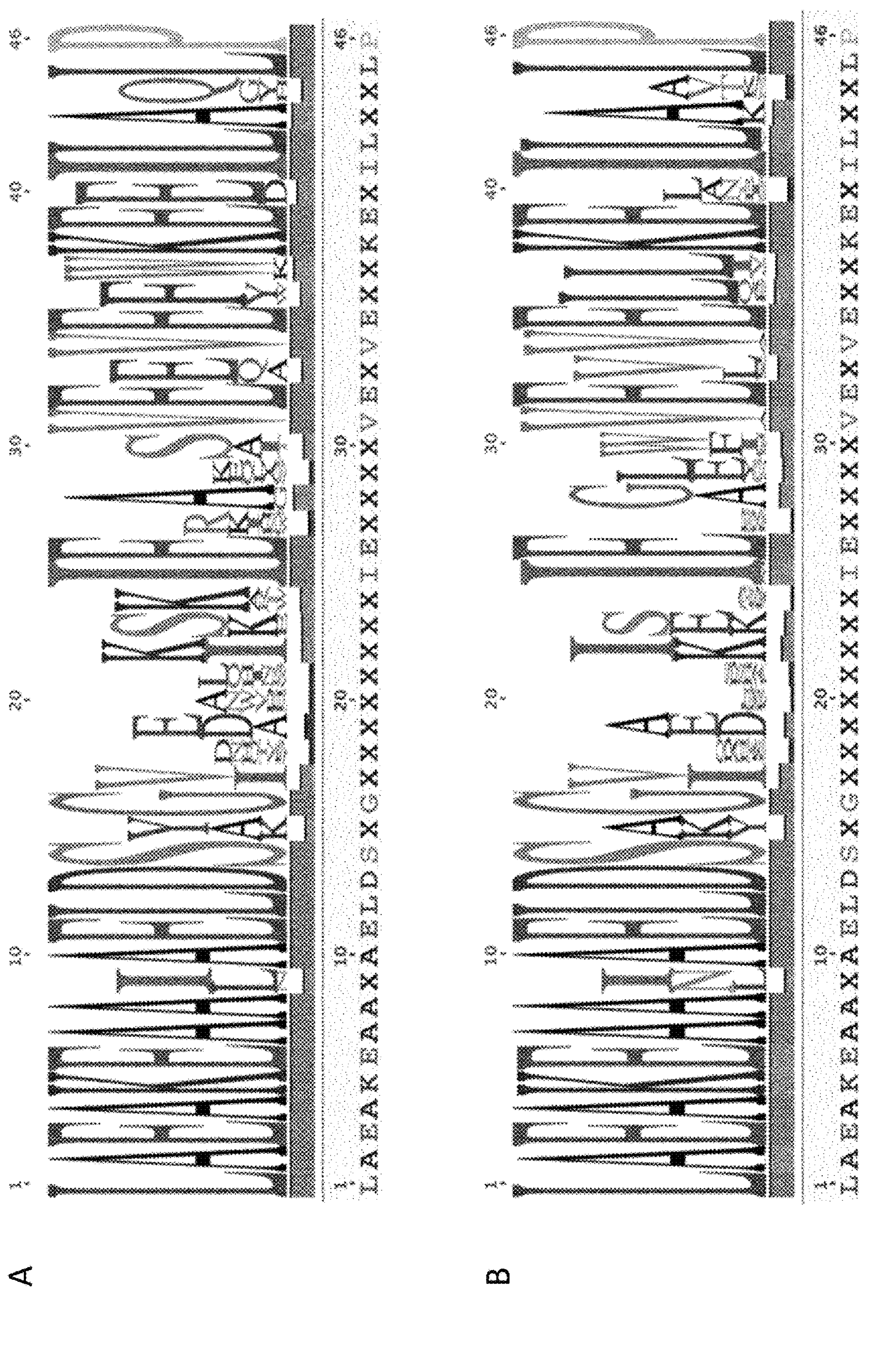

Figure 1C-D
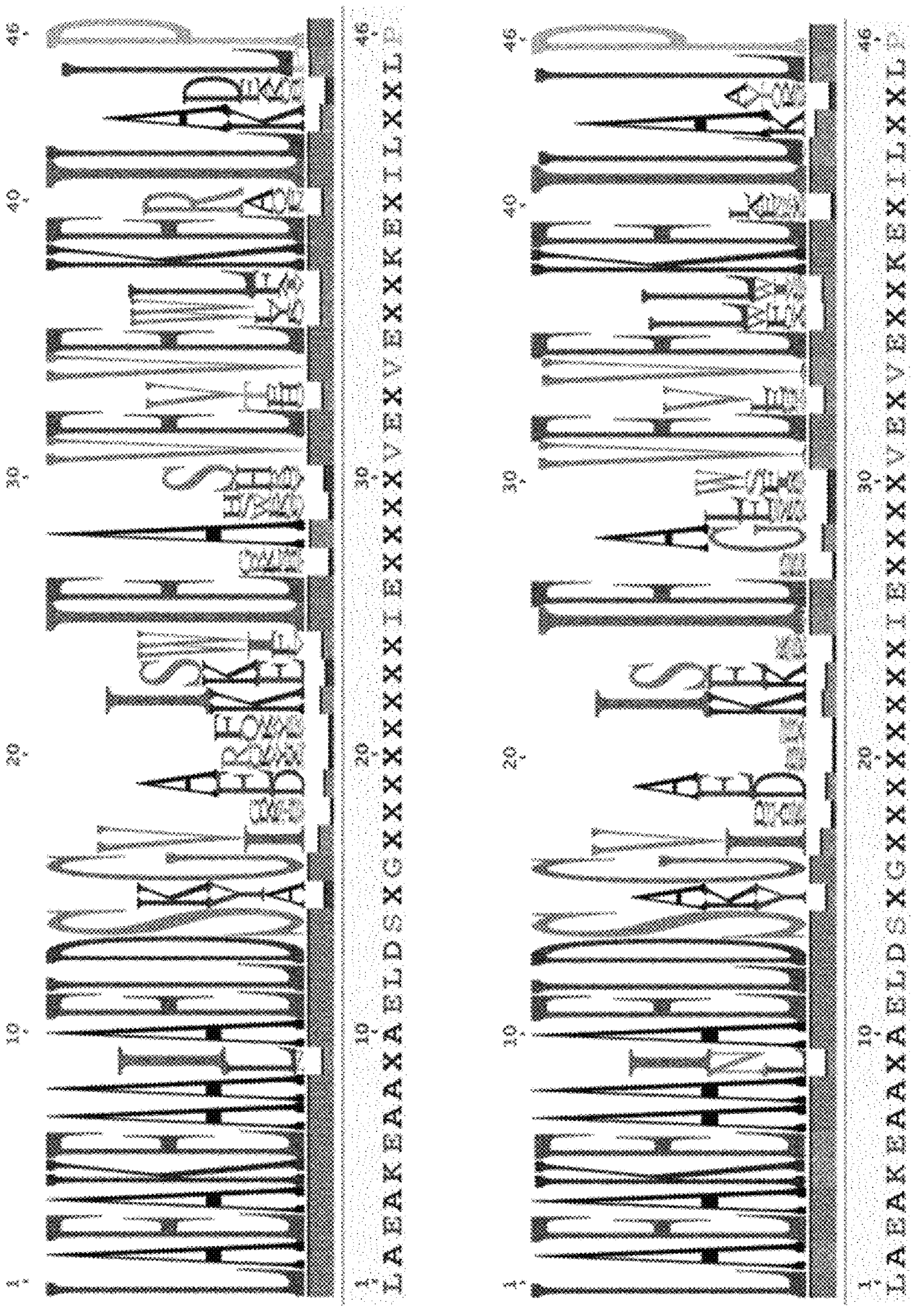
C
D

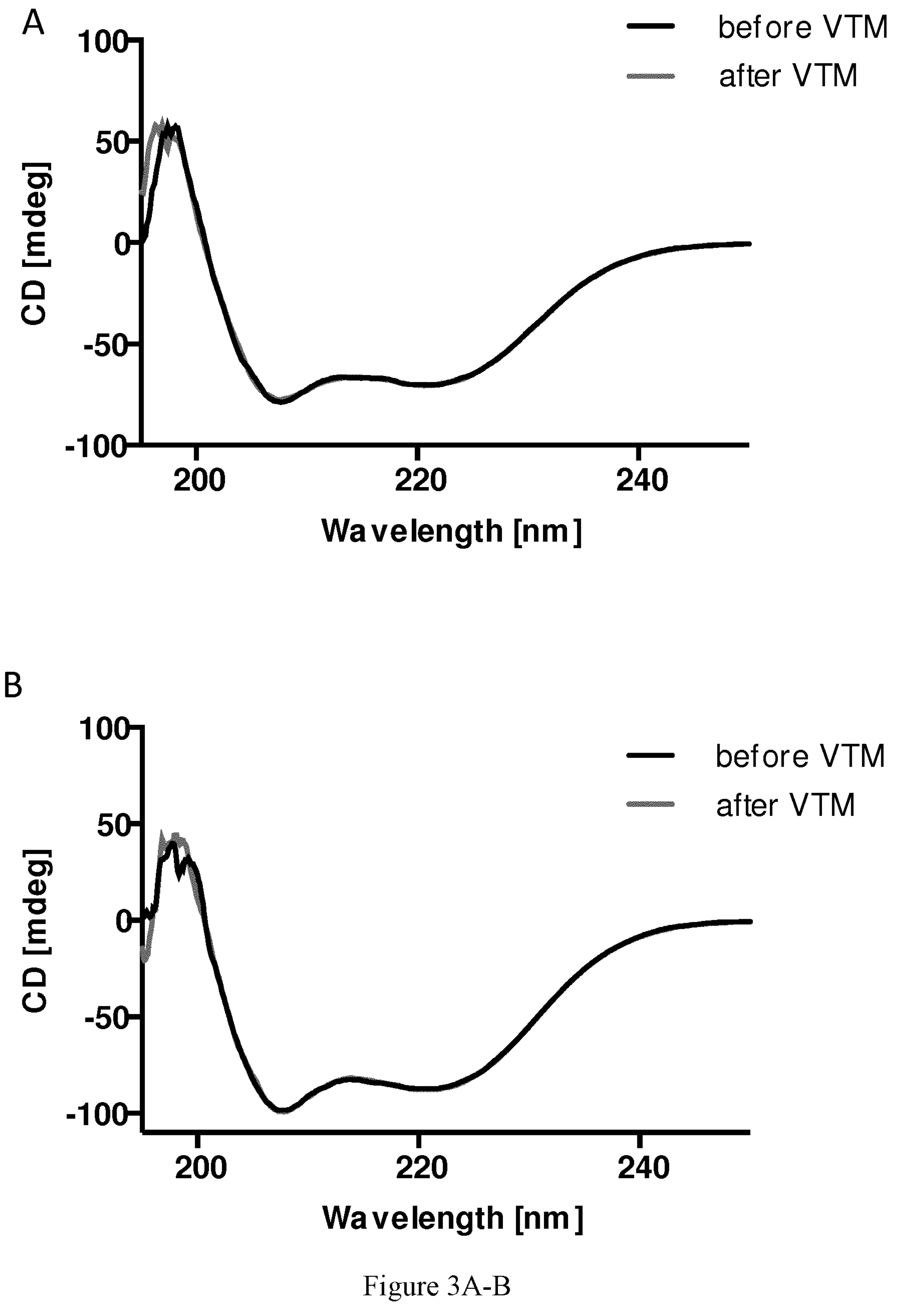
Figure 3A-B

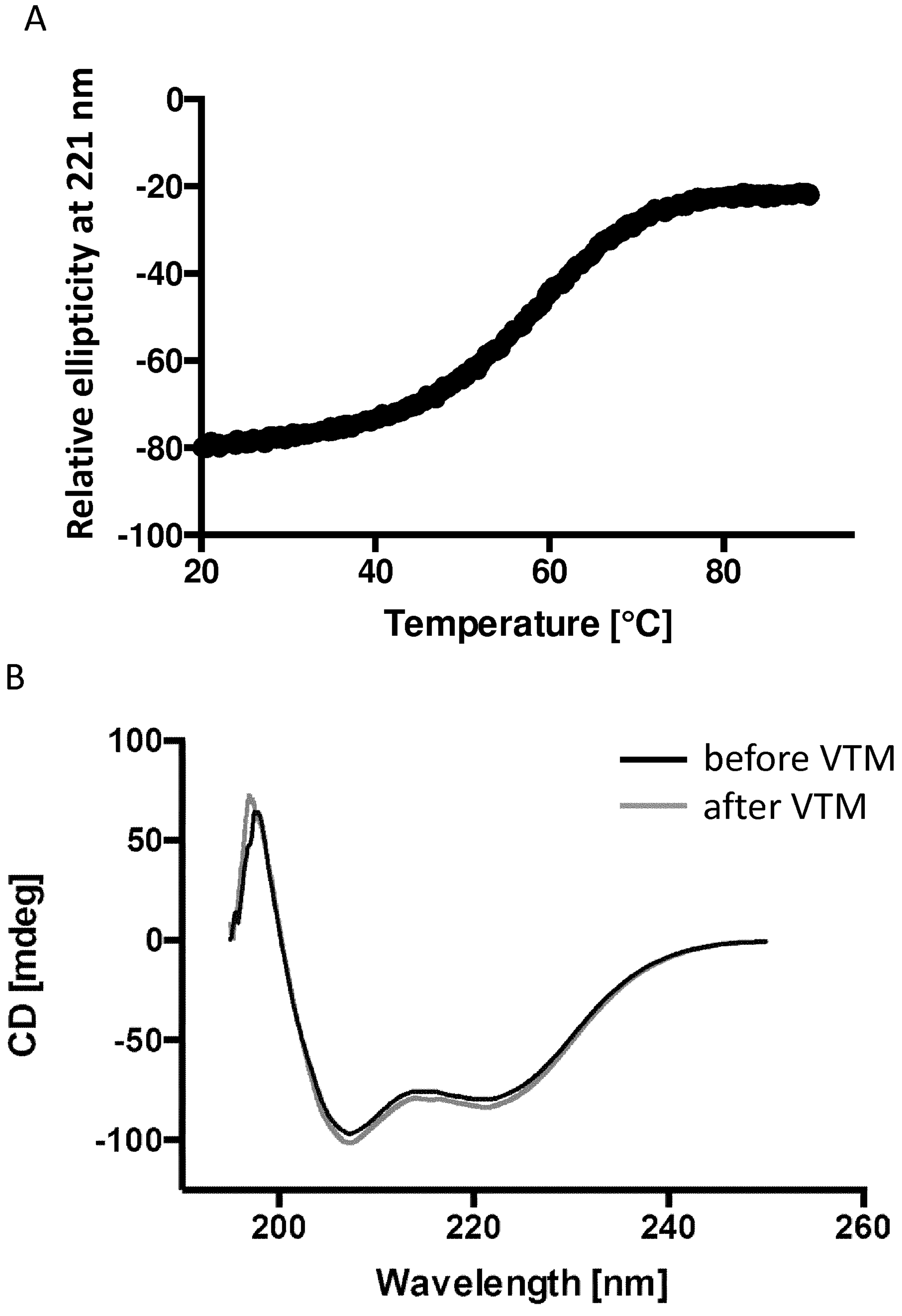
Figure 4A-B

C
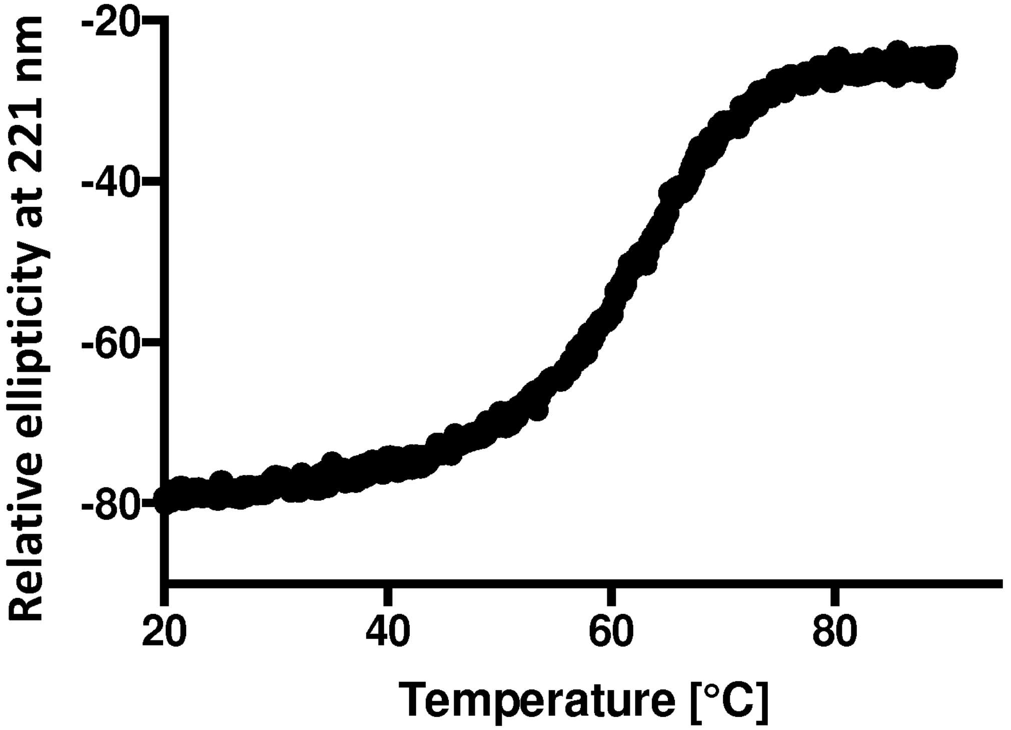
D
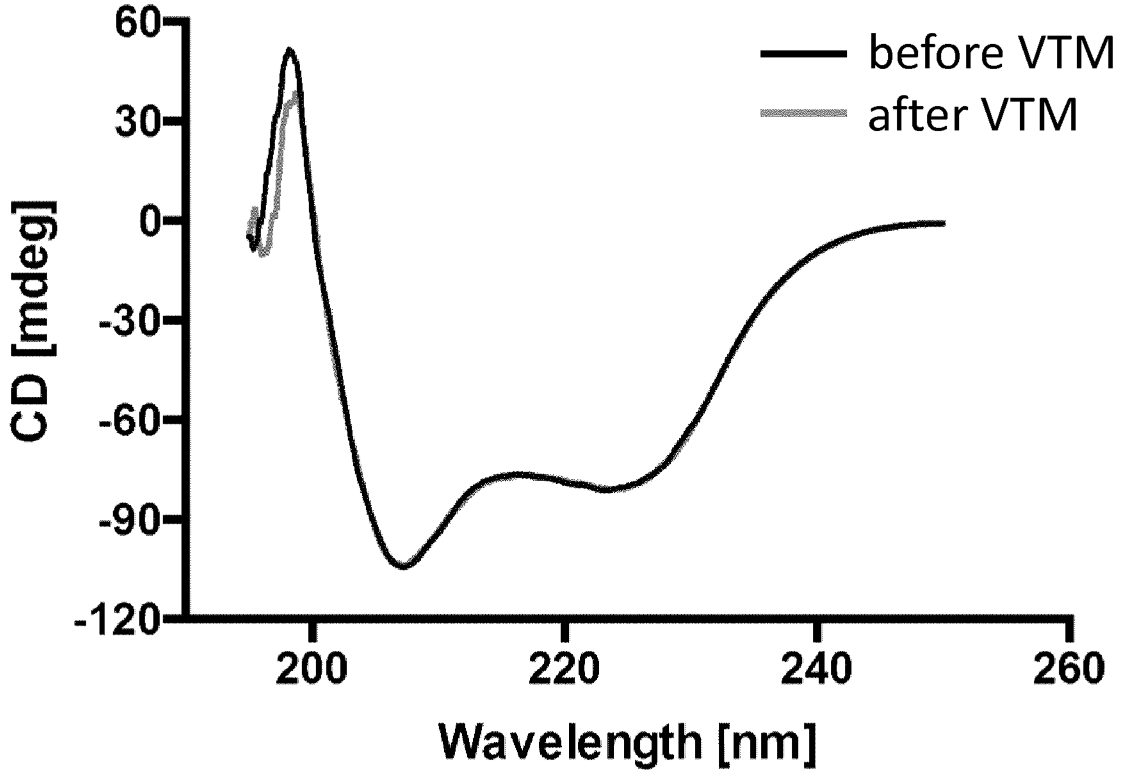
Figure 4C-D

E
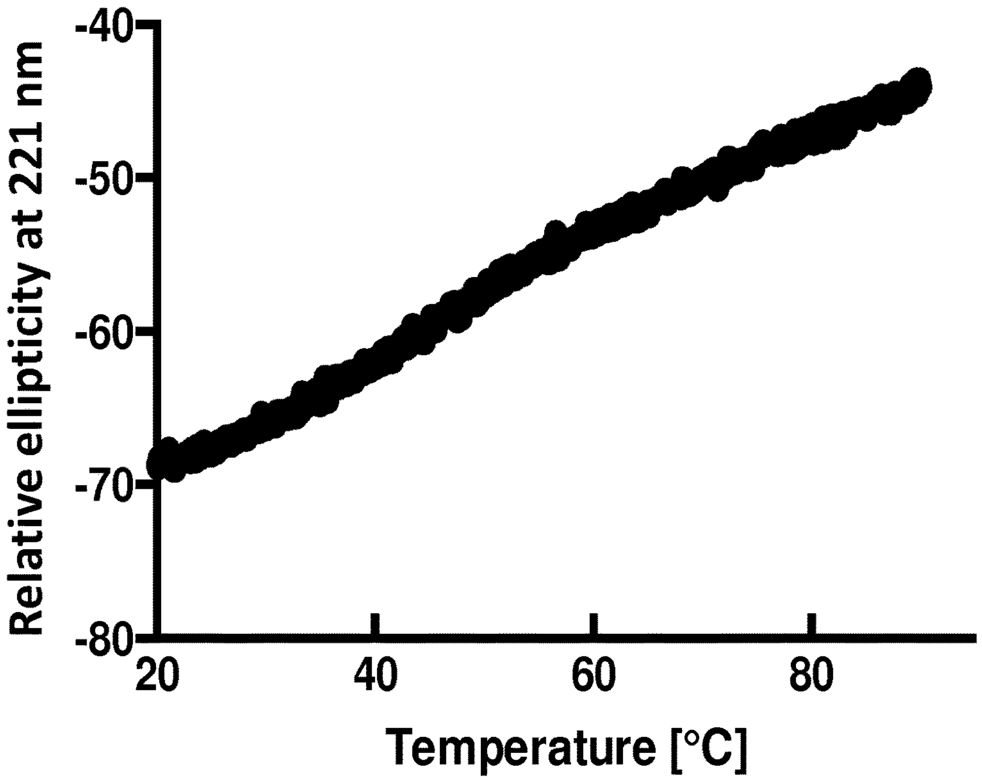
F
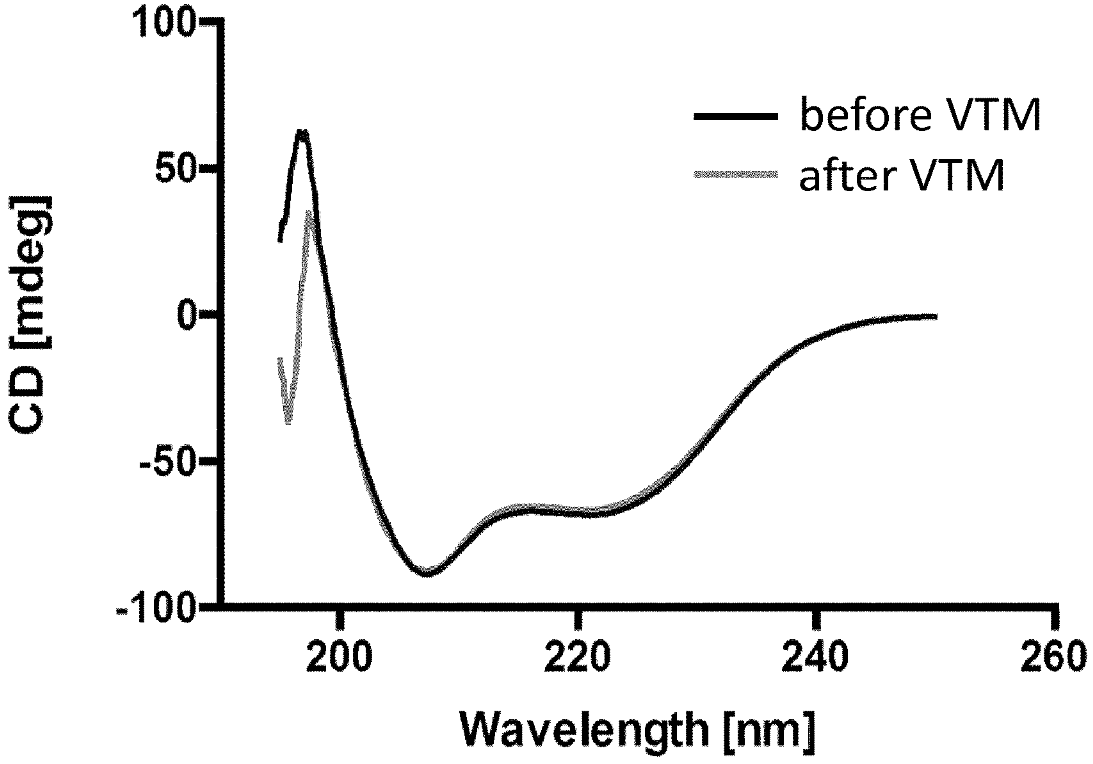
Figure 4E-F

POLYPEPTIDES BASED ON A SCAFFOLD

CROSS-REFERENCE TO RELATED APPLICATIONS

This Application is a U.S. National Stage Application of PCT/EP2019/056167 filed Mar. 12, 2019 which claims priority to European Patent Application No. 18161507.1 filed Mar. 13, 2018, both of which re incorporated by reference in their entirety.

FIELD OF THE DISCLOSURE

The present disclosure is directed to novel populations of polypeptide variants based on a common scaffold sequence. These populations can for example be used as a source of novel binding polypeptides for use in therapeutic, diagnostic or biotechnological applications.

BACKGROUND

Scaffold Proteins

The increasing knowledge of the molecular pathologies of diseases, including cancer, infections, immunological and inflammatory disorders, paves the way for development of molecules with desired specificities that more efficiently can inhibit or bind the intended molecule while reducing off-target side effects. Antibodies have been the most widely used affinity ligand both in medicine and biotechnology research, but suffer from disadvantages related to their large size and composition. The stability and function of the complex multi-chain antibodies are dependent on correct disulfide bond formations and glycosylation patterns, requiring expensive manufacturing in eukaryotic expression systems. Thus, the use of antibody fragments as well as development of non-antibody based scaffolds has emerged as an attractive alternative. Some of the more advanced protein scaffolds that have been used successfully for the generation of high-affinity ligands against numerous targets include the fibronectin (type III) domain, the Kunitz domain, the SH3 domain, the Z domain of staphylococcal Protein A, ankyrin repeats and lipocalin. Candidate polypeptides based on these scaffolds have progressed into clinical studies, and the first molecule based on a non-antibody scaffold to be granted regulatory approval was the Kunitz domain DX-88 (ecallantide) for the treatment of hereditary angioedema (reviewed in Vazquez-Lombardi et al, Drug Discov Today, 2015, 20(10):1271-83).

Advantages of these relatively small scaffold proteins include a high stability and high production yields in prokaryotic expression systems. Their robust framework allows certain surface regions to be modulated to introduce novel binding functions without compromising the original fold of the scaffold. On the other hand, the small size implicates a short serum half-life due to renal clearance, and use of half-life extension technology may be required for therapeutic applications (Gebauer and Skerra (2009) Curr Opin Chem Biol 13(3):245-55).

A powerful tool to generate novel ligands based on a certain scaffold is combinatorial protein engineering. Here, complex libraries are designed, constructed and subsequently screened to identify ligands with desired properties. Challenges in creating a versatile protein library containing a large number of diverse ligands with retained folding and solubility include selecting a suitable protein or protein domain as starting point, which positions to randomize, what degree of randomization to use, which amino acids to allow in randomized positions, as well as which amino acids to select in fixed positions.

Engineered GA3 Domain Variants

The ~5 kDa GA3 domain of streptococcal protein G (SpG) strain G148 (G148-GA3; SEQ ID NO:158) has been engineered to either improve its affinity for its natural target albumin, or to introduce a novel binding specificity. The structure of G148-GA3 has been determined, showing a three-helix bundle fold, and a 46 amino acid motif within the GA3 domain was defined as ABD (albumin binding domain) (Kraulis et al, FEBS Lett 378:190, 1996; Johansson et al, J. Biol. Chem. 277:8114-20, 2002). The albumin binding residues within ABD have been located to the region extending from position 18 to position 44, which mainly include helices two and three and their connecting loop (Lejon et al, J Biol Chem., 2004, 279(41):42924-8).

Rozak et al reported the creation of artificial variants of G148-GA3, which were selected and studied with regard to different species specificity and stability (Rozak et al, Biochemistry, 2006, 45:3263-3271), whereas Jonsson et al developed artificial variants of G148-GA3 having a very much improved affinity for human serum albumin (Jonsson et al, Prot Eng Des Sel, 2008, 21:515-27; WO2009/016043). Jacobs et al designed non-natural albumin binding variants based on consensus sequence methods using the G148-GA3 as template. The resulting variants were reported to exhibit high thermal stability and high affinity for albumin from different species (Jacobs et al, Protein Eng Des Sel., 2015, 28(10):385-93; WO2013/177398).

A few T- and B-cell epitopes have been experimentally identified within the albumin binding region of SpG strain G148 (Goetsch et al, Clin Diagn Lab Immunol, 2003, 10:125-32), making the G148-GA3 as such less suitable for use in pharmaceutical compositions for human administration. To reduce the immune stimulatory properties, new ABD variants with fewer potential B- and T-cell epitopes, but with retained high albumin binding capacity, were developed as described for example in WO2012/004384.

The use of G148-GA3 as a scaffold in developing molecules with novel specificities has been reported by the group of Maly et al. They randomized 11 positions, known to be involved in albumin binding, in the region of amino acids 20-44 of ABD, and selected new ligands targeting interferon gamma (Ahmad et al, Proteins, 2012, 80(3):774-89; WO2014/079399), interleukin 23 (IL-23) receptor (Kuchař et al, Proteins, 2014 82(6):975-89) and p19 of IL-23 (Křížová et al, Autoimmunity, 2017, 50(2):102-113) by ribosome display.

G148-GA3 has also been used as framework for development of ligands with dual specificity. By varying positions mainly located in helix one and three while preserving essential albumin-binding residues in helix two, ligands with a novel specificity and retained (but non-simultaneous) albumin binding capacity were generated (Nilvebrant and Hober, Comput Struct Biotechnol J, 2013, 6:e201303009; WO2014/076177 and WO2014/076179).

Structural Stability

One of the key factors for the success for peptide and protein pharmaceuticals is the stability of the peptide or protein. Proteins showing a high structural stability will most likely withstand chemical modifications and proteolysis with retained function, both during production as well as within the human body. Moreover, stability will influence the active shelf-life of the peptide or protein pharmaceuticals as well as the active life of the peptide or protein pharmaceutical within the human body.

Solubility

For most applications, it is desirable that peptides and proteins are highly soluble and show a low tendency to aggregate. Such characteristics are especially important for protein and peptide pharmaceuticals. There is a strong positive correlation between protein surface hydrophobicity on the one hand and a low solubility and increased tendency to aggregate on the other.

Different scaffolds may have different abilities to interact with target surfaces, depending on the topology and properties of the amino acids at the desired binding epitope of the target molecule. Stability and the propensity for immunogenicity varies between different scaffolds as well as within the same scaffold family, as these properties partly depend on the amino acid sequence at the binding interface. Such differentiation may further implicate that certain scaffold types are particularly suited for certain applications. Against this background, there is a continuing need for the development of novel scaffolds that for example can form the basis for new, efficient and safe modes of treatment and diagnostics.

DESCRIPTION OF THE DISCLOSURE

It is an object of the disclosure to provide a population of polypeptide variants based on a common, novel scaffold.

The novel scaffold exhibits advantages compared to known scaffolds. By extension, the advantages also apply to individual variant polypeptides based on the novel scaffold and selected from the population disclosed herein. These advantages will be discussed in more detail below, but some examples are a small size; a monomeric structure; a high folding stability; the potential to incorporate a unique cysteine residue; and the lack of posttranslational modifications upon expression in a prokaryotic host cell.

Another object of the disclosure is to provide a population of polynucleotides encoding the disclosed polypeptide variant population.

Another object of the disclosure is to provide a combination of a polypeptide population and a polynucleotide population.

A further object of the disclosure is to provide a method for selecting and/or identifying a desired polypeptide, having affinity for a predetermined target, from a population of polypeptides. A related object is to provide a method for production of such a desired polypeptide with affinity for a predetermined target.

Another object is to provide a method for isolating a polynucleotide which encodes a desired polypeptide with affinity for a predetermined target.

It is a further object of the disclosure to provide a polypeptide with a novel scaffold, which polypeptide alleviates the above-mentioned and other drawbacks of currently available antibodies, antibody fragments and alternative non-antibody scaffold polypeptides.

Another object is to provide a method for production of such a polypeptide based on a novel scaffold.

The disclosed population, methods and polypeptide enable the provision (including production and evaluation) of agents with affinity for a predetermined target, through the provision of a polypeptide that is characterized by specific binding to the predetermined target.

Through the disclosed aspects, it is possible to provide polypeptides with affinity for a predetermined target which exhibit little or no non-specific binding.

It is also possible to provide polypeptides with affinity for a predetermined target, which can be readily used as a moiety in a fusion polypeptide.

Furthermore, it is possible to provide polypeptides with affinity for a predetermined target, which solve one or more of the problems known to occur with existing antibody products.

Moreover, it is possible to provide polypeptides with affinity for a predetermined target, which are amenable to use in therapeutic and/or diagnostic applications.

It is also possible to provide polypeptides with affinity for a predetermined target that are readily made by chemical peptide synthesis.

These and other objects are met by the different aspects of the present disclosure and by the corresponding inventive concepts itemized in the appended listing and claimed in the appended claims.

In a first aspect of the disclosure, there is provided a population of polypeptide variants based on a common scaffold, each polypeptide in the population comprising the scaffold amino acid sequence (SEQ ID NO: 165)

$X_{sc1}$AELD$X_{sc2}X_{sc3}$GVG AXXIKXI$X_{sc4}$XA XXVEXVQXXK QXIL

AX wherein, independently of one another,

- $X_{sc1}$ is a scaffold amino acid residue selected from I and L;
- $X_{sc2}$ is a scaffold amino acid residue selected from C and S;
- $X_{sc3}$ is a scaffold amino acid residue selected from K and Y;
- $X_{sc4}$ is a scaffold amino acid residue selected from E and Q; and
- each X individually is a binding amino acid residue corresponding to any amino acid residue.

In one embodiment, each polypeptide in the population comprises the scaffold amino acid sequence (SEQ ID NO: 166)

LAEAKEAA$X_{sc1}$A ELD$X_{sc2}X_{sc3}$GVGAX XIKXI$X_{sc4}$XAXX VEXV

QXXKQX ILAXLP wherein $X_{sc1}$, $X_{sc2}$, $X_{sc3}$, $X_{sc4}$ and each individual X are as defined above.

As stated above, the amino acid residues $X_{sc1}$, $X_{sc2}$, $X_{sc3}$ and $X_{sc4}$ are "scaffold amino acid residues", forming part of the basic structure of each of the variant polypeptides in the population in the same way as the fixed amino acid residues. Typically, they are not involved in randomization for the purpose of generating new target binding characteristics or for selection of new binding variants. In one embodiment of the population according to this aspect of the disclosure, all of the variants in the population have the same amino acid residue in at least one, such as in at least two, such as in at least three, such as in all four, of the scaffold positions $X_{sc1}$, $X_{sc2}$, $X_{sc3}$ and $X_{sc4}$.

In one embodiment, $X_{sc1}$ is I. In another embodiment, $X_{sc1}$ is L.

In one embodiment, $X_{sc2}$ is S. In another embodiment, $X_{sc2}$ is C.

In one embodiment, $X_{sc3}$ is K. In another embodiment, $X_{sc3}$ is Y.

In one embodiment, $X_{sc4}$ is Q. In another embodiment, $X_{sc4}$ is E.

Conversely, the “binding amino acid residues” which are all simply denoted “X”, are typically allowed to vary freely in the population, i.e. they are more or less randomized. They serve to provide the desired variation in the polypeptides' binding ability, enabling the exploration of the sequence space in order to find new combinations with new binding abilities. Polypeptide variants in the population are different chiefly by virtue of having differences in these X positions. Thus, each X individually corresponds to an amino acid residue which is varied. This means that each X may be any amino acid residue independent of the identity of any other residue in the sequence. In one embodiment of the disclosed amino acid sequence, the different varied amino acids X may be chosen from all 20 naturally occurring amino acid residues in such a way that any of these 20 naturally occurring amino acid residues may be present at the corresponding X position in any given variant. In an embodiment in which the members of the population are polypeptides synthesized de novo, it is also possible to include non-naturally occurring amino acid residues into the sequence in a random or pseudo-random manner, and thus provide for additional variation.

The selection of amino acid residue in each position may be randomized to a greater or smaller extent. Thus, it is possible to limit the group from which the different varied amino acid residues are selected to a subgroup of the possible naturally and/or non-naturally occurring amino acid residues.

In one embodiment, one or more of the binding amino acid residues “X” are selected from the group consisting of all naturally occurring amino acid residues except cysteine. One reason to exclude cysteine from the available random pool could be that doing so enables the later, directed introduction of a cysteine residue into the amino acid sequence for labeling purposes (see further below). It would also reduce the risk of disruptive disulfide bonds forming within the polypeptide.

In one embodiment, one or more of the binding amino acid residues “X” are selected from the group consisting of all naturally occurring amino acid residues except proline.

In one embodiment, one or more of the binding amino acid residues “X” in positions corresponding to α-helical regions are selected from the group consisting of all naturally occurring amino acid residues except proline. One reason to exclude proline from the available random pool in these regions is that prolines would typically disrupt the α-helix structure.

In one embodiment, one or more of the binding amino acid residues “X” in the positions corresponding to positions 12, 13, 16, 25, 28, 29, 32 and 36 of SEQ ID NO:165 are selected from the group consisting of all naturally occurring amino acid residues except proline.

In one embodiment, one or more of the binding amino acid residues “X” are selected from the group consisting of all naturally occurring amino acid residues except cysteine and proline.

In one embodiment, one or more of the binding amino acid residues “X” in the positions corresponding to positions 12, 13, 16, 25, 28, 29, 32 and 36 of SEQ ID NO:165 are selected from the group consisting of all naturally occurring amino acid residues except cysteine and proline.

In one embodiment, one or more of the binding amino acid residues “X” are selected from the group consisting of all naturally occurring amino acid residues except cysteine, and one or more of the binding amino acid residues “X” in the positions corresponding to positions 12, 13, 16, 25, 28, 29, 32 and 36 of SEQ ID NO:165 are selected from the group consisting of all naturally occurring amino acid residues except proline. In an example of this embodiment, all of the binding amino acid residues “X” in the positions corresponding to positions 12, 13, 16, 25, 28, 29, 32 and 36 of SEQ ID NO:165 are selected from the group consisting of all naturally occurring amino acid residues except cysteine and proline, while the binding amino acid residues “X” in the positions corresponding to positions 19, 21 and 22 of SEQ ID NO:165 are selected from the group consisting of all naturally occurring amino acid residues except cysteine.

In one embodiment, one or more of the binding amino acid residues “X” are selected from the group consisting of all naturally occurring amino acid residues except methionine.

In other words, the variability in different binding positions may be adjusted individually, between one, meaning no randomization, up to all 20 amino acids. Random introduction of a smaller subset of amino acids may be obtained by design of the nucleotide bases introduced; for example, the codons T(A/C)C may be introduced to obtain a random introduction of either serine or tyrosine at a given position in the polypeptide chain. Likewise, the codons (T/C/A/G) CC may be introduced to obtain a random introduction of serine, proline, threonine and alanine at a given position in the polypeptide chain. The skilled person is aware of many alternatives of base combinations that are useful to obtain different combinations of amino acids at a given X position in the polypeptide chain. The set of amino acids that may appear at a given X position in the polypeptide chain may also be determined by the introduction of trinucleotides during the oligonucleotide synthesis, instead of one deoxyribonucleotide base at a time.

The population consists of a large number of unique variants of polypeptide molecules comprising the disclosed scaffold amino acid sequence. In this context, a large number means a population comprising at least $1\times10^4$ unique polypeptide molecules, or at least $1\times10^6$, or at least $1\times10^8$ or at least $1\times10^{10}$, or at least $1\times10^{12}$, or at least $1\times10^{14}$, or at least $1\times10^{15}$ unique polypeptide molecules. In any case, a population as used in this disclosure is a group large enough to provide the desired size, complexity and variation. The “population” described herein may also be denoted “library”. As used herein, a “unique polypeptide molecule” denotes a specific sequence of amino acid residues, in which all of the $X_{sc1}$, $X_{sc2}$, $X_{sc3}$, $X_{sc4}$ and X residues represent specific amino acid residues. Thus, when it is stated that the disclosed population comprises for example “at least $1\times10^4$ unique polypeptide molecules”, this means that at least $1\times10^4$ different variants of the defined sequence are present in the population.

The polypeptides comprising the scaffold amino acid sequence given above may be considered to be variants of the albumin binding domain of G148-GA3 from *Streptococcus* Protein G. As such, they are derived from *Streptococcus* Protein G. In this context, “derived” does not mean that the polypeptides themselves necessarily directly originate from Protein G. Instead, it means that the scaffold has a sequence and structural resemblance to the albumin binding domain, where amino acids in the hydrophobic core of the three-helical bundle protein are conserved.

Different modifications of, and/or additions to, the polypeptides constituting the population according to the first aspect may be performed in order to tailor the polypeptides to the specific use intended, without departing from the scope of the disclosure. Such modifications and additions are described in more detail below, and may comprise additional amino acids comprised in the same polypeptide chain, or labels and/or therapeutic agents that are chemically conjugated or otherwise bound to the polypeptides constituting the population. In some embodiments additional amino acid residues on the C-terminal end are preferred. In some embodiments, additional amino acid residues on the N-terminal end are preferred. In some embodiments, additions at both ends of the polypeptide chain are preferred.

These additional amino acid residues may play a role in the binding of the polypeptide, but may equally well serve other purposes, related for example to one or more of the production, purification, stabilization, coupling or detection of the polypeptide. Such additional amino acid residues may comprise one or more amino acid residues added for purposes of chemical coupling. An example of this is the addition of a cysteine residue, for example within the sequence, at the very first position in the sequence or at the very last position in the sequence. A cysteine residue to be used for chemical coupling may for example be introduced by replacement of another amino acid on the surface of the protein domain, preferably on a portion of the surface that is not involved in target binding.

In one embodiment, a cysteine residue is present at a position corresponding to position $X_{sc2}$ in SEQ ID NO:165. Without wishing to be bound by theory, and based on structural information available for the ancestral ABD domain, this position is considered to be a surface-exposed position at the end of the first helix in the three-helix bundle of ABD, which is not involved in albumin binding. In engineered albumin binding derivatives of ABD, it has been seen that S is well tolerated at this position, and it is contemplated that the homologous C would also function well in the context of the present disclosure. Introduction of a cysteine at this position has e.g. been previously disclosed for albumin binding ABD variants in WO2012/004384.

Additional amino acid residues may also comprise a “tag” for purification or detection of the polypeptide, such as a hexahistidyl ($His_6$) tag, or a “myc” tag or a “FLAG” tag for interaction with antibodies specific to the tag. The skilled person is aware of other alternatives.

The “additional amino acid residues” may also constitute one or more polypeptide domain(s) with any desired function, such as another binding function, or an enzymatic function, or a metal ion chelating function, or a fluorescent function, or a toxic function, or mixtures thereof. For example, such a polypeptide domain may have a binding affinity for albumin. In one embodiment, an additional domain with a binding affinity for albumin is the naturally occurring ABD or G148-GA3 albumin binding domain from streptococcal Protein G, or an engineered variant thereof with retained or improved albumin binding affinity. Examples of contemplated engineered ABD variants are disclosed in Rozak et al, supra; Jonsson et al, supra; WO2009/016043; Jacobs et al, supra; WO2013/177398; WO2012/004384; and WO2012/162068.

In a second aspect, the disclosure provides a population of polynucleotides. Each polynucleotide in this population encodes a member of a population of polypeptides described above.

In a third aspect, the disclosure provides a combination of a polypeptide population according to the first aspect and a polynucleotide population according to the second aspect, wherein each member of the polypeptide population is physically or spatially associated with the polynucleotide encoding that member via means for genotype-phenotype coupling. This physical or spatial association is more or less strict, depending on the system used. Below follows a recital of possible contemplated ways to achieve genotype-phenotype coupling, all known to the skilled person. Importantly, not all systems need to involve a step of direct physical interaction, and that there may instead be an indirect association in space between a nucleic acid corresponding to a gene (i.e. genotype) and the polypeptide encoded by said gene (i.e. phenotype). “Spatial” association in this context refers to any correspondence between a gene and polypeptide allowing the identification of either member of the pair through the identification of its counterpart. In other words, the association is not random, but specific and directed. Through the physical or spatial association, the knowledge of either one of the nucleotide sequence or amino acid sequence specifically allows for the identification of the corresponding polypeptide or gene.

In one embodiment, the means for genotype-phenotype coupling comprise a phage display system. Phage display systems are well-known to the skilled person, and are, for example, described in Smith G P (1985) Science 228:1315-1317 and Barbas C F et al (1991) Proc Natl Acad Sci USA 88:7978-7982.

In one embodiment, the means for genotype-phenotype coupling comprise a cell surface display system. The cell surface display system may comprise prokaryotic cells, such as $Gram^+$ cells or $Gram^-$ cells, or eukaryotic cells, such as yeast cells or mammalian cells. Prokaryotic systems are, for example, described in Francisco J A et al (1993) Proc Natl Acad Sci USA 90:10444-10448 and Lee S Y et al (2003) Trends Biotechnol 21:45-52. Eukaryotic systems are, for example, described in Boder E T et al (1997) Nat Biotechnol 15:553-557 and Gai S A et al (2007) Curr Opin Struct Biol 17:467-473.

In one embodiment, the means for genotype-phenotype coupling comprise a cell free display system. The cell free display system may comprise a ribosome display system, an in vitro compartmentalization display system, a system for cis display, or a microbead display system. Ribosome display systems are, for example, described in Mattheakis L C et al (1994) Proc Natl Acad Sci USA 91:9022-9026 and Zahnd C et al (2007) Nat Methods 4:269-279. In vitro compartmentalization systems are, for example, described in Sepp A et al (2002) FEBS Lett 532:455-458. Cis display systems are, for example, described in Odegrip R et al (2004) Proc Natl Acad Sci USA 101:2806-2810. Microbead display systems are, for example, described in Nord 0 et al (2003) J Biotechnol 106:1-13.

Furthermore, the means for genotype-phenotype coupling may comprise a non-display system such as the protein-fragment complementation assay (PCA). PCA systems are, for example, described in Koch H et al (2006) J Mol Biol 357:427-441.

In a fourth aspect, the disclosure provides a method for selecting a desired polypeptide with affinity for a predetermined target from a population of polypeptides, comprising the steps:

(a) providing a population of polypeptides according to the first aspect;

(b) bringing the population of polypeptides into contact with the predetermined target under conditions that enable specific interaction between the target and at least one desired polypeptide with affinity for the target; and (c) selecting, on the basis of said specific interaction, the at least one desired polypeptide from the remaining population of polypeptides.

This method is sometimes referred to as the “selection method” according to the disclosure.

Step (a) may comprise the preparatory steps of providing a population of polynucleotides according to the second aspect and expressing said population of polynucleotides to yield said population of polypeptides. The means for yielding a population of polypeptides varies depending on the display system used, and examples of such means may be found in the genotype-phenotype references above. Each member of said population of polypeptides used in the selection method according to the fourth aspect may be associated physically with the polynucleotide encoding that member via means for genotype-phenotype coupling. The means for genotype-phenotype coupling may be one of those discussed above.

Step (b) comprises the steps of bringing the population of polypeptides into contact with the predetermined target under conditions that enable specific interaction between the target and at least one desired polypeptide having an affinity for the target. The range of conditions applicable is determined by the robustness of the target, the robustness of the display system, and by the desired properties of the interaction with the target. For example, a specific method of separating the interaction may be useful, such as acidification to a predetermined pH. The skilled person knows what experiments are required to determine suitable conditions.

Step (c) comprises the selection of at least one polypeptide. The means for selection of desired polypeptide from the remaining population, based on the specific interaction between the predetermined target and at least one desired polypeptide having affinity for the target varies depending on the display system used and may be found in the genotype-phenotype references above. For example, the in vitro display selection systems are cell free, in contrast to systems such as phage display and the protein fragment compartmentalization assay.

In a fifth aspect, the disclosure provides a method for isolating a polynucleotide encoding a desired polypeptide with affinity for a predetermined target, comprising the steps:

- selecting said desired polypeptide and the polynucleotide encoding it from a population of polypeptides using the selection method according to the fourth aspect; and
- isolating the thus separated polynucleotide encoding the desired polypeptide.

This method is sometimes referred to as the "isolation method" according to the disclosure.

The separation of the polynucleotide from the polypeptide may be done differently depending on the display system used for selection. For example, in cell free display systems, such as cis display and ribosome display, the polynucleotide or the corresponding mRNA is retrieved through efficient elution from the polypeptide using means described in the genotype-phenotype references above.

The isolation of the polynucleotide may be done by different methods depending on the display system used for selection. In most of the above described selection systems, the polynucleotide can be directly isolated by specific PCR amplification using appropriate oligonucleotides. Exceptionally, as in ribosome display, the polynucleotide can be isolated from the corresponding mRNA using reverse transcription. The various means for isolation of the polynucleotide may be found in the genotype-phenotype references above.

In a sixth aspect, the disclosure provides a method for identifying a desired polypeptide with affinity for a predetermined target, comprising the steps:

- isolating a polynucleotide encoding said desired polypeptide using the isolation method according to the fifth aspect; and
- sequencing the polynucleotide to establish by deduction the amino acid sequence of said desired polypeptide.

The sequencing of the polynucleotide may be done according to standard procedures well-known to the skilled person.

In a seventh aspect, the disclosure provides a method for selecting and identifying a desired polypeptide with affinity for a predetermined target from a population of polypeptides, comprising the steps:

(a) synthesizing each member of the population of polypeptides according to the first aspect on a separate carrier or bead;

(b) selecting or enriching the carriers or beads based on the interaction of the polypeptide with the predetermined target; and (c) identifying the polypeptide by protein characterization methodology.

In step (c), it is for example possible to use mass spectrometric analysis.

This method is sometimes referred to as the "selection and identification method" according to the disclosure.

In an eighth aspect, the disclosure provides a method for production of a desired polypeptide with affinity for a predetermined target, comprising the steps:

- selecting and identifying a desired polypeptide using the selection method according to the fourth aspect or the selection and identification method according to the seventh aspect; and
- producing said desired polypeptide.

This method is sometimes referred to as the "production method" according to the disclosure.

In the production method according to this aspect, production may be carried out using recombinant expression of a polynucleotide encoding the desired polypeptide. The production may also be carried out using chemical synthesis of the desired polypeptide de novo.

In a ninth aspect, the disclosure provides a method for production of a desired polypeptide with affinity for a predetermined target, comprising the steps:

(a1) isolating a polynucleotide encoding said desired polypeptide using the isolation method according to the fifth aspect; or (a2) backtranslating a polypeptide identified using the selection and identification method according to the seventh aspect; and (b) expressing the thus isolated polynucleotide to produce said desired polypeptide, wherein step (b) is performed after step (a1) or (a2) as applicable.

The expression of the polynucleotide may be done in any suitable expression host, such as but not limited to bacterial cells, yeast cells, insect cells or mammalian cells.

As will be readily understood, any polypeptide selected from the disclosed population or library will fulfil the sequence definition common to all variants or members in the population. It will typically be a polypeptide with affinity for a predetermined target, and be useful in any application where binding to that target may be exploited.

In a tenth aspect of the disclosure, there is therefore provided a polypeptide comprising an amino acid sequence which is at least 97 identical to (SEQ ID NO: 165)

$X_1AELDX_6X_7GVG\ AX_{12}X_{13}IKX_{16}IX_{18}X_{19}A\ X_{21}X_{22}VEX_{25}VQX_{28}$ $X_{29}K\ QX_{32}ILAX_{36}$ wherein, independently of one another, $X_1$ is selected from I and L;

$X_6$ is selected from C and S;

$X_7$ is selected from K and Y;

$X_{18}$ is selected from E and Q; and each of $X_{12}$, $X_{13}$, $X_{16}$, $X_{19}$, $X_{21}$, $X_{22}$, $X_{25}$, $X_{28}$, $X_{29}$, $X_{32}$ and $X_{36}$ is any amino acid residue.

In one embodiment of this aspect, the polypeptide comprises an amino acid sequence which is at least 97% identical to LAEAKEAA $X_1AELDX_6X_7GVG$ $AX_{12}X_{131}KX_{161}X_{18}X_{19}A$ $X_{21}X_{22}VEX_{25}VQX_{28}X_{29}K$ $QX_{32}ILAX_{36}$ LP (SEQ ID NO:166), in which all residues denoted "$X_n$" are as defined above.

In one embodiment, $X_1$ is I. In another embodiment, $X_1$ is L.

In one embodiment, $X_6$ is S. In another embodiment, $X_6$ is C.

In one embodiment, $X_7$ is K. In another embodiment, $X_7$ is Y.

In one embodiment, $X_{18}$ is E. In another embodiment, $X_{18}$ is Q.

In one embodiment, the amino acid residue in position 11 is A.

As the skilled person will realize, the function of any polypeptide, such as the polypeptide of this tenth aspect of the present disclosure, is dependent on its tertiary structure. It is therefore possible to make minor changes to the sequence of amino acids in a polypeptide without affecting the function thereof, as long as the general fold and overall structure doesn't change substantially. The disclosure encompasses modifications of the polypeptide that are such that they do not alter the functional properties of the polypeptide, such as any substantial impact on stability and/or binding affinity for a predetermined target.

In this way, also encompassed by the present disclosure is a polypeptide comprising an amino acid sequence with 97% or greater identity to SEQ ID NO:165 or SEQ ID NO:166. In some embodiments, the polypeptide may comprise a sequence which is at least 98%, such as at least 99%, such as 100% identical to SEQ ID NO:165 or SEQ ID NO:166.

In some embodiments, such variation in SEQ ID NO:165 or SEQ ID NO:166 may be found in any position of the sequence of the polypeptide as disclosed herein. In other embodiments, differences may be found only in scaffold amino acid residues. In other embodiments, differences may be found only in the amino acid residues which confer target binding specificity. For example, it is possible that an amino acid residue belonging to a certain functional grouping of amino acid residues (e.g. hydrophobic, hydrophilic, polar etc) could be exchanged for another amino acid residue from the same functional group.

The term "% identity", as used throughout the specification, may for example be calculated as follows. The query sequence is aligned to the target sequence using the CLUSTAL W algorithm (Thompson et al, Nucleic Acids Research, 22: 4673-4680 (1994)). A comparison is made over the window corresponding to one of the aligned sequences, for example the shortest. The window may in some instances be defined by the target sequence. In other instances, the window may be defined by the query sequence. The amino acid residues at each position are compared, and the percentage of positions in the query sequence that have identical correspondences in the target sequence is reported as % identity.

The advantages and modifications discussed above for the polypeptides constituting the population according to the present disclosure are also applicable to the polypeptides according to the disclosure or polypeptides obtained by any of the disclosed methods. Thus, in analogy to the disclosure above concerning the population according to the first aspect, modifications of, and/or additions to, the polypeptides according to this tenth aspect may be employed without departing from the scope of the present disclosure.

In particular, a polypeptide according to the tenth aspect may also comprise a second (and optionally further) polypeptide moiety, such that the polypeptide is a fusion polypeptide with one moiety fulfilling the definition of a polypeptide according to the tenth aspect, and at least one further moiety (optionally more) which provides a desired function. This desired function may be the same as, or different from, the function provided by the polypeptide according to the tenth aspect, which is typically, but not always, a binding function based on an affinity for a predetermined target. Alternatives and other considerations in this regard are given above in connection with the first aspect, and are equally applicable to this tenth aspect.

Also disclosed, as an eleventh aspect, is a polynucleotide encoding a polypeptide according to the tenth aspect. The disclosure also provides, as a twelfth aspect, a method of producing a polypeptide according to the tenth aspect, comprising the step of expressing a polynucleotide according to the eleventh aspect.

In the present disclosure, expressions like "binding affinity for a predetermined target", "binding to a predetermined target" and the like refer to a property of a polypeptide which may be directly measured through the determination of the affinity constants, i.e. the amount of polypeptide that associates and dissociates at a given antigen concentration. Different methods can be used to determine affinity constants or other similar parameters, such as, but not limited to, competition analysis, equilibrium analysis and microcalorimetric analysis, and real-time interaction analysis for example based on surface plasmon resonance interaction (SPR).

In the case of SPR, the binding affinity may be tested in an experiment in which the predetermined target, or a fragment thereof, is immobilized on a sensor chip of the instrument, and the sample containing the polypeptide to be tested is passed over the chip. Alternatively, the polypeptide to be tested is immobilized on a sensor chip of the instrument, and a sample containing the predetermined target, or a fragment thereof, is passed over the chip. The skilled person may then interpret the results obtained by such experiments to establish at least a qualitative measure of the binding affinity of the polypeptide for the predetermined target. If a quantitative measure is desired, for example to determine a $K_D$ value for the interaction, surface plasmon resonance methods may also be used. Binding values may for example be defined in a Biacore (GE Healthcare) or ProteOn XPR 36 (Bio-Rad) instrument. The predetermined target is suitably immobilized on a sensor chip of the instrument, and samples of the polypeptide whose affinity is to be determined are prepared by serial dilution and injected in random order. $K_D$ values may then be calculated from the results using for example the 1:1 Langmuir binding model of the BIAevaluation 4.1 software, or other suitable software, provided by the instrument manufacturer.

The term "binding affinity for a predetermined target", as used herein, may also refer to a property of a polypeptide which may be tested for example by ELISA. For example, the binding affinity may be tested in an experiment in which samples of the polypeptide are captured on antibody-coated ELISA plates and biotinylated predetermined target, or a fragment thereof, is added, followed by streptavidin conjugated HRP. TMB substrate is added and the absorbance at 450 nm is measured using a multi-well plate reader, such as Victor[3] (Perkin Elmer). The skilled person may then interpret the results obtained by such experiments to establish at least a qualitative measure of the binding affinity of the complex for the predetermined target. If a quantitative measure is desired, for example to determine the EC50 value (the half maximal effective concentration) for the interaction, ELISA may also be used. The response of the polypeptide against a dilution series of the predetermined target, or a fragment thereof, is measured using ELISA as described above. The skilled person may then interpret the results obtained by such experiments, and EC50 values may be calculated from the results using for example GraphPad Prism 5 and non-linear regression.

Methods such as those mentioned above are well-known to the skilled person and are further described, for example, in Neri D et al (1996) Tibtech 14:465-470 and Jansson M et al (1997) J Biol Chem 272:8189-8197.

The polypeptides, populations and methods according to the disclosure enable the provision of agents with an affinity for a predetermined target, through the provision of a polypeptide that is characterized by specific binding to the predetermined target.

It is also possible to provide polypeptides binding to a predetermined target that exhibit little or no non-specific binding.

It is also possible to provide polypeptides binding to a predetermined target that can readily be used as a moiety in a fusion polypeptide.

Furthermore, it is possible to provide polypeptides binding to a predetermined target that solve one or more of the known problems experienced with existing antibody reagents, in particular due to their smaller size. For example, polypeptides according to the disclosure are expected to show favorable tissue penetration, and enable the use of alternative administration routes and higher molar doses per unit weight.

The small size of the polypeptides according to the disclosure is also expected to provide benefits when using them as affinity reagents in in vivo imaging applications, for example because unbound polypeptides will be rapidly cleared. This is expected to provide for images of high contrast.

Moreover, it is possible to provide polypeptides binding to a predetermined target that are amenable to use in therapeutic and/or diagnostic applications.

It is also possible to provide polypeptides binding to a predetermined target that are easily made by chemical peptide synthesis. For example, besides their small size, they comprise relatively few amino acid residues that commonly cause problems in synthesis, such as asparagine, arginine, aspartic acid and methionine. In general, a polypeptide as defined herein does not comprise scaffold amino acid residues that are associated with polypeptide stability problems, such as methionine, asparagine and the dipeptide asparagine-proline.

In contrast to known ABD variants with novel binding affinities, the polypeptide according to the disclosure is designed using the deimmunized variant PP013 (SEQ ID NO:159) as a starting point. As such, it is expected that the disclosed polypeptide, for example resulting from selection according to the disclosed methods from the disclosed population, will have fewer immunogenic epitopes than comparable ABD variants based on e.g. the G148-GA3 wildtype sequence (SEQ ID NO:158).

Also, certain known ABD variants with novel binding affinities retain an ability to bind albumin. In various applications, this may interfere with the novel affinity, and it is expected that embodiments of the polypeptides disclosed herein do not exhibit this feature. Rather, the albumin binding capacity is intended to be completely abrogated in the disclosed polypeptide, and replaced by the new affinity for a predetermined target.

Polypeptides according to the present disclosure may be used as detection reagents, capture reagents, separation reagents, diagnostic agents for diagnostics in vivo or in vitro, as therapeutic agents in their own right or as means for targeting other therapeutic and/or diagnostic agents to the predetermined target. Methods that employ the polypeptides in vitro may be performed in different formats, such as in microtiter plates, in protein arrays, on biosensor surfaces, on tissue sections, and so on.

Polypeptides according to the present disclosure may be produced by any known means, including chemical synthesis or expression in different prokaryotic or eukaryotic hosts, including bacterial cells, yeast cells, plant cells, insect cells, whole plants and transgenic animals.

While the polypeptides, populations of polypeptides and methods for identification, selection, isolation and production disclosed herein have been described with reference to various exemplary aspects and embodiments, it will be understood by those skilled in the art that various changes may be made and equivalents may be substituted for elements thereof without departing from the scope of the present disclosure. In addition, many modifications may be made to adapt a particular situation or molecule to the teachings of the disclosure without departing from the essential scope thereof. Therefore, it is intended that the disclosure not be limited to any particular embodiment contemplated, but to include all embodiments falling within the scope of the appended claims.

BRIEF DESCRIPTION OF THE FIGURES

FIG. 1 shows sequence logos visualizing the frequency of the respective amino acid in each position within Y variants selected from the preliminary library Ylib001Naive.I and verified by ELISA to interact with its respective target molecule. (A) Logo based on 18 Y variants verified to bind C4; (B) Logo based on 106 Y variants verified to bind IL-6; (C) Logo based on 21 Y variants verified to bind insulin; and (D) Combined sequence logo including (A)-(C), i.e.Y variants verified to bind C4, IL-6 or insulin.

FIG. 3 shows CD spectra collected at 20° C. before (black) and after (grey) variable temperature measurement (VTM) of the insulin binding Y variants Y00274 (A) and Y00275 (B).

FIG. 4 shows VTM and CD spectra collected for the C4 binding Y variant Y00792 (A-B), the insulin binding Y variant Y00301 (C-D) and the IL-6 binding variant Y02444 (E-G). The VTMs are shown in FIGS. 4A, C and E, whereas the CD spectra collected at 20° C. before (black) and after (grey) VTM are shown in Figure B, D and F.

EXAMPLES

Figure 2:
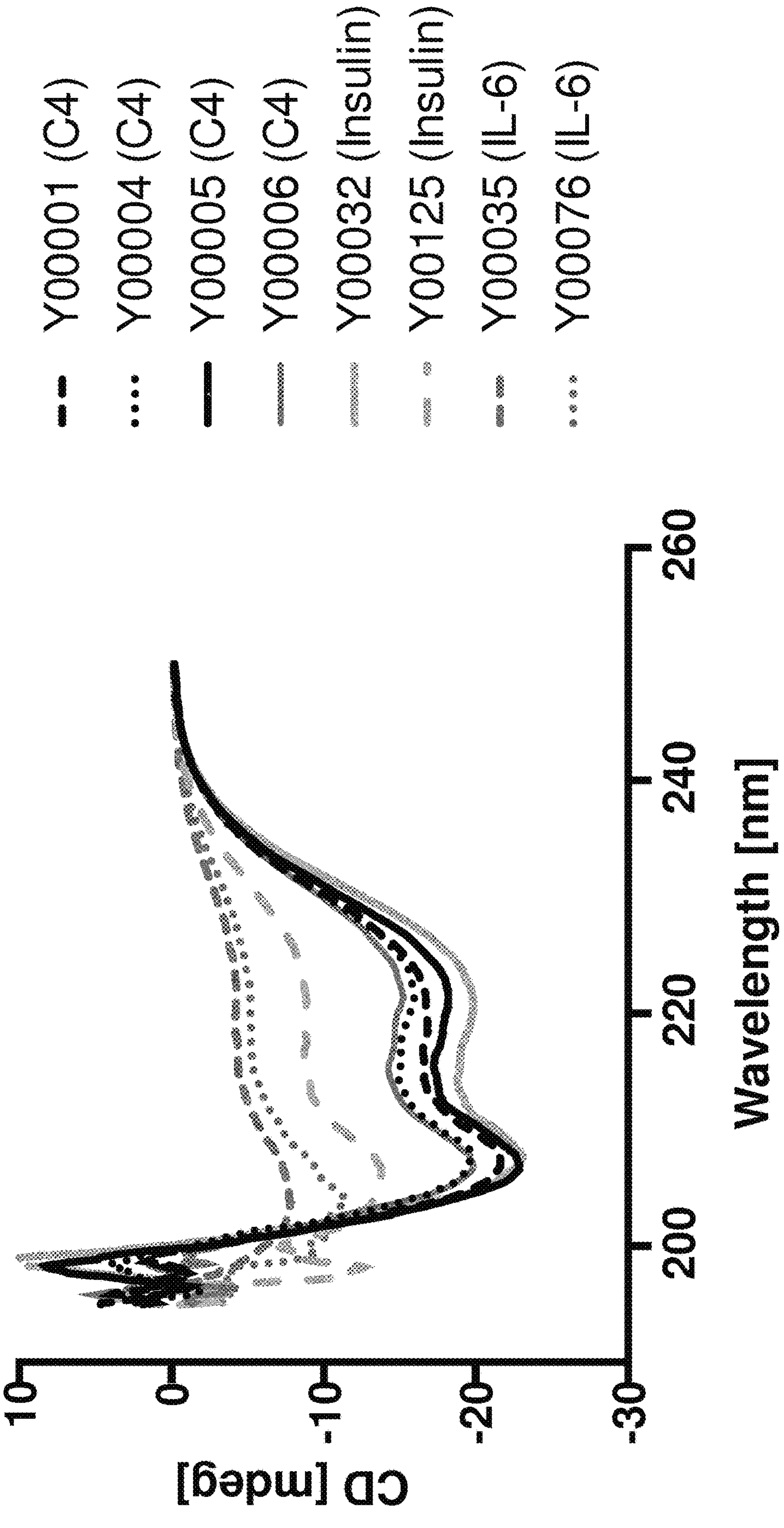
FIG. 2 shows circular dichroism (CD) spectra collected at 20° C. of C4, IL-6 and insulin binding Y variants selected from Ylib001Naive.I.

The following Examples disclose design and construction of a protein library based on a scaffold sequence inspired by the albumin binding domain PP013 (SEQ ID NO:159), in turn derived from ABD of G148-GA3 (SEQ ID NO:158). The Examples show the successful assembly of a high complexity library while retaining high stability and solubility. The successful use of the designed library for selection of new ligands for three different target molecules is also demonstrated.

A critical part of the approach was the decision concerning which residues to randomize and which residues to keep fixed, as well as the decision concerning the identity of the fixed residues. In this regard, randomization at positions critical for intramolecular stabilization should be avoided, but, at the same time, the potential of the library to offer optimal coverage and evaluation of possible alternative sequences can be limited by a suboptimal choice of surface-exposed residues. In the process of identifying suitable positions to randomize, comprehensive knowledge of the scaffold protein was applied, including structural information for the domain G148-GA3 (Kraulis et al, supra; Johansson et al, supra) and information related to its albumin binding activity (Lejon et al, supra). In the design of new scaffolds, the surface area involved in the native interaction has often been the main focus for randomization. However, randomizing exactly the same residues as those providing binding affinity in the ancestor polypeptide may be suboptimal when aiming to design a broad library that can be used to find novel binders against a variety of targets with different sizes and structures. Furthermore, the native binding interface may not only be central for target binding, but may also be important for maintaining the framework and structural stability of the scaffold. Thus, focusing on regions that are not directly involved in the native interaction may be equally important, in order to identify the optimal region for randomization. In brief, the following procedure was applied:

1) Design of a first library with the aim to establish what positions could be varied to provide new binding abilities, and to incorporate flexibility and improvements in the scaffold positions.
2) Creation of this first library, denoted "Ylib001Naive.I".
3) Selections against a first set of targets.
4) Assessment of selected ligands, primarily in terms of binding and stability.
5) Sequential mutational programs for additional improvements; including generation, production and assessment of mutated ligands.
6) Design of a second library based on the results from steps 3)-5), with decisions on what binding positions to vary in order to generate novel binding abilities, and on what scaffold residues should be kept fixed and to what amino acid residues.
7) Creation of this second library, denoted "Ylib002Naive.I".
8) Selections against a second set of targets.
9) Assessment of selected ligands in terms of binding, stability, producibility and solubility, in order to verify the quality of the library and the selected variants.
10) Sequential mutational programs for fine-tuning of library.
11) Design of a scaffold according to the disclosure based on the entire preceding procedure.

The scaffold sequence and populations or libraries described herein are referred to as "Y scaffold" and "Y populations" or "Y libraries", respectively, and binding variants derived therefrom are denoted "Y variants".

Example 1

Description of General Procedures

Summary

This Example describes general procedures for cloning, production and analysis. These general procedures were used throughout the Examples 2-8 unless otherwise specified in the respective Example.

Materials and Methods

Biotinylation of Target Protein:

Target proteins were biotinylated using No-Weigh EZ-Link Sulfo-NHS-LC-Biotin (Thermo Scentific) at a 10× molar excess, according to the manufacturer's recommendations. The reactions were performed at room temperature (RT) for 30 min. Buffer exchange to phosphate buffered saline (PBS; 10 mM phosphate, 137 mM NaCl, 2.68 mM KCl, pH 7.4) was performed after biotinylation, using either dialysis cassettes (Pierce, Slide-a-lyzer (3500 MWCO)) or illustra NAP-5 desalting columns (GE Healthcare) according to the manufacturers' instructions.

Cloning of Y Variants:

Cloning was performed using methods known in the art. In brief, one of the following procedures was applied:

1) The DNA encoding the Y variant(s) of interest was amplified from the library vector pAY03686 using a standard PCR protocol and AmpliTaq Gold polymerase (Life Technologies). Fragments were restricted using enzymes SalI-HF and BamHI-HF (New England Biolabs) and purified using QIAquick PCR Purification Kit (QIAGEN) according to the supplier's recommendations. An expression vector (with T7 promoter) providing an N-terminal $His_6$ tag was prepared and digested with the same restriction enzymes. The vector was run on a preparative 1% agarose (BioNordika AB) gel electrophoresis and purified using QIAGEN Gel Extraction Kit (QIAGEN) according to the supplier's recommendations. Gene fragments and vector were ligated using T4 DNA ligase (Thermo Scientific) in ligase buffer and electroporated into electrocompetent *Escherichia coli* (*E. coli*) TOP10 cells. The transformed cells were spread on TBAB plates (30 g/l tryptose blood agar base) supplemented with 50 μg/ml of kanamycin, followed by incubation at 37° C. overnight.

2) DNA encoding the Y variant(s) of interest was ordered as fragment genes from GeneArt (Life Technologies) or Twist Bioscience, and restricted using enzymes BamHI-HF and NgoMIV (New England Biolabs). An expression vector (with T7 promoter) providing an N-terminal $His_6$ tag was prepared and digested with the same restriction enzymes. Ligation and transformation were performed as described above.

3) DNA encoding the Y variant(s) of interest were ordered from GeneArt as fully cloned genes in a custom vector (expression vector (with T7 promoter) providing an N-terminal $His_6$ tag). Transformation was performed as described above.

Sequencing:

Bacterial clones harboring plasmids of interest were picked for sequencing. PCR fragments were amplified from single colonies using a standard PCR program and a complementary pair of primers. Sequencing of amplified fragments was performed using a biotinylated oligonucleotide and a Big Dye® Terminator v3.1 Cycle Sequencing Kit (Applied Biosystems), in accordance with the manufacturer's protocol. The sequencing reactions were purified by binding to magnetic streptavidin coated beads (Detach Streptavidin Beads, Nordiag) using a Magnatrix 8000 (Magnetic Biosolutions) instrument and analyzed on an ABI PRISM® 3130xl Genetic Analyzer (PE Applied Biosystems).

Protein Expression:

*E. coli* T7E2 cells were transformed with plasmids containing the gene fragment of each respective Y variant. The resulting recombinant strains were generally cultivated in media supplemented with 50 μg/ml kanamycin at 30-37° C. in 50 ml scale using the EnPresso protocol (Enpresso GmbH). In order to induce protein expression, isopropyl-β-D-1-thiogalactopyranoside (IPTG) was added to a final concentration of 0.5 mM at an optical density at 600 nm ($OD_{600}$) of approximately 10. After induction, the cultures were incubated for 16 h. The cells were harvested by centrifugation. Alternatively, the culture was performed at 37° C. in 980 ml of TSB-YE medium (tryptic soy broth 30 g/l supplemented with yeast extract 5 g/l) supplemented with 50 μg/ml kanamycin, and protein expression induced with 0.2 mM IPTG at $OD_{600}$=2, followed by incubation for 5 h before harvesting of the cells by centrifugation. The total yield as well as the fraction of soluble and insoluble product of the respective Y variant was estimated based on SDS-PAGE analysis.

Purification of Y Variants with an N-Terminal $His_6$-Tag:

Cells were re-suspended in binding buffer (20 mM sodium phosphate, 0.5 M NaCl, 20 mM imidazole, pH 7.4) supplemented with Benzonase® (Merck). After cell disruption, cell debris was removed by centrifugation and each supernatant was applied on a 1 ml His GraviTrap IMAC column (GE Healthcare). Contaminants were removed by washing with wash buffer (20 mM sodium phosphate, 0.5 M NaCl, 60 mM imidazole, pH 7.4) and the Y variants were subsequently eluted with elution buffer (20 mM sodium phosphate, 0.5 M NaCl, 500 mM imidazole, pH 7.4). Buffer exchange to PBS was performed using PD-10 desalting columns (GE Healthcare) according to the manufacturer's instructions.

Protein Analysis and Verification:

Protein concentrations were determined by measuring the absorbance at 280 nm, using a NanoDrop® ND-1000 spectrophotometer (Saveen Werner AB) and the extinction coefficient of the respective protein. The purity was analyzed by SDS-PAGE stained with Coomassie Blue and the identity of each purified Y variant was confirmed using LC/MS analysis.

Circular Dichroism (CD) Spectroscopy Analysis:

The respective Y variant was diluted to 0.5 mg/ml in PBS. A CD spectrum at 250-195 nm was obtained at 20° C. In addition, a variable temperature measurement (VTM) was performed to determine the melting temperature (Tm). In the VTM, absorbance was measured at 221 nm while the temperature was raised from 20° C. to 90° C. with a temperature gradient of 5° C./min. A new CD spectrum was obtained at 20° C. after the heating procedure, in order to study the refolding ability of the Y variants. The CD measurements were performed on a Jasco J-810 spectropolarimeter (Jasco Scandinavia AB) using a cell with an optical path length of 1 mm.

Kinetic Analysis Using Surface Plasmon Resonance:

Kinetic constants ($k_a$ and $k_d$) and affinities ($K_D$) were determined for $His_6$-tagged Y variants using a Biacore T200 instrument (GE Healthcare). Target proteins C4, IL-6 and insulin, respectively, were immobilized in separate flow cells on the carboxylated dextran layer of different CM5 chip surfaces (GE Healthcare). Immobilization was performed using amine coupling chemistry according to the manufacturer's protocol and PBS pH 7.4 supplemented with 0.1 Tween20 (PBST 0.1%) as running buffer. The ligand immobilization levels on the surfaces were 3280-8830 RU for C4, 495-1184 RU for IL-6, and 270-282 RU for insulin. One flow cell surface on each chip was activated and deactivated for use as blank during analyte injections. In the kinetic experiment, PBST 0.1% was used as running buffer at a flow rate of 30 μl/min. The analytes, i.e. Y variants, were each diluted in PBST 0.1 buffer at concentrations of 1000, 500, 100, 50 and 10 nM and injected for 5 min, followed by dissociation in running buffer for 3 min. After dissociation, the surfaces were regenerated with one injection of 30 μl 10 mM HCl. Kinetic constants were calculated from the sensorgrams using the Langmuir 1:1 model of Biacore T200 Evaluation software 2.0 (GE Healthcare).

Example 2

Design and Construction of a Library Based on an ABD Variant Scaffold

Summary

This Example describes the design and construction of a first library to be used for a first selection described below in Example 3. The aim was to establish what positions to vary in order to achieve new binding capabilities, and to incorporate flexibility and improvements in the scaffold.

Materials and Methods

Library Design:

A library was designed based on the albumin binding domain PP013 (SEQ ID NO:159) and on information concerning the structure of the G148-GA3 domain. Surface-exposed amino acid positions involved in the natural binding to albumin, positions in the near vicinity of the binding surface, as well as additional positions in helix one and in the loop between helix one and helix two, were targeted for variegation. The amino acid positions in PP013 selected for randomization were: N9, Y15, V17, S18, D19, F20, Y21, K22, R23, L24, K27, A28, K29, T30, G33, A36, L37, A40, A43, and A44. Each position was randomized allowing different compositions of amino acid residues (all excluding the amino acids C, M and P). Full randomization at each of these twenty positions was not possible, because the theoretical size of the library would then widely exceed the possible practical size. Therefore, positions thought not to be involved in binding (i.e. "scaffold positions") were randomized more restrictively, whereas the degree of randomization in positions potentially involved in binding (i.e. "binding positions") ranged from 11 to 17 allowed amino acid residues. Limitations applied depended on the nature of the position in the structure of the G148-GA3 domain (helix position versus loop position) and expected relevance to binding function. In some positions, homologous residues were excluded, e.g. allowing K but not R, or allowing L and V but not I. The selection of amino acids at the respective position and their theoretical distributions in the resulting library, denoted "Ylib001Naive.I", are displayed in Table 1.

Using split-pool synthesis, the following DNA oligo of 177 bp was generated, encoding a partially randomized amino acid sequence: 5'-AA ATA AAT GGA TCC AGC CTG GCT GAG GCG AAA GAA GCC GCG NNN GCC GAG CTG GAT AGC NNN GGT NNN NNN NNN NNN NNN NNN NNN NNN ATC GAG NNN NNN NNN NNN GTT GAG NNN GTT GAA NNN NNN AAA GAA NNN ATT CTG NNN NNN CTG CCG GCG AGC GGT AGC GTC GAO ATT ATT TA-3' (SEQ ID NO:163; randomized codons are illustrated as NNN) flanked by restriction sites SalI and BamHI. The oligonucleotide was ordered from Atum (formerly DNA2.0). The resulting theoretical library size is $7.8\times10^{16}$ variants.

TABLE 1

The Ylib001Naive.I library. Percentages of the amino acids used in each of the 20 varied positions are indicated.

| | | Position with reference to SEQ ID NO: 165 | | | | | | | | | |
|---|---|---|---|---|---|---|---|---|---|---|---|
| | | 1 | 7 | 9 | 10 | 11 | 12 | 13 | 14 | 15 | 16 |
| | | Position in full length Y variant (with ref to SEQ ID NO: 159) | | | | | | | | | |
| | Codon | 9 | 15 | 17 | 18 | 19 | 20 | 21 | 22 | 23 | 24 |
| A | Ala | 0 | 33.3 | 0 | 8.3 | 33.3 | 5.9 | 6.3 | 0 | 0 | 6.3 |
| C | Cys | 0 | 0 | 0 | 0 | 0 | 0 | 0 | 0 | 0 | 0 |
| D | Asp | 0 | 0 | 0 | 8.3 | 33.3 | 5.9 | 6.3 | 0 | 0 | 6.3 |
| E | Glu | 0 | 0 | 0 | 8.3 | 33.3 | 5.9 | 6.3 | 0 | 33.3 | 6.3 |
| F | Phe | 0 | 0 | 0 | 0 | 0 | 5.9 | 6.3 | 0 | 0 | 6.3 |
| G | Gly | 0 | 0 | 0 | 8.3 | 0 | 5.9 | 0 | 0 | 0 | 0 |
| H | His | 0 | 0 | 0 | 8.3 | 0 | 5.9 | 6.3 | 0 | 0 | 6.3 |
| I | Ile | 33.3 | 0 | 50.0 | 0 | 0 | 5.9 | 6.3 | 50.0 | 0 | 6.3 |
| K | Lys | 0 | 33.3 | 0 | 8.3 | 0 | 5.9 | 6.3 | 50.0 | 33.3 | 6.3 |
| L | Leu | 33.3 | 0 | 0 | 0 | 0 | 5.9 | 6.3 | 0 | 0 | 6.3 |
| M | Met | 0 | 0 | 0 | 0 | 0 | 0 | 0 | 0 | 0 | 0 |
| N | Asn | 33.3 | 0 | 0 | 8.3 | 0 | 5.9 | 6.3 | 0 | 0 | 6.3 |
| P | Pro | 0 | 0 | 0 | 0 | 0 | 0 | 0 | 0 | 0 | 0 |
| Q | Gln | 0 | 0 | 0 | 8.3 | 0 | 5.9 | 6.3 | 0 | 0 | 6.3 |
| R | Arg | 0 | 0 | 0 | 0 | 0 | 5.9 | 6.3 | 0 | 0 | 6.3 |
| S | Ser | 0 | 0 | 0 | 8.3 | 0 | 5.9 | 6.3 | 0 | 33.3 | 6.3 |
| T | Thr | 0 | 0 | 0 | 8.3 | 0 | 5.9 | 6.3 | 0 | 0 | 6.3 |
| V | Val | 0 | 0 | 50.0 | 8.3 | 0 | 5.9 | 6.3 | 0 | 0 | 6.3 |
| W | Trp | 0 | 0 | 0 | 0 | 0 | 5.9 | 6.3 | 0 | 0 | 6.3 |
| Y | Tyr | 0 | 33.3 | 0 | 8.3 | 0 | 5.9 | 6.3 | 0 | 0 | 6.3 |

| | | Position with reference to SEQ ID NO: 165 | | | | | | | | | |
|---|---|---|---|---|---|---|---|---|---|---|---|
| | | 19 | 20 | 21 | 22 | 25 | 28 | 29 | 32 | 35 | 36 |
| | | Position in full length Y variant (with ref to SEQ ID NO: 159) | | | | | | | | | |
| | Codon | 27 | 28 | 29 | 30 | 33 | 36 | 37 | 40 | 43 | 44 |
| A | Ala | 5.9 | 50.0 | 8.3 | 8.3 | 7.1 | 9.1 | 6.3 | 6.3 | 50 | 8.3 |
| C | Cys | 0 | 0 | 0 | 0 | 0 | 0 | 0 | 0 | 0 | 0 |
| D | Asp | 5.9 | 0 | 0 | 8.3 | 0 | 0 | 6.3 | 6.3 | 0 | 8.3 |
| E | Glu | 5.9 | 0 | 8.3 | 0 | 7.1 | 9.1 | 6.3 | 6.3 | 0 | 8.3 |
| F | Phe | 5.9 | 0 | 8.3 | 8.3 | 7.1 | 9.1 | 6.3 | 6.3 | 0 | 0 |
| G | Gly | 5.9 | 50.0 | 8.3 | 8.3 | 7.1 | 0 | 0 | 0 | 0 | 8.3 |
| H | His | 5.9 | 0 | 8.3 | 8.3 | 7.1 | 9.1 | 6.3 | 6.3 | 0 | 8.3 |
| I | Ile | 5.9 | 0 | 0 | 8.3 | 0 | 0 | 6.3 | 6.3 | 0 | 0 |
| K | Lys | 5.9 | 0 | 8.3 | 0 | 7.1 | 9.1 | 6.3 | 6.3 | 50 | 8.3 |
| L | Leu | 5.9 | 0 | 8.3 | 0 | 7.1 | 9.1 | 6.3 | 6.3 | 0 | 0 |
| M | Met | 0 | 0 | 0 | 0 | 0 | 0 | 0 | 0 | 0 | 0 |
| N | Asn | 5.9 | 0 | 0 | 0 | 7.1 | 0 | 6.3 | 6.3 | 0 | 8.3 |
| P | Pro | 0 | 0 | 0 | 0 | 0 | 0 | 0 | 0 | 0 | 0 |
| Q | Gln | 5.9 | 0 | 8.3 | 8.3 | 7.1 | 9.1 | 6.3 | 6.3 | 0 | 8.3 |
| R | Arg | 5.9 | 0 | 0 | 8.3 | 0 | 0 | 6.3 | 6.3 | 0 | 0 |
| S | Ser | 5.9 | 0 | 8.3 | 8.3 | 7.1 | 9.1 | 6.3 | 6.3 | 0 | 8.3 |
| T | Thr | 5.9 | 0 | 0 | 0 | 7.1 | 0 | 6.3 | 6.3 | 0 | 8.3 |
| V | Val | 5.9 | 0 | 8.3 | 8.3 | 7.1 | 9.1 | 6.3 | 6.3 | 0 | 8.3 |
| W | Trp | 5.9 | 0 | 8.3 | 8.3 | 7.1 | 9.1 | 6.3 | 6.3 | 0 | 0 |
| Y | Tyr | 5.9 | 0 | 8.3 | 8.3 | 7.1 | 9.1 | 6.3 | 6.3 | 0 | 8.3 |

Library Construction:

A phagemid vector denoted pAY03686 was constructed in a step-wise manner beginning with pUC119 (Vieira and Messing Meth. Enzymol. 1987, 153:3-11) and using standard molecular biology methods to introduce essential parts in the translation cassette. Thus, the resulting library vector pAY03686 encodes, under regulation of the *E. coli* lac promoter, the *E. coli* OmpA leader peptide in frame with the variable Y library, a 58 amino acid residue Taq polymerase binding domain (Z03639, SEQ ID NO:160) and residues 249-406 of M13 filamentous phage coat protein III (Lowman et al, Biochemistry, 1991, 30:10832-10838), the latter preceded by an amber stop codon.

The library oligo was amplified using AmpliTaq Gold polymerase during 12 cycles of PCR, and pooled products were purified with QIAquick PCR Purification Kit according to the supplier's recommendations. The purified pool of randomized library fragments was digested with restriction enzymes SalI-HF and BamHI-HF and concentrated using QIAquick PCR Purification Kit. Subsequently, the product was run on a preparative 2.5% agarose (NuSieve® GTG® Agarose, Lonza) gel electrophoresis and purified using QIAGEN Gel Extraction Kit (QIAGEN) according to the supplier's recommendations.

The phagemid vector pAY03686 was restricted with the same enzymes and purified using phenol/chloroform extraction and ethanol precipitation. The restricted fragments and the restricted vector were ligated in a molar ratio of 5:1 with T4 DNA ligase for 2 h at RT, followed by overnight incubation at 4° C. The ligated DNA was recovered by phenol/chloroform extraction and ethanol precipitation, followed by dissolution in 10 mM Tris-HCl, pH 8.5. Thus, the resulting library in vector pAY03686 encoded Y variants each fused to a Taq polymerase binding domain (Z03639).

The ligation reactions (approximately 160 ng DNA/transformation) were electroporated into electrocompetent *E. coli* ER2738 cells (Lucigen). Immediately after electroporation, approximately 1 ml of recovery medium (supplied with the *E. coli* ER2738 cells) was added. The transformed cells were incubated at 37° C. for 60 min. Samples were taken for titration and for determination of the number of transformants. The cells were thereafter pooled and cultivated overnight at 37° C. in 3 I of TSB-YE medium supplemented with 10 μg/ml tetracycline and 100 μg/ml ampicillin. The cells were pelleted for 15 min at 4,000 g and re-suspended in a 40% glycerol solution. The cells were aliquoted and stored at −80° C. Clones from the library of Y variants were sequenced in order to verify the content and to evaluate the outcome of the constructed library vis-à-vis the library design. Sequencing was performed as described in Example 1 and the amino acid distribution was verified.

Results

Library Design:

A library denoted Ylib001Naive.I was designed based on the G148-GA3 variant PP013, which has an albumin binding surface positioned from helix two to helix three of the triple alpha-helical protein. The amino acid positions involved in the albumin binding together with positions in the vicinity of the binding surface were used to create a combinatorial library for exploring the possibility to redefine the binding function. In addition, a set of surface-exposed residues in helix one and in the loop preceding helix two was variegated, resulting in a total of 20 amino acid positions that were targeted for randomization (Table 1). Taking all theoretically possible combinations into account, the theoretical size of the designed library was $7.8\times10^{16}$ unique Y variants.

Library Construction:

A new phagemid vector, denoted pAY03686, was constructed for monovalent display using the M13 filamentous phage coat protein III. The library Ylib001Naive.I was constructed using pAY03686. The actual size of the library, determined by titration after transformation to *E. coli* ER2738 cells, was $1.0\times10^{10}$ transformants. The library quality was tested by sequencing of 192 transformants and by comparing their actual sequences with the theoretical design. Sequence analysis of individual library members verified a distribution of codons that was in accordance with the theoretical design. A library of potential binders in a novel scaffold sequence was thus successfully constructed.

Example 3

Phage Display Selection and Screening from a First Library

Summary

In this Example, complement component 4 (C4), interleukin 6 (IL-6) and insulin were used as targets in phage display selections using a phage library of Y variants. Selected clones were DNA sequenced, produced in *E. coli* as soluble fractions and assayed against each respective target using ELISA and SPR. Based on sequence observations in these selected Y variants and the results described in this Example, it was concluded to subject positions 20, 21, 24, 27, 29, 30, 33, 36, 37, 40 and 44 to randomization as "binding positions" in a second library, further described in Examples 5 and 6.

Materials and Methods

Production of Library Phage Stock:

Production of phage stock was performed as follows. A glycerol stock containing the phagemid library Ylib001Naive.I in *E. coli* cells ER2738 was inoculated in 19 l of cultivation medium (2.5 g/l $(NH_4)_2SO_4$; 5.0 g/l yeast extract; 30 g/l tryptone; 2 g/l $K_2HPO_4$; 3 g/l $KH_2PO_4$; 1.25 g/l $Na_3C_6H_5O_7.2H_2O$; 0.1 ml/l Breox FMT30 antifoaming agent), supplemented with 25 μg/ml carbenicillin, 5 ml/l of 1.217 M MgSO4 and 19 ml of a trace element solution (129 mM FeC13; 37 mM $ZnSO_4$; 10.6 mM $CuSO_4$; 78 mM $MnSO_4$; 94 mM $CaCl_2$, dissolved in 1.2 M HCl). pH was maintained at 7 through the automatic addition of 25% $NH_4OH$, air was supplemented (19 l/min), and the stirrer was set to keep the dissolved oxygen level above 30%. When the cells reached an $OD_{600}$ of 0.50, the culture was infected using a 5× molar excess of M13K07 helper phage (New England Biolabs). The cells were incubated for 30 min before expression was induced by the addition of IPTG to a concentration of 100 μM. 1 h after the induction, the culture was supplemented with 25 μg/ml kanamycin, and a glucose-limited fed-batch cultivation was started where a 600 g/l glucose solution was fed to the reactor (30 g/h the first 20 h and then 90 g/h until the end of the cultivation). The culture was harvested 24 h after the addition of helper phages. The cells in the culture were removed by centrifugation (15,900 g, 50 min).

The phage particles in the supernatant were precipitated twice in PEG/NaCl (20% polyethylene glycol/2.5 M NaCl sodium chloride) using standard procedures. Phage stocks were filtered using a 0.45 μm filter, dissolved in PBS and glycerol, and stored at −80° C. before use.

Phage Display Selection of C4, IL-6 and Insulin Binding Y Variants:

C4 (Complement Technology Inc, cat. no. A105), IL-6 (R&D Systems, cat. no. 206-IL-200/CF) and insulin (Roche, cat. no. 1376497) were biotinylated as described in Example 1. The phage stock described in this Example, displaying random variants of protein Y according to the Ylib001Naive.I definition on bacteriophage, was used to select C4, IL-6 and insulin binding polypeptides. Streptavidin coated paramagnetic beads (SA beads) (Dynabeads® M-280 Streptavidin; Life Technology) were used as solid support. Before each round, except for the first round, a negative selection was performed to remove unspecific binders against SA or the beads. The phage particles were incubated with the beads for 30 min at RT and the supernatant was used as input in selection rounds. All tubes and beads were blocked with PBSTB (PBS supplemented with 0.1% Tween20 and 3% BSA (bovine serum albumin) to avoid unspecific binding.

The selection buffer consisted of PBSTB supplemented with 1.5 μM human serum albumin (Albucult, Novozymes), and selection was performed in four rounds. In round one to three, binders to each biotinylated target were selected separately as well as from a mix with equal amounts of target. In the first round, 100 nM of the respective target were used and incubated with phage particles for 2 h under rotation at RT. In rounds two and three, the target concentrations were reduced to 50 nM and 25 nM, respectively, and the incubation time was shortened to 90 min and 60 min, respectively. For round four, two separate target concentrations were used, 25 and 12.5 nM, and the phage particles were incubated with the target proteins for 60 min under rotation at RT. In round four, the output from the mixed track from round three was split and incubated with each target separately at 25 nM. To capture phage-target complexes, blocked SA beads were added and incubated for 15 min. The beads were washed with PBST 0.1% with increased stringency for each round (twice in round one, four times in round two, six times in round three and eight times in round four).

Bead-captured phage particles were eluted with 500 μl 0.1 M glycine-HCl, pH 2.2 during 10 min followed by immediate neutralization with 50 μl Tris-HCl, pH 8.0 and 450 μl PBS. Selected phage particles were amplified as described below and new phage stocks were prepared between each cycle. Phage stock, i.e. phages entering the selection cycle, and eluted phage particles were titrated after each selection cycle.

Amplification of Phage Particles Between Rounds:

*E. coli* XL1-Blue cells (Agilent technologies), cultivated to log phase in TSB supplemented with tetracycline 10 μg/ml, were infected with eluted phage particles for 30 min at 37° C. after each cycle of selection. TSB medium was added after infection to double the cultivation volume and ampicillin was added to a final concentration of 100 μg/ml. The infected bacteria were incubated for 1 h before addition of helper phage at a 10× excess compared to number of eluted phage particles used. Superinfection was allowed to take place during 1.5 h before the bacteria were pelleted in a centrifuge. Bacteria were re-suspended in TSB+YE supplemented with 100 μg/ml ampicillin, 25 ug/ml kanamycin and 0.1 mM IPTG and grown over night at 30° C. The amount of bacteria used for infection was 100× excess compared to the number of eluted phage particles. The overnight cultures were made in 100 ml for round one and 50 ml for each of rounds two and three. The overnight cultures were pelleted by centrifugation, and phage particles in the supernatant were precipitated twice with PEG/NaCl buffer. Finally, the phages were re-suspended in selection buffer before entering the next selection round. In the final selection cycle, ER2738 bacteria were used for infection and bacteria were spread on TBAB plates supplemented with 200 μg/ml ampicillin in order to form single colonies to be used in ELISA screening.

Production of Soluble Y Variants:

The Y variants were produced by inoculating single colonies from the selections into 1.2 ml TSB-YE medium supplemented with 100 μg/ml ampicillin and 1 mM IPTG in deep-well plates (Nunc). The plates were incubated with rotation for 24 h at 37° C. Cells were pelleted by centrifugation at 3300 g and re-suspended in 150 μl PBST 0.05 (PBS supplemented with 0.05% Tween20). The bacterial suspensions were heated to 82° C. during 20 min to lysate the cells. Soluble fractions of Y variants were isolated in 96 well plates by filtration using filter plates (EMD Millipore). The final supernatants contained the Y variants as fusions to Z03639, expressed as GSS-[Y#####]-ASGS-[Z03639]-YVPG (SEQ ID NO:173). Y##### refers to individual, 46 amino acid residue Y variants.

Sequencing:

In parallel with the ELISA screening, all clones were sequenced as described in Example 1.

Sequence Analysis:

Unique sequences from the selections were analyzed using an average-link hierarchical clustering method. This was done on the sequences from selections against each target separately, as well as with sequences from selection against different targets grouped together.

ELISA Screening of Y Variants:

The binding of Y variants to their respective target was analyzed in ELISA assays. Half-area 96-well ELISA plates (Greiner) were coated at 4° C. overnight with 2 μg/ml of an anti-Z03639 goat antibody (produced in-house) diluted in coating buffer (50 mM sodium carbonate, pH 9.6; Sigma). The antibody solution was poured off and the wells were washed in water and blocked with PBSC (PBS supplemented with 0.5% casein; Sigma) for 30 min at RT. The blocking solution was discarded, whereupon heated and filtered Y protein solutions, diluted 8× in PBST 0.05%, were added to the wells and incubated for 1.5 to 2.25 h at RT. As a negative control, ER2738 *E. coli* supernatants, cultivated, heat treated and filtered as described above, were added. The supernatants were poured off and the wells were washed 4 times with PBST 0.05%. Then, biotinylated target (C4 at a concentration of 50 nM, IL-6 at a concentration of 100 nM, or insulin at a concentration of 300 nM) in PBSC was added to each well. The plates were incubated for 1 h to 1.25 h at RT followed by washes as described above. Streptavidin conjugated HRP (Thermo Scientific) diluted 1:30,000 in PBSC, was added to the wells and the plates were incubated for 45 min. After washing as described above, 1-step Ultra TMB substrate (Thermo Scientific) was added to the wells and the plates were treated according to the manufacturer's recommendations. The absorbance at 450 nm was measured using an EnSpire multi-well plate reader (Perkin Elmer).

Subcloning and Protein Production of a Subset of Y Variants with a $His_6$-Tag:

A subcloning strategy was applied to a subset of ELISA positive variants, for construction of monomeric Y variant molecules as described in Example 1. Proteins were expressed and purified using an N-terminal $His_6$-tag according to methods described in Example 1. The Y variant gene fragments were subcloned into an expression vector, resulting in the encoded sequences MGSSHHHHHHGSS-[Y#####]-ASGSVD (SEQ ID NO:167).

CD and SPR Analyses of Purified Y Variants:

Produced Y variants were subjected to CD and SPR analyses according to the methods described in Example 1.

Results

Phage Display Selection of C4, IL-6 and Insulin Binding Y Variants:

Phage display selection was performed using a newly designed library (Example 2) and the target proteins C4, IL-6 and insulin. In round one to three, the library was incubated with each target separately or with a mixture including all three targets. In the fourth round, the phage stock from the mixed-target track was split and incubated with each target separately. Individual clones were obtained after three and four cycles of phage display selection.

Sequencing:

Sequencing was performed for clones obtained after three and four cycles of selection. Each variant was given a unique identification number #####, and individual variants are referred to as Y#####. Examples of amino acid sequences of the 46 amino acid residues long Y variants are listed in FIG. 1 and in the sequence listing as SEQ ID NO:1-17, SEQ ID NO:49-69 and SEQ ID NO:90-109, for the targets C4, IL-6 and insulin respectively.

Sequence Analysis:

Clustering and consensus analysis was performed for the sequences of the clones obtained from the selection, in order to identify sequence similarities among all variants, as well as target-specific similarities. Consensus analyses performed for Y variants with verified binding in ELISA to its respective target are shown in FIG. 1A-D. In the 12 most randomized positions, all binding Y variants showed a consensus in positions 30, 33, 36, 37 and 40 regardless of target, but the preferred amino acids differed depending on target. The C4-binding Y variants showed consensus towards specific amino acids in positions 24, 27 and 44, whereas the insulin-binding Y variants showed consensus in positions 24 and 44 but not in position 27.

Although positions 18, 20 and 21 in ABD are known to be important for its native binding to albumin, these positions did not show a strong consensus in the Y variants identified in the selection against the three targets used in this study. However, for the C4 and insulin binding Y variants, one third of the Y variants had the same residues in position 20 and 21, which indicates that these positions are involved in the interaction with their respective target, but not to the same extent as the residues in helix three. In the more restrictively randomized scaffold positions, V was preferred in position 17 and A was preferred in position 43, regardless of target. In position 28, a strong preference for A was observed in C4 and insulin binding Y variants, whereas G was tolerated in the IL-6 binding Y variants. In position 9, I was more frequently observed than N. In positions 15, 19, 22 and 23, no clear consensus was observed, which indicates that these positions are more tolerant to variation.

ELISA Screening of Y Variants:

The clones obtained after three or four cycles of selection were produced in 96-well plates and screened for b-C4, b-IL-6 or b-insulin binding activity in ELISA. Several unique Y variants were found to give a response of 0.15 AU or higher (corresponding to at least 2x the negative control) against b-C4 at a concentration of 50 nM or against b-IL-6 at a concentration of 100 nM, respectively. The average response of the negative controls was 0.059 AU and 0.067 AU for b-C4 and b-IL-6, respectively. The average response of the negative controls to b-insulin was 0.057 AU while the response of the selected Y variants spanned between 0.093 AU and 0.945 AU (corresponding to approximately 2× the negative control or more) at a concentration of 300 nM.

CD and SPR Analyses of Purified Y Variants:

Produced Y variants were subjected to CD and SPR analyses. The individual melting points and affinity values ($K_D$) are shown in Table 2. All variants were able to refold after thermal denaturation, but the degree of α-helical content varied (FIG. 2). Overall, the C4 binding Y variants demonstrated a high α-helical content while both the analyzed IL-6 binding Y variants showed less α-helical content. A comparison of the insulin binding Y variants Y00032 and Y00125, which only differed in position 9 with I in Y00032 and N in Y00125, showed a considerably higher α-helical content for Y00032 compared to Y00125. This confirmed the importance of position 9 for stability and I being preferred over N. This may at least partly explain the limited ability of the IL-6 binding Y variants Y00035 and Y00076, both with N in position 9, to fold into an α-helical structure. When comparing Y variants binding to the same target, a higher melting temperature correlated with a higher binding affinity.

TABLE 2

Melting points and affinity constants

| SEQ ID NO: | Y variant | Target | Tm (° C.) | $K_D$ (M) |
|---|---|---|---|---|
| 1 | Y00001 | C4 | 61 | n.a. |
| 4 | Y00004 | C4 | 45 | n.a. |
| 5 | Y00005 | C4 | 60 | n.a. |
| 6 | Y00006 | C4 | 49 | n.a. |
| 50 | Y00035 | IL-6 | 60 | $3.6 \times 10^{-7}$ |
| 61 | Y00076 | IL-6 | 47 | $4.3 \times 10^{-7}$ |
| 90 | Y00032 | Insulin | 47 | $5.0 \times 10^{-8}$ |
| 106 | Y00125 | Insulin | 35 | $1.1 \times 10^{-7}$ |

n.a. not analyzed

Example 4

Mutational Studies of C4, IL-6 and Insulin Binding Y Variants

Summary

This Example describes a set of sequential mutational studies performed in order to optimize the scaffold properties in the light of positions decided to be randomized for binding according to the results described in Example 3.

Materials and Methods

Cloning of Mutated Y Variants:

In a first mutational study, different mutations were introduced in sequence positions not varied for binding (i.e. "scaffold positions") in the Y variants, in order to evaluate the impact of these mutations on the stability and binding ability. This was performed using the Y variants Y00001 (SEQ ID NO:1) and Y00032 (SEQ ID NO:4) binding C4 and insulin, respectively, as templates. Y00032 was regarded as a suitable model molecule because while it demonstrated a good ability to fold into an α-helical structure, the moderate Tm of 47° C. should nevertheless allow for improvements. Single or double mutations were introduced in the surface-exposed scaffold positions 13, 15, 17, 18, 19, 22, 23, 26, 28, 32, 35, 39 and 43. All variants were cloned with an N-terminal $His_6$ tag, and the constructs encoded polypeptides in the format MGSSHHHHHHGSS-[Y#####] (SEQ ID NO:168).

In a second mutational study, further mutations were introduced in the variants based on the results of the first mutational study, to evaluate the impact of these mutations on primarily stability, as well as to verify the results from the first study in different Y variants. Y variants Y00262 (SEQ ID NO:18; C4 binding) and Y00032 and Y00270 (SEQ ID NO:90 and SEQ ID NO:117, respectively; insulin binding), were used as templates. Single, double or triple mutations were introduced in the surface-exposed scaffold positions 17, 18, 19, 22, 23, 26, 35, 39 and 43. All variants were cloned with an N-terminal $His_6$ tag, and constructs encoded polypeptides in the format MGSSHHHHHHGSS-[Y#####] (SEQ ID NO:168).

In a third mutational study, a mutation in scaffold position 26 was introduced in Y variants Y00289 (SEQ ID NO:26) and Y000293 (SEQ ID NO:125) binding C4 and insulin, respectively. In addition, different N-terminal and C-terminal extensions were assessed with regard to what impact they had on the stability and binding ability as well as on the expression level. All variants were cloned with an N-terminal $His_6$ tag and obtained constructs encoded polypeptides in one of the following formats MGSSHHHHHHGSS-[Y#####] (SEQ ID NO:168), MGSSHHHHHHGSS-[Y#####]-ASYGS (SEQ ID NO:169), MGSSHHHHHHGSS-[Y#####]-GYS (SEQ ID NO:170) or MGSSHHHHHHTIDEWL-[Y#####] (SEQ ID NO:171). Cloning was performed according to the methods described in Example 1.

Production and Characterization of Mutated Y Variants:

The Y variants were cloned, produced and characterized according to the general methods described in Example 1. Produced Y variants with point mutations and/or N-terminal or C-terminal extensions were subjected to CD and SPR analyses as described in Example 1.

Results

Cloning, Production and Characterization of Mutated Y Variants:

Produced Y variants in mutation study 1, 2 and 3, respectively, were subjected to CD and SPR analyses to assess the effect of the point mutations and/or additional N-terminal or C-terminal amino acids on the stability and binding ability of the Y variants. The individual melting points and affinity values ($K_D$) are shown in Tables 3-5.

In mutation study 1, five mutants improved the stability with an increase in melting temperature between 1 to 5° C. The introduction of the non-charged residue Q in positions 35 and 39 in Y00032 increased the Tm as well as the α-helical content (FIG. 3). The combination of I in position 22 and K in position 23 was confirmed to be beneficial for thermostability, as was A in position 28. All mutated variants were shown to have a helical structure and refolded reversibly after heating to 90° C. Furthermore, all mutated Y variants targeting insulin retained some ability to interact with insulin, although to different extents. Changes in the affinity generally correlated with changes in stability.

In mutation study 2, promising mutations from study 1 were verified by mutations in the C4 binding Y variant Y00262. Q in positions 35 and 39 was shown to increase the Tm both as single mutations as well as in combination. The combination Q in position 35 and Q in position 39 was verified to increase the Tm also in insulin binding variants. Furthermore, A in position 19 was verified to have a positive impact on thermostability. All mutated variants were shown to have helical structure, and refolded reversibly after heating to 90° C. Results are summarized in Table 4.

TABLE 3

Melting points and affinity constants of Y variants in mutation study 1

| SEQ ID NO: | Y variant | Y parental | Mutation/s | Target | Tm (° C.) | $K_D$ (M) |
|---|---|---|---|---|---|---|
| 1 | Y00001 | — | — | C4 | 57 | n.a. |
| 18 | Y00262 | Y00001 | S23K | C4 | 61 | n.a. |
| 90 | Y00032 | — | — | Insulin | 49 | $6.3 \times 10^{-8}$ |
| 110 | Y00263 | Y00032 | D13K | Insulin | 43 | $1.3 \times 10^{-7}$ |
| 111 | Y00264 | Y00032 | K15Y | Insulin | 48 | $6.4 \times 10^{-8}$ |
| 112 | Y00265 | Y00032 | V17I | Insulin | 47 | $1.2 \times 10^{-7}$ |
| 113 | Y00266 | Y00032 | G18S | Insulin | 50 | $5.6 \times 10^{-8}$ |
| 114 | Y00267 | Y00032 | A19E | Insulin | 48 | $5.9 \times 10^{-8}$ |

TABLE 3-continued

| Melting points and affinity constants of Y variants in mutation study 1 | | | | | | |
|---|---|---|---|---|---|---|
| SEQ ID NO: | Y variant | Y parental | Mutation/s | Target | Tm (° C.) | $K_D$ (M) |
| 115 | Y00268 | Y00032 | K22I | Insulin | 49 | $8.4 \times 10^{-8}$ |
| 116 | Y00269 | Y00032 | S23K | Insulin | 50 | $3.9 \times 10^{-7}$ |
| 117 | Y00270 | Y00032 | K22I + S23K | Insulin | 52 | $7.7 \times 10^{-8}$ |
| 118 | Y00271 | Y00032 | E26Q | Insulin | 49 | $4.7 \times 10^{-8}$ |
| 119 | Y00272 | Y00032 | A28G | Insulin | 34 | $1.1 \times 10^{-7}$ |
| 120 | Y00273 | Y00032 | E32Q | Insulin | 46 | $7.7 \times 10^{-8}$ |
| 121 | Y00274 | Y00032 | E35Q | Insulin | 53 | $5.6 \times 10^{-8}$ |
| 122 | Y00275 | Y00032 | E39Q | Insulin | 54 | $5.9 \times 10^{-8}$ |
| 123 | Y00276 | Y00032 | A43K | Insulin | 50 | $7.6 \times 10^{-8}$ |

n.a. not analyzed

TABLE 4

| Melting points and affinity constants of Y variants in mutation study 2 | | | | | | |
|---|---|---|---|---|---|---|
| SEQ ID NO: | Y variant | Y parental | Mutation/s | Target | Tm (° C.) | $K_D$ (M) |
| 18 | Y00262 | — | | C4 | 61 | n.a. |
| 19 | Y00282 | Y00262 | I17V | C4 | 61 | n.a. |
| 20 | Y00283 | Y00262 | N18S | C4 | 61 | n.a. |
| 21 | Y00284 | Y00262 | E19A | C4 | 64 | n.a. |
| 22 | Y00285 | Y00262 | I22K | C4 | 57 | n.a. |
| 23 | Y00286 | Y00262 | E26Q | C4 | 62 | n.a. |
| 24 | Y00287 | Y00262 | E35Q | C4 | 62 | n.a. |
| 25 | Y00288 | Y00262 | E39Q | C4 | 66 | n.a. |
| 26 | Y00289 | Y00262 | E35Q + E39Q | C4 | 65 | n.a. |
| 27 | Y00290 | Y00262 | E35Q + A43K | C4 | 69 | n.a. |
| 28 | Y00291 | Y00262 | E35Q + E39Q + A43K | C4 | 66 | n.a. |
| 90 | Y00032 | — | | Insulin | 49 | $6.3 \times 10^{-8}$ |
| 124 | Y00292 | Y00032 | S23K + E35Q + E39Q | Insulin | 57 | $4.5 \times 10^{-7}$ |
| 117 | Y00270 | — | | Insulin | 52 | $7.7 \times 10^{-8}$ |
| 125 | Y00293 | Y00270 | E35Q + E39Q | Insulin | 56 | $4.9 \times 10^{-7}$ |
| 126 | Y00294 | Y00270 | E35Q + A43K | Insulin | 54 | $4.9 \times 10^{-7}$ |
| 127 | Y00295 | Y00270 | E35Q + E39Q + A43K | Insulin | 52 | $5.8 \times 10^{-7}$ |

n.a. not analyzed

In mutation study 3, different N-terminal and C-terminal extensions were shown to have a slightly positive effect on the thermostability, and Y variants with C-terminal extensions showed increased expression levels. Results are summarized in Table 5.

TABLE 5

| Melting points and affinity constants of Y variants in mutation study 3 | | | | | | | | |
|---|---|---|---|---|---|---|---|---|
| SEQ ID NO: | Y variant | Y parental | Mutation | N/C terminal tag | Target | Tm (° C.) | $K_D$ (M) | Expression (mg/g pellet) |
| 128 | Y00296 | Y00293 | E26Q | $His_6$-GGS-Y##### | Insulin | 56 | $3.7 \times 10^{-8}$ | 8.9 |
| 129 | Y00296a | Y00293 | E26Q | $His_6$-GGS-Y#####-ASYGS | Insulin | 58 | $2.2 \times 10^{-8}$ | 17 |
| 130 | Y00296b | Y00293 | E26Q | $His_6$-GGS-Y#####-GYS | Insulin | 56 | $3.1 \times 10^{-8}$ | 9.2 |
| 131 | Y00296C | Y00293 | E26Q | $His_6$-GGS-TIDEWL-Y##### | Insulin | 62 | $5.1 \times 10^{-8}$ | 4.6 |
| 29 | Y00297 | Y00289 | E26Q | $His_6$-GGS-Y##### | C4 | 64 | n.a. | 23 |
| 30 | Y00297a | Y00289 | E26Q | $His_6$-GGS-Y#####-ASYGS | C4 | 65 | n.a. | 27 |
| 31 | Y00297b | Y00289 | E26Q | $His_6$-GGS-Y#####-GYS | C4 | 69 | n.a. | 33 |

n.a. not analyzed

Example 5

Design and Construction of a Second Library

Summary

In this Example, a new library with a modified scaffold was designed and created. The outcome of the selections described in Example 3 from the library Ylib001Naive.I described in Example 2, together with the mutational studies performed in Example 4, were used as basis for the design of the new library. The library contained approximately $3.1 \times 10^{10}$ individual clones.

Materials and Methods

Library Design:

A second library was designed based on the results described in Example 3 and 4. In the library, 11 amino acid positions of the Y variant molecules were randomized (positions 20, 21, 24, 27, 29, 30, 33, 36, 37, 40 and 44 with reference to e.g. SEQ ID NO:159). Four oligonucleotides, two forward and two reverse complementary, both pairs having complementary 3' ends, were generated using TRIM technology. These oligos were ordered from Ella Biotech GmbH (Martinsried, Germany).

The DNA generated by the four separate oligonucleotides was a 117 bp long oligo, encoding an amino acid sequence partially randomized from helix two to helix three of ABD, with the sequence: 5'-GAT AGC AAA GGT GTT GGT GCA 001 001 ATT AAA 001 ATT CAG 002 GCA 002 002 GTT GAG 003 GTT CAA 001 001 AAA CAG 004 ATT CTG GCG 001 CTG CCG GCG AGC GGT AGC GTC-3' (SEQ ID NO:164) where randomized codons are illustrated as 001 to 004. The different randomization strategies correspond to; 001) 18 possible amino acids, all except C and P, evenly distributed (5.6% each); 002) 19 possible amino acids, all except C, evenly distributed (5.3% each); 003) 19 possible amino acids, all except C, 50% of amino acid G and the rest evenly distributed (2.6% each); 004) 19 amino acids, all except C, 50% of amino acid A and the rest evenly distributed (2.6% each). A large number of errors are usually generated in longer oligos due to technical challenges during TRIM oligonucleotide synthesis. An overlap strategy for the oligos was therefore used, in which randomized positions 003 and 004 contained 50% of the amino acid G and A, respectively. In this way, the library could be assembled using two separate oligo pairs with a low number of errors and including all desired variable positions.

The oligos were PCR amplified to introduce flanking restriction sites SacI and SalI. The resulting theoretical library size was $7.6\times10^{13}$ variants.

Library Construction:

The phagemid vector pAY03686 was modified to contain the first part encoding amino acid residues 1 to 11 of helix one, followed by a SacI endonuclease cleavage site. The modified vector was denoted pAY04260.

The library was constructed and verified essentially as described in Example 2, with the exception of using restriction endonucleases SacI-HF and SalI-HF (New England Biolabs) to cleave the fragment and the corresponding pAY04260 vector. The ligation reactions (approximately 200 ng DNA/transformation) were electroporated into electrocompetent *E. coli* XL1-Blue cells (Lucigen).

Results

Library Design:

A second library was designed based on the findings described in Example 3 and 4. The amino acids used in the scaffold positions of the sequence and the distribution of variable amino acid residues in the binding positions were defined. A total of 11 amino acid positions were targeted for randomization, namely those corresponding to positions 20, 21, 24, 27, 29, 30, 33, 36, 37 40 and 44 in SEQ ID NO:159. The theoretical size of the designed library was $7.6\times10^{13}$ different, unique Y variants.

Library Construction:

A new phagemid vector, denoted pAY04260, was constructed for monovalent display using the M13 filamentous phage coat protein III. The newly constructed vector contained DNA encoding the first 11 amino acids of the Y variants and was used for construction of the library. The library, or population, was denoted "Ylib002Naive.I". The actual size of the library, determined by titration after transformation to *E. coli* XL1-Blue cells, was $3.1\times10^{10}$ transformants. The library quality was tested by sequencing of 192 transformants and comparing their actual sequences with the theoretical design. Sequence analysis of individual library members verified a distribution of codons in accordance with the theoretical design. A library of potential binders in a novel scaffold was thus successfully constructed.

Example 6

Phage Display Selection and Screening from a Second Library

Summary

In this Example, C4, IL-6 and insulin were used as targets in phage display selections using the second phage library of Y variants. Selected clones were DNA sequenced, produced in *E. coli* as soluble protein fractions and assayed against each respective target using ELISA and SPR.

Materials and Methods

Production of Phage Stock:

Production of phage stock was performed as follows. A glycerol stock containing the phagemid library Ylib002Naive.I in *E. coli* cells XL1 Blue was inoculated in 20 l of fermentor cultivation medium (30 g/l tryptic soy broth; 5 g/l yeast extract; 10 g/l glucose; 100 μg/ml carbenicillin; 10 μg/ml tetracycline hydrochloride). The culture was incubated at 37° C., air was supplemented (10 l/min), and the stirrer was set to keep the dissolved oxygen level above 30%. When the $OD_{600}$ had reached 0.5, 16 liter of the culture was discarded. The remaining 4 liter culture was infected using a 10× molar excess of M13K07 helper phage. 16 liter of a new cultivation medium was added (3.05 g/l $(NH_4)_2SO_4$; 6.1 g/l yeast extract; 3.66 g/l $K_2HPO_4$; 5.48 g/l $KH_2PO_4$; 2.29 g/l $Na_3C_6H_5O_7.2H_2O$), supplemented with 100 μg/ml carbenicillin, 3.2 ml/l of 1.217 M MgSO4, 0.9 ml/l of 25% $NH_4OH$, and 1 μl/ml of a trace element solution (194 mM FeCl3; 55 mM $ZnSO_4$; 10.6 mM $CuSO_4$; 62 mM $MnSO_4$; 47 mM $CaCl_2$), dissolved in 1.2 M HCl), 0.2 mM thiamine, and 0.65 μl/ml of a vitamin solution (2.1 mM pantothenic acid; 3.6 mM choline chloride; 1.1 mM folic acid; 5.5 mM myo-inositol; 4.1 mM niacinamide; 0.13 mM riboflavin; 1.5 mM thiamine). After 60 min incubation, kanamycin was added to a concentration of 50 μg/ml and expression was induced by the addition of IPTG to a concentration of 100 μM. The cultivation temperature was lowered to 30° C. and 0.15 ml/l antifoam agent (Breox FMT 30) was added. pH was maintained at 7 through the automatic addition of % $NH_4OH$, and a glucose-limited fed-batch cultivation was started where a 600 g/l glucose solution was fed to the reactor (15 g/h the first 20 h and then 75 g/h until the end of the cultivation). The culture was harvested 22 h after the addition of helper phage particles. The cells in the culture were removed by centrifugation (15,900 g, 50 min). The phage particles in the supernatant were precipitated twice in PEG/NaCl using standard procedures. Phage stocks were filtered using a 0.45 μm filter, dissolved in PBS and glycerol, and stored at −80° C. before use.

Phage Display Selection of C4, IL-6 and Insulin Binding Y Variants from Ylib002Naive.I:

C4 (Lee Biosolutions Inc, cat. no. 194-41), IL-6 (R&D Systems, cat. no. 206-IL-200/CF) and insulin (Roche, cat. no. 1376497) were biotinylated as described in Example 1. The phage stock described in this Example, displaying random variants of the library sequence on bacteriophage, was used to select C4, IL-6 and insulin binding polypeptides. Selection was performed essentially as described in Example 3 with the following exceptions. Selections were performed with targets separately only (no mix). Four rounds were used for insulin while five rounds were used for each of C4 and IL-6. Target concentrations and washing steps were performed according to Table 6.

Selected and eluted phage particles were amplified as described below and new phage stocks were prepared between each cycle. Phage stock, i.e. phage particles entering the selection cycle, and eluted phage particles were titrated after each selection cycle.

TABLE 6

Overview of the selections against C4, IL-6 and insulin using the Ylib002Naive.I library

| Cycle | Selection track | Phage stock from library or selection track | Target protein | Target conc. (nM) | Number of washes | Number of overnight washes |
|---|---|---|---|---|---|---|
| 1 | 1 | Ylib002Naive.I | b-C4 | 100 | 2 | |
| 1 | 2 | Ylib002Naive.I | b-IL-6 | 100 | 2 | |

TABLE 6-continued

| Overview of the selections against C4, IL-6 and insulin using the Ylib002Naive.I library | | | | | | |
|---|---|---|---|---|---|---|
| Cycle | Selection track | Phage stock from library or selection track | Target protein | Target conc. (nM) | Number of washes | Number of overnight washes |
| 1 | 3 | Ylib002Naive.I | b-insulin | 100 | 2 | |
| 2 | 1-1 | 1 | b-C4 | 50 | 4 | |
| 2 | 2-1 | 2 | b-IL-6 | 50 | 4 | |
| 2 | 3-1 | 3 | b-insulin | 50 | 4 | |
| 3 | 1-1-1 | 1-1 | b-C4 | 10 | 8 | |
| 3 | 2-1-1 | 2-1 | b-IL-6 | 10 | 8 | |
| 3 | 3-1-1 | 3-1 | b-insulin | 10 | 8 | |
| 4 | 1-1-1-1 | 1-1-1 | b-C4 | 1 | 12 | |
| 4 | 1-1-1-2 | 1-1-1 | b-C4 | 1 | 11 | 1 |
| 4 | 1-1-1-3 | 1-1-1 | b-C4 | 5 | 12 | |
| 4 | 1-1-1-4 | 1-1-1 | b-C4 | 5 | 11 | 1 |
| 4 | 1-1-1-5 | 1-1-1 | b-C4 | 2.5 | 12 | |
| 4 | 1-1-1-6 | 1-1-1 | b-C4 | 2.5 | 11 | 1 |
| 4 | 2-1-1-1 | 2-1-1 | b-IL-6 | 1 | 12 | |
| 4 | 2-1-1-2 | 2-1-1 | b-IL-6 | 1 | 11 | 1 |
| 4 | 2-1-1-3 | 2-1-1 | b-IL-6 | 5 | 12 | |
| 4 | 2-1-1-4 | 2-1-1 | b-IL-6 | 5 | 11 | 1 |
| 4 | 2-1-1-5 | 2-1-1 | b-IL-6 | 2.5 | 12 | |
| 4 | 2-1-1-6 | 2-1-1 | b-IL-6 | 2.5 | 11 | 1 |
| 4 | 1-1-1-1 | 1-1-1 | b-insulin | 5 | 12 | |
| 4 | 1-1-1-2 | 1-1-1 | b-insulin | 1 | 12 | |
| 4 | 1-1-1-3 | 1-1-1 | b-insulin | 1 | 11 | 1 |
| 5 | 1-1-1-3-1 | 1-1-1-3 | b-C4 | 1 | 12 | |
| 5 | 1-1-1-3-2 | 1-1-1-3 | b-C4 | 1 | 11 | 1 |
| 5 | 2-1-1-3-1 | 2-1-1-3 | b-IL-6 | 1 | 12 | |
| 5 | 2-1-1-3-2 | 2-1-1-3 | b-IL-6 | 1 | 11 | 1 |

Amplification of Phage Particles Between Rounds:

Amplification of phage particles between rounds was performed as described in Example 3 with the exception that carbenicillin was used at a concentration of 100 μg/ml instead of ampicillin during cultivations. The amount of bacteria used for infection was approximately 100-200× excess compared to the number of eluted phage particles. In selection cycle four (all targets) and selection cycle five (C4 and IL-6), ER2738 bacteria (C4) or XL1-Blue (IL-6 and insulin) were used for infection and bacteria were spread on TBAB plates supplemented with 200 μg/ml ampicillin in order to form single colonies to be used in ELISA screening.

Production of Soluble Y Variants Supernatants and Sequencing:

The Y variants were produced as soluble proteins as described in Example 3. In parallel with the ELISA screening, all clones were sequenced as described in Example 1

Screening of Y Variants Using ELISA and SPR:

The binding of Y variants to IL-6 and insulin, respectively, was analyzed in ELISA assays as described in Example 3 and using 300 nM IL-6 or insulin.

Produced Y variants from the C4 and insulin selections were screened for target binding using a Biacore 8K instrument (GE Healthcare). Anti-Z03639 goat antibody was immobilized by amine coupling onto the carboxylated dextran layer on surfaces of CM-5 chips to levels of 14500-17500 RU. Prepared supernatants were diluted 10× in HBS-EP+ and injected at a flow rate of 10 μl/min for 5 min, followed by injection of a single concentration of target proteins (50 nM of C4 and 300 nM of insulin) for 5 min. The dissociation of targets was monitored for 7 min and the surfaces were thereafter regenerated with two injections of 30 μl glycine-HCl pH 2.5. Before performing the kinetic analyses, the signal from target injected over a reference surface containing goat anti-Z but no Y sample was subtracted from the sensorgrams of Y####-Z03639 binding to target. Target-binding analyses were performed using the Biacore 8K Evaluation Software. Binding clones showing the slowest off-rate were chosen for further analysis.

Subcloning and Protein Production of a Subset of Y Variants with a $His_6$-Tag:

A subcloning strategy was applied on a subset of ELISA and/or SPR positive variants for construction of monomeric Y variant molecules according to the methods described in Example 1. Proteins were expressed and purified using an N-terminal $His_6$-tag according to the methods described in Example 1. The Y variant gene fragments were subcloned into an expression vector, resulting in the encoded sequences MGSSHHHHHHGSS-[Y#####]-A (SEQ ID NO:172).

CD and SPR Analyses of Cloned and Purified Y Variants:

Produced Y variants were subjected to CD and SPR analyses according to the methods described in Example 1. In addition, CD spectra of selected IL-6 binding variants were also recorded at 60, 70, 80 and 90° C.

Results

Phage Display Selection of C4, IL-6 and Insulin Binding Y Variants from Ylib002Naive.I:

Phage display selection was performed with a newly designed library (Example 5) against the target proteins C4, IL-6 and insulin. Individual clones were obtained after four and five cycles of phage display selection.

Sequencing:

Sequencing was performed for clones obtained after four and five cycles of selection. Each variant was given a unique identification number #####, and individual variants are referred to as Y#####. The amino acid sequences of the Y variants are listed in FIG. 1 and in the sequence listing as SEQ ID NO:32-39, SEQ ID NO:70-80 and SEQ ID NO:132-145 for the targets C4, IL-6 and insulin, respectively.

Screening of Y Variants Using ELISA and SPR:

The clones obtained after four or five cycles of selection were produced in 96-well plates as soluble proteins. Y variants were screened for b-IL-6 or b-insulin binding activity in ELISA. Several unique Y variants were found to give a response corresponding to approximately 2× the negative control or more against b-IL-6 or b-insulin at a concentration of 300 nM, respectively. The average response of the negative controls was 0.083 AU and 0.054 AU for b-IL-6 and insulin, respectively.

A selection of C4 and insulin binding Y variants was submitted to a kinetic screening using Biacore 8K as described in Example 1. A single concentration of C4 (50 nM) or insulin (300 nM) was injected over each Y#####-Z03639 captured from soluble extracts on a sensor chip surface containing an anti-Z03639 antibody. Y variants having a positive response in ELISA or showing the slowest off rate curves in SPR analysis were chosen for subcloning.

Figure 4G:
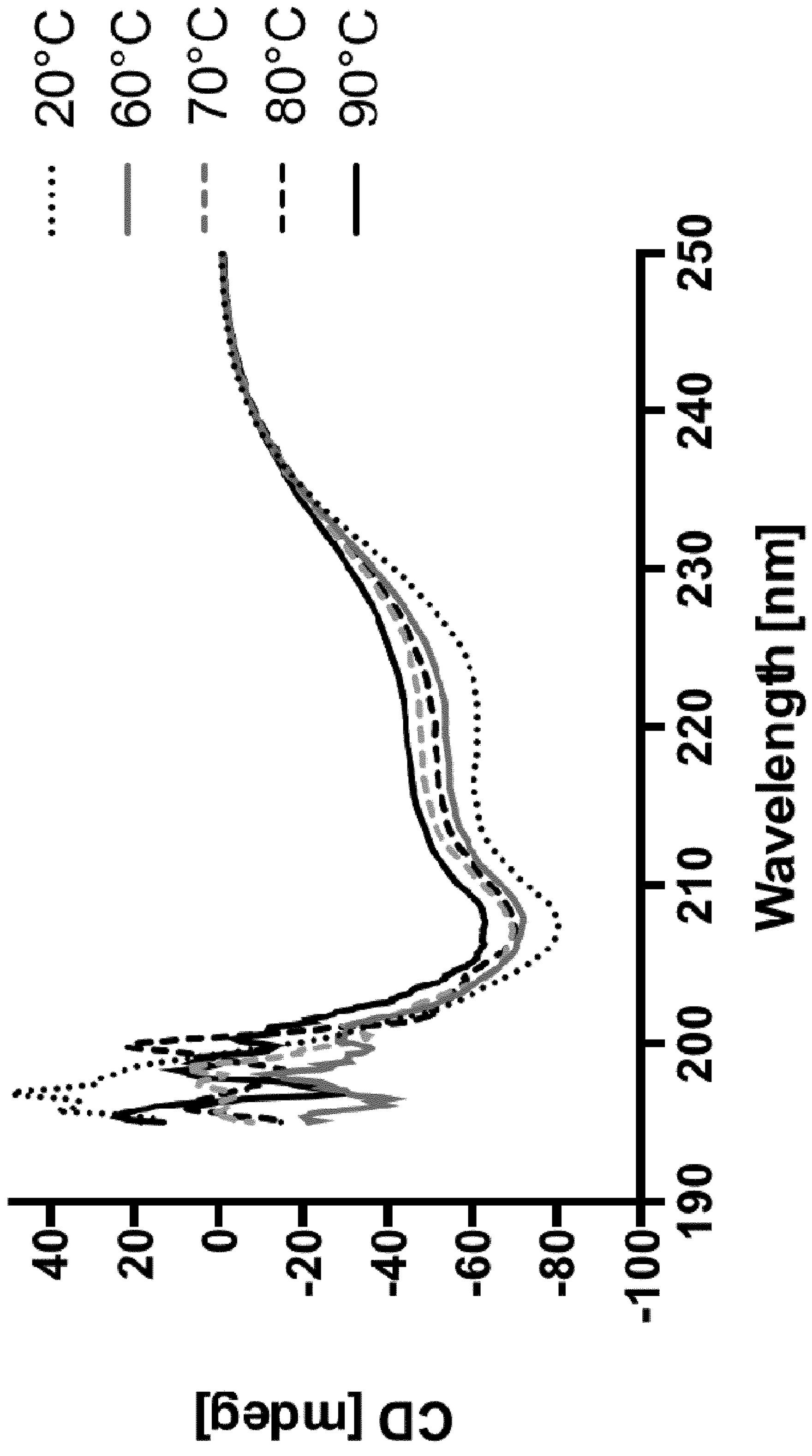
FIG. 4G shows that partial structure of the IL-6 binding variant Y02444 is observed up to 90° C.

CD and SPR Analyses of Purified Y Variants:

Produced Y variants were subjected to CD and SPR analyses. Calculated kinetic parameters, affinities and Tm values as well as the estimated percentage of protein expressed as soluble product are presented in Table 7. Examples of melting curves as well as CD spectra recorded before and after the VTM are illustrated in FIG. 4 for the C4 binding Y variant Y00792 (FIG. 4A-B), the insulin binding variant Y00301 (FIG. 4C-D) and the IL-6 binding variant Y02444 (FIG. 4E-F). For the IL-6 binding variants, a reliable Tm could not be determined as these variants appear not to fully unfold, but showed partial structure also at temperatures up to 90° C., as is illustrated for Y02444 in FIG. 4G.

TABLE 7

Expression data, calculated kinetic parameters, $K_D$ and Tm values

| SEQ ID NO | Y variant | Target | Expression (mg/g pellet) | Estimated soluble fraction (%) | $k_a$ (1/Ms) | $k_d$ (1/s) | $K_D$ (M) | Tm (° C.) |
|---|---|---|---|---|---|---|---|---|
| 32 | Y00792 | C4 | 30 | 100 | $2.7 \times 10^4$ | $1.7 \times 10^{-3}$ | $6.2 \times 10^{-8}$ | 58 |
| 34 | Y02303 | C4 | 3.3 | 100 | $9.6 \times 10^4$ | $2.1 \times 10^{-1}$ | $2.2 \times 10^{-6}$ | 43 |
| 35 | Y02309 | C4 | 24 | 100 | $3.6 \times 10^4$ | $2.5 \times 10^{-3}$ | $7.0 \times 10^{-8}$ | 56 |
| 36 | Y02310 | C4 | 15 | 100 | n.a. | n.a. | n.a. | 56 |
| 37 | Y02330 | C4 | 17 | 100 | $9.6 \times 10^4$ | $4.6 \times 10^{-3}$ | $4.8 \times 10^{-8}$ | 49 |
| 38 | Y02337 | C4 | 6.1 | 100 | $4.2 \times 10^5$ | $8.1 \times 10^{-1}$ | $1.9 \times 10^{-6}$ | 31 |
| 39 | Y02358 | C4 | 28 | 100 | $9.0 \times 10^4$ | $1.4 \times 10^{-3}$ | $1.6 \times 10^{-8}$ | 51 |
| 72 | Y02374 | IL-6 | 21 | 100 | $1.4 \times 10^4$ | $1.7 \times 10^{-3}$ | $1.2 \times 10^{-7}$ | n.d.* |
| 74 | Y02415 | IL-6 | 19 | 100 | $9.7 \times 10^3$ | $1.5 \times 10^{-3}$ | $1.6 \times 10^{-7}$ | n.d.* |
| 75 | Y02444 | IL-6 | 25 | 100 | $9.0 \times 10^4$ | $5.5 \times 10^{-3}$ | $6.1 \times 10^{-8}$ | n.d.* |
| 76 | Y02447 | IL-6 | 22 | 100 | $1.1 \times 10^4$ | $1.7 \times 10^{-3}$ | $1.6 \times 10^{-7}$ | n.d.* |
| 78 | Y02465 | IL-6 | 12 | 100 | $7.5 \times 10^3$ | $2.1 \times 10^{-3}$ | $2.7 \times 10^{-7}$ | n.d.* |
| 79 | Y02495 | IL-6 | 18 | 100 | $7.1 \times 10^3$ | $1.7 \times 10^{-3}$ | $2.4 \times 10^{-7}$ | n.d.* |
| 132 | Y00299 | Insulin | 34 | 75 | $3.1 \times 10^5$ | $2.0 \times 10^{-3}$ | $6.5 \times 10^{-9}$ | 56 |
| 133 | Y00301 | Insulin | 24 | 83 | $2.9 \times 10^7$ | $5.6 \times 10^{-2}$ | $9.4 \times 10^{-10}$ | 62 |
| 134 | Y00304 | Insulin | 20 | 33 | $8.5 \times 10^4$ | $1.1 \times 10^{-3}$ | $2.1 \times 10^{-8}$ | 41 |
| 135 | Y00310 | Insulin | 31 | 86 | $1.7 \times 10^5$ | $6.3 \times 10^{-3}$ | $3.7 \times 10^{-8}$ | 54 |
| 136 | Y00330 | Insulin | 6.8 | 67 | $3.0 \times 10^4$ | $3.7 \times 10^{-3}$ | $1.2 \times 10^{-7}$ | 56 |
| 138 | Y00345 | Insulin | 18 | 80 | $2.9 \times 10^5$ | $1.7 \times 10^{-2}$ | $6.1 \times 10^{-8}$ | 53 |
| 141 | Y00356a | Insulin | 15.0 | 60 | $3.4 \times 10^7$ | $6.1 \times 10^{-3}$ | $1.7 \times 10^{-10}$ | 56 |
| 142 | Y00358 | Insulin | 22 | 97 | $2.2 \times 10^5$ | $2.3 \times 10^{-3}$ | $1.0 \times 10^{-8}$ | 61 |
| 144 | Y00361 | Insulin | 6.3 | 100 | $1.2 \times 10^4$ | $3.6 \times 10^{-3}$ | $3.1 \times 10^{-7}$ | 52 |

n.a. not analyzed n.d. not determinable

*Tm not determinable due to small differences in CD amplitude upon temperature increase as partial structure is observed also at 90° C.

Example 7

Mutational Studies of C4, IL-6 and Insulin Binding Y Variants from the Second Library Summary This Example describes a set of two additional sequential mutational studies performed in order to further optimize the properties of the population sequence, primarily in terms of high production yields and high solubility, while maintaining a high thermostability and binding ability over a broad range of Y variants.

Materials and Methods

Cloning of Mutated Y Variants:

In a fourth mutational study, different mutations were introduced in Y variants, to evaluate the impact of these mutations on protein expression. This was performed using the insulin binding Y variant Y00356 (SEQ ID NO:140) as template. The mutations were introduced in the scaffold positions 9 ($X_{sc1}$), 15 ($X_{sc3}$), and 26 ($X_{sc4}$), and more precisely the mutations I9L, K15Y and Q26E. All variants were cloned with an N-terminal $His_6$ tag and the genetic constructs obtained encoded polypeptides in the format MGSSHHHHHHGSS-[Y#####] (SEQ ID NO:168). Cloning was done according to the methods described in Example 1.

In a fifth mutational study, the mutations I9L, K15Y and Q26E were further evaluated with respect to their potential impact on protein expression and stability using additional Y variants. The mutations K15Y and Q26E were also assessed in combination. Retaining a tyrosine at position 15 would guarantee the presence of an aromatic residue, which would be convenient in the analysis of selected binding polypeptides that happen to lack aromatic residues in the target binding positions. The study was performed using the C4 binding Y variants Y00792 (SEQ ID NO:32), Y02309 (SEQ ID NO:35) and Y02330 (SEQ ID NO:37), the IL-6 binding Y variants Y02374 (SEQ ID NO:72), Y02415 (SEQ ID NO:74) and Y002444 (SEQ ID NO:75) and the insulin binding Y variants Y00301 (SEQ ID NO:133), Y00310 (SEQ ID NO:135) and Y00358 (SEQ ID NO:142) as templates. All variants were cloned with an N-terminal $His_6$ tag and the genetic constructs obtained encoded polypeptides in the format MGSSHHHHHHGSS-[Y#####]-A (SEQ ID NO:172). Cloning was done according to the methods described in Example 1.

Production and Characterization of Mutated Y Variants:

The Y variants were cloned, produced and characterized according to the general methods described in Example 1. Produced Y variants with point mutations were subjected to CD and SPR analyses as described in Example 1. In addition, CD spectra of the IL-6 binding variants were also recorded at 60, 70, 80 and 90° C.

Results

Production and Characterization of Mutated Y Variants:

Produced Y variants from mutation studies 4 and 5 were subjected to SPR and/or CD analyses to assess the effect of the different point mutations on stability and binding ability of the Y variants. Furthermore, protein expression levels and fraction of soluble product were monitored. The expression levels, solubility, melting points, kinetic parameters and affinity values ($K_D$) for the respective Y variant analyzed are summarized in Table 8 and 9, for the fourth and fifth mutational study, respectively.

In the fourth mutational study, the mutations K15Y and Q26E were each shown to almost double the expression levels, whereas the mutation I9L increased solubility during expression.

TABLE 8

Expression data and melting points of Y variants in mutation study 4

| SEQ ID NO: | Y variant | Y parental | Mutation | Target | Expression (mg/g pellet) | Estimated soluble fraction (%) | Tm (° C.) |
|---|---|---|---|---|---|---|---|
| 140 | Y00356 | — | | Insulin | 22 | 43 | 57 |
| 146 | Y02674 | Y00356 | K15Y | Insulin | 42 | 40 | 55 |
| 147 | Y02676 | Y00356 | Q26E | Insulin | 42 | 55 | 56 |
| 148 | Y02683 | Y00356 | I9L | Insulin | 20 | 92 | n.a. |

n.a. not analyzed

In the fifth mutational study, single and double mutated Y variants were successfully expressed as soluble proteins, but the expression levels varied. All variants refolded reversibly after heating to 90° C. The IL-6 binding variants showed partial structure also at 90° C. I in position 9 was shown to be preferred over L. The preference of K versus Y in position 15 and Q versus E in position 26 varied depending on the Y variant.

TABLE 9

Expression data, calculated kinetic parameters, $K_D$ and Tm values of Y variants in mutation study 5

| SEQ ID NO: | Y variant | Y parental | Mutation(s) | Target | Expression (mg/g pellet) | Est soluble fraction (%) | $k_a$ (1/Ms) | $k_d$ (1/s) | $K_D$ (M) | Tm (° C.) |
|---|---|---|---|---|---|---|---|---|---|---|
| 40 | Y02685 | Y00792 | I9L | C4 | 18 | 100 | n.a. | n.a. | n.a. | 53 |
| 41 | Y02686 | Y00792 | K15Y | C4 | 22 | 100 | n.a. | n.a. | n.a. | 59 |
| 42 | Y02687 | Y00792 | Q26E | C4 | 41 | 100 | n.a. | n.a. | n.a. | 57 |
| 43 | Y02688 | Y02330 | I9L | C4 | 5.8 | 100 | n.a. | n.a. | n.a. | 50 |
| 44 | Y02689 | Y02330 | K15Y | C4 | 13 | 100 | n.a. | n.a. | n.a. | 53 |
| 45 | Y02690 | Y02330 | Q26E | C4 | 13 | 100 | n.a. | n.a. | n.a. | 53 |
| 46 | Y02691 | Y00792 | K15Y Q26E | C4 | 25 | 100 | n.a. | n.a. | n.a. | 58 |
| 47 | Y02692 | Y02309 | K15Y Q26E | C4 | 27 | 100 | n.a. | n.a. | n.a. | 57 |
| 48 | Y02693 | Y02330 | K15Y Q26E | C4 | 19 | 100 | n.a. | n.a. | n.a. | 52 |
| 81 | Y02697 | Y02444 | I9L | IL-6 | 23 | 100 | $5.0 \times 10^{4}$ | $9.0 \times 10^{-3}$ | $1.5 \times 10^{-7}$ | n.d.* |
| 82 | Y02698 | Y02444 | K15Y | IL-6 | 12 | 100 | $2.8 \times 10^{4}$ | $3.3 \times 10^{-3}$ | $1.2 \times 10^{-7}$ | n.d.* |
| 83 | Y02699 | Y02444 | Q26E | IL-6 | 26 | 100 | $1.9 \times 10^{4}$ | $2.9 \times 10^{-3}$ | $2.0 \times 10^{-7}$ | n.d.* |
| 84 | Y02700 | Y02415 | I9L | IL-6 | 22 | 100 | $4.6 \times 10^{4}$ | $2.5 \times 10^{-3}$ | $6.2 \times 10^{-8}$ | n.d.* |
| 85 | Y02701 | Y02415 | K15Y | IL-6 | 23 | 100 | $2.1 \times 10^{4}$ | $3.6 \times 10^{-3}$ | $2.1 \times 10^{-7}$ | n.d.* |
| 86 | Y02702 | Y02415 | Q26E | IL-6 | 14 | 100 | $1.6 \times 10^{4}$ | $7.0 \times 10^{-3}$ | $4.4 \times 10^{-7}$ | n.d.* |
| 87 | Y02703 | Y02444 | K15Y Q26E | IL-6 | 21 | 100 | $2.1 \times 10^{4}$ | $2.5 \times 10^{-3}$ | $1.2 \times 10^{-7}$ | n.d.* |
| 149 | Y02709 | Y00358 | I9L | Insulin | 25 | 100 | $2.7 \times 10^{4}$ | $1.0 \times 10^{-2}$ | $3.8 \times 10^{-7}$ | 54 |
| 150 | Y02710 | Y00358 | K15Y | Insulin | 33 | 100 | $1.9 \times 10^{5}$ | $2.7 \times 10^{-3}$ | $1.4 \times 10^{-8}$ | 61 |

TABLE 9-continued

Expression data, calculated kinetic parameters, $K_D$ and Tm values of Y variants in mutation study 5

| SEQ ID NO: | Y variant | Y parental | Mutation(s) | Target | Expression (mg/g pellet) | Est soluble fraction (%) | $k_a$ (1/Ms) | $k_d$ (1/s) | $K_D$ (M) | Tm (° C.) |
|---|---|---|---|---|---|---|---|---|---|---|
| 151 | Y02711 | Y00358 | Q26E | Insulin | 34 | 100 | $1.5 \times 10^3$ | $8.0 \times 10^{-3}$ | $5.4 \times 10^{-8}$ | 62 |
| 153 | Y02713 | Y00310 | K15Y | Insulin | 30 | 100 | $1.1 \times 10^5$ | $1.4 \times 10^{-2}$ | $1.9 \times 10^{-7}$ | 51 |
| 154 | Y02714 | Y00310 | Q26E | Insulin | 14 | 100 | $2.9 \times 10^5$ | $1.6 \times 10^{-1}$ | $5.4 \times 10^{-7}$ | 53 |
| 155 | Y02715 | Y00358 | K15Y Q26E | Insulin | 27 | 100 | $6.7 \times 10^3$ | $1.9 \times 10^{-3}$ | $2.8 \times 10^{-7}$ | 61 |
| 156 | Y02716 | Y00301 | K15Y Q26E | Insulin | 6.8 | 100 | $2.7 \times 10^7$ | $2.1 \times 10^{-1}$ | $7.6 \times 10^{-9}$ | 58 |
| 157 | Y02717 | Y00310 | K15Y Q26E | Insulin | 3.6 | 100 | $3.3 \times 10^4$ | $2.0 \times 10^{-2}$ | $6.1 \times 10^{-7}$ | 52 |

n.a. not analyzed
n.d. not determinable
*Tm not determinable due to small differences in CD amplitude upon temperature increase as partial structure is observed also at 90° C.

Example 8

Generation and Analysis of Y Variants Fused to an Albumin Binding Domain

Summary

This Example describes the cloning and production of Y variants in fusion with an albumin binding domain, advantageous for extending the in vivo half-life of Y variants.

Materials and Methods

Cloning of Y Variants in Fusion with PP013:

Cloning was performed using methods known in the art. In brief, DNA encoding Y variants and the ABD variant PP013 were ordered as fragment genes from Twist Bioscience and restricted using the enzymes NdeI and NotI-HF (New England Biolabs). An expression vector (with T7 promoter) was prepared and digested with the same restriction enzymes. Ligation, transformation and sequencing were performed as described in Example 1. The constructs encoded by the expression vector were GSS-[Y#####]-G4S-PP013 or GSS-PP013-G4S-[Y#####]. One example of each construct is listed in the sequence listing as SEQ ID NO:161 and SEQ ID NO:162, respectively.

Production of Y Variants in Fusion with PP013:

Expression of the fusion proteins was performed essentially as described in Example 1. Cell pellets containing the expressed protein are re-suspended in TST-buffer (25 mM Tris-HCl, 1 mM EDTA, 200 mM NaCl, 0.05% Tween20, pH 8.0) and the cells subjected to lysis. Clarified supernatants are applied to agarose immobilized with an anti-PP013 ligand (as described in WO2014/064237). After washing with TST-buffer and 5 mM $NH_4Ac$ pH 5.5 buffer, the PP013 fused Y variants are eluted with 0.1 M HAc. Further purification may be performed using RPC-HPLC. The correct identity of the respective purified protein is confirmed using SDS-PAGE and LC/MS analysis.

Binding Analysis:

Verification of binding to the target protein of the Y variant moiety of the fusion protein, as well as binding to albumin by the albumin binding moiety, is carried out by performing Biacore analyses essentially as described in Example 1.

Pharmacokinetic Analysis:

The serum half-lives of PP013-fused Y variants are investigated in mice. The respective fusion protein are administered intravenously (i.v.) to NMRI mice (Charles River) at a dose of ~100 nmol/kg body weight. Sera from groups of three mice are obtained at 0.08, 6, 18, 78, 120, 168 and 240 hours after administration. The concentration of respective fusion protein is determined by ELISA.

Results

The results of the binding analyses are expected to show binding both to the target of the Y variant and to albumin. Furthermore, the fusion to PP013 and other albumin binding domain variants is expected to result in extended in vivo half-life.

Itemized Listing of Embodiments

1. A population of polypeptide variants based on a common scaffold, each polypeptide in the population comprising the scaffold amino acid sequence (SEQ ID NO: 165)
$X_{sc1}$AELD$X_{sc2}X_{sc3}$GVG AXXIKXIX$_{sc4}$XA XXVEXVQXXK QXI LAX wherein, independently of one another, $X_{sc1}$ is a scaffold amino acid residue selected from I and L;

$X_{sc2}$ is a scaffold amino acid residue selected from C and S;

$X_{sc3}$ is a scaffold amino acid residue selected from K and Y;

$X_{sc4}$ is a scaffold amino acid residue selected from E and Q; and each X individually is a binding amino acid residue corresponding to any amino acid residue.

2. A population according to item 1, in which each polypeptide comprises the scaffold amino acid sequence (SEQ ID NO: 166)
LAEAKEAAX$_{sc1}$A ELD$X_{sc2}X_{sc3}$GVGAX XIKXIX$_{sc4}$XAXX VEX VQXXKQX ILAXLP wherein $X_{sc1}$, $X_{sc2}$, $X_{sc3}$, $X_{sc4}$ and each individual X are as defined in item 1.

3. A population according to any preceding item, in which $X_{sc1}$ is I.

4. A population according to any preceding item, in which $X_{sc1}$ is L.

5. A population according to any preceding item, in which $X_{sc2}$ is S.

6. A population according to any preceding item, in which $X_{sc2}$ is C.

7. A population according to any preceding item, in which $X_{sc3}$ is K.

8. A population according to any preceding item, in which $X_{sc3}$ is Y.

9. A population according to any preceding item, in which $X_{sc4}$ is Q.

10. A population according to any preceding item, in which $X_{sc4}$ is E.

11. A population according to any preceding item, which comprises at least $1\times10^4$ unique polypeptide molecules.

12. A population according to item 11, which comprises at least $1\times10^6$ unique polypeptide molecules.

13. A population according to item 12, which comprises at least $1\times10^8$ unique polypeptide molecules.

14. A population according to item 13, which comprises at least $1\times10^{10}$ unique polypeptide molecules.

15. A population according to item 14, which comprises at least $1\times10^{12}$ unique polypeptide molecules.

16. A population according to item 15, which comprises at least $1\times10^{14}$ unique polypeptide molecules.

17. A population according to item 16, which comprises at least $1\times10^{15}$ unique polypeptide molecules.

18. A population of polynucleotides, characterized in that each member thereof encodes a member of a population of polypeptides according to any one of items 1-17.

19. A combination of a polypeptide population according to any one of items 1-17 with a polynucleotide population according to item 18, wherein each member of said population of polypeptides is physically or spatially associated with the polynucleotide encoding that member via means for genotype-phenotype coupling.

20. A combination according to item 19, wherein said means for genotype-phenotype coupling comprises a phage display system.

21. A combination according to item 19, wherein said means for genotype-phenotype coupling comprises a cell surface selection display system.

22. A combination according to item 21, wherein said cell surface display system comprises prokaryotic cells.

23. A combination according to item 22, wherein said prokaryotic cells are $Gram^+$ cells.

24. A combination according to item 21, wherein said cell surface display system comprises eukaryotic cells.

25. A combination according to item 24, wherein said eukaryotic cells are yeast cells.

26. A combination according to item 19, wherein said means for genotype-phenotype coupling comprises a cell-free display system.

27. A combination according to item 26, wherein said cell free display system comprises a ribosome display system.

28. A combination according to item 26, wherein said cell free display system comprises an in vitro compartmentalization display system.

29. A combination according to item 26, wherein said cell free display system comprises a system for cis display.

30. A combination according to item 26, wherein cell free display system comprises a microbead display system.

31. A combination according to item 19, wherein said means for genotype-phenotype coupling comprises a non-display system.

32. A combination according to item 31, wherein said non-display system is protein-fragment complementation assay.

33. A method for selecting a desired polypeptide having an affinity for a predetermined target from a population of polypeptides, comprising the steps:

(a) providing a population of polypeptides according to any one of items 1-17;

(b) bringing the population of polypeptides into contact with the predetermined target under conditions that enable specific interaction between the target and at least one desired polypeptide having an affinity for the target; and (c) selecting, on the basis of said specific interaction, the at least one desired polypeptide from the remaining population of polypeptides.

34. A method according to item 33, wherein step (a) comprises the preparatory steps of providing a population of polynucleotides according to item 18 and expressing said population of polynucleotides to yield said population of polypeptides.

35. A method according to item 34, wherein each member of said population of polypeptides is physically or spatially associated with the polynucleotide encoding that member via means for genotype-phenotype coupling.

36. A method according to item 35, wherein said means for genotype-phenotype coupling is as defined in any one of items 20-32.

37. A method for isolating a polynucleotide encoding a desired polypeptide having an affinity for a predetermined target, comprising the steps:

selecting said desired polypeptide and the polynucleotide encoding it from a population of polypeptides using the method according to item 35; and isolating the thus separated polynucleotide encoding the desired polypeptide.

38. A method for identifying a desired polypeptide having an affinity for a predetermined target, comprising the steps:

isolating a polynucleotide encoding said desired polypeptide using the method according to item 37; and sequencing the polynucleotide to establish by deduction the amino acid sequence of said desired polypeptide.

39. A method for selecting and identifying a desired polypeptide having an affinity for a predetermined target from a population of polypeptides, comprising the steps:

(a) synthesizing each member of a population of polypeptides according to any one of items 1-17 on a separate carrier or bead;

(b) selecting or enriching the carriers or beads based on the interaction of the polypeptide with the predetermined target; and (c) identifying the polypeptide by protein characterization methodology.

40. A method according to item 39, wherein the protein characterization methodology used in step (c) is mass spectrometric analysis.

41. A method for production of a desired polypeptide having an affinity for a predetermined target, comprising the steps:

isolating and identifying a desired polypeptide using the method according to item 38 or selecting and identifying a desired polypeptide using the method according to item 39 or 40; and producing said desired polypeptide.

42. A method according to item 41, wherein said production is carried out using chemical synthesis of the desired polypeptide de novo.

43. A method according to item 41, wherein said production is carried out using recombinant expression of a polynucleotide encoding the desired polypeptide.

44. A method for production of a desired polypeptide having an affinity for a predetermined target, comprising the steps:

(a1) isolating a polynucleotide encoding said desired polypeptide using the method according to item 37; or (a2) backtranslating a polypeptide identified using the selection and identification method according to item 39 or 40; and (b), following either (a1) or (a2), expressing the thus isolated polynucleotide to produce said desired polypeptide.

45. Polypeptide comprising an amino acid sequence which is at least 97% identical to (SEQ ID NO: 165)

$X_1AELDX_6X_7GVG\ AX_{12}X_{13}IKX_{16}IX_{18}X_{19}A\ X_{21}X_{22}VEX_{25}VQX_{28}$ $X_{29}K\ QX_{32}ILAX_{36}$ wherein, independently of one another, $X_1$ is selected from I and L;

$X_6$ is selected from C and S;

$X_7$ is selected from K and Y;

$X_{18}$ is selected from E and Q; and each of $X_{12}$, $X_{13}$, $X_{16}$, $X_{19}$, $X_{21}$, $X_{22}$, $X_{25}$, $X_{28}$, $X_{29}$, $X_{32}$ and $X_{36}$ is any amino acid residue.

46. Polypeptide according to item 45, which comprises an amino acid sequence which is at least 97% identical to (SEQ ID NO: 166)

$LAEAKEAA\ X_1AELDX_6X_7GVG\ AX_{12}X_{13}IKX_{16}IX_{18}X_{19}AX_{21}X_{22}$ $VEX_{26}VQX_{28}X_{29}K\ QX_{32}ILAX_{36}\ LP$ wherein all amino acid residues denoted X are as defined in item 45.

47. Polypeptide according to any one of items 45-46, in which $X_1$ is I.

48. Polypeptide according to any one of items 45-46, in which $X_1$ is L.

49. Polypeptide according to any one of items 45-48, in which $X_6$ is S.

50. Polypeptide according to any one of items 45-48, in which $X_6$ is C.

51. Polypeptide according to any one of items 45-50, in which $X_7$ is K.

52. Polypeptide according to any one of items 45-50, in which $X_7$ is Y.

53. Polypeptide according to any one of items 45-52, in which $X_{18}$ is E.

54. Polypeptide according to any one of items 45-52, in which $X_{18}$ is Q.

55. Polypeptide according to any one of items 45-54, in which the amino acid residue in position 11 is A.

56. Polypeptide according to any one of items 45-55 further comprising a second polypeptide moiety, such that the polypeptide is a fusion polypeptide comprising a first moiety which fulfils the sequence definition of any one of items 45-55, and a second moiety with a desired function.

57. Polypeptide according to item 56, in which said second moiety is a polypeptide domain with binding affinity for albumin.

58. Polypeptide according to item 57, in which said polypeptide domain with binding affinity for albumin is a naturally occurring albumin binding domain from streptococcal Protein G, or an engineered variant thereof with retained or improved albumin binding affinity.

59. Polynucleotide encoding a polypeptide according to any one of items 45-58.

60. Method of producing a polypeptide according to any one of items 45-58, comprising the step of expressing a polynucleotide according to item 59.

The invention claimed is:

1. A population of polypeptide variants based on a common scaffold, each polypeptide in the population comprising the scaffold amino acid sequence (SEQ ID NO: 165)
$X_{sc1}$AELD$X_{sc2}X_{sc3}$GVG AXXIKXI$X_{sc4}$XA XXVEXVQXXK QX

ILAX wherein, independently of one another, $X_{sc1}$ is a scaffold amino acid residue selected from I and L;

$X_{sc2}$ is a scaffold amino acid residue selected from C and S;

$X_{sc3}$ is a scaffold amino acid residue selected from K and Y;

$X_{sc4}$ is a scaffold amino acid residue selected from E and Q; and each X individually is a binding amino acid residue corresponding to any amino acid residue.

2. A population according to claim 1, in which each polypeptide comprises the scaffold amino acid sequence (SEQ ID NO: 166)
LAEAKEAA$X_{sc1}$A ELD$X_{sc2}X_{sc3}$GVGAX XIKXI$X_{sc4}$XAXX VE

XVQXXKQX ILAXLP wherein $X_{sc1}$, $X_{sc2}$, $X_{sc3}$, $X_{sc4}$ and each individual X are as defined in claim 1.

3. A population according to claim 1, which comprises at least $1\times10^4$ unique polypeptide molecules.

4. A population of polynucleotides, characterized in that each member thereof encodes a member of a population of polypeptides according to claim 1.

5. A combination of a polypeptide population according to claim 1 with a polynucleotide population that encodes said polypeptide population, wherein each member of said population of polypeptides is physically or spatially associated with the polynucleotide encoding that member via means for genotype-phenotype coupling.

6. A method for selecting a desired polypeptide having an affinity for a predetermined target from a population of polypeptides, comprising the steps:

(a) contacting the population of polypeptides of claim 1 with a predetermined target under conditions that enable specific interaction between the target and at least one desired polypeptide having an affinity for the target; and (b) selecting, on the basis of said specific interaction, the at least one desired polypeptide from the remaining population of polypeptides.

7. A method according to claim 6, further comprising the steps of providing a population of polynucleotides that encodes said polypeptide population and expressing said population of polynucleotides to yield said population of polypeptides.

8. A method according to claim 7, wherein each member of said population of polypeptides is physically or spatially associated with the polynucleotide encoding that member via means for genotype-phenotype coupling.

9. A method for isolating a polynucleotide encoding a desired polypeptide having an affinity for a predetermined target, comprising the steps:

selecting said desired polypeptide and the polynucleotide encoding it from a population of polypeptides according to the method of claim 6; and isolating the thus separated polynucleotide encoding the desired polypeptide.

10. A method for identifying a desired polypeptide having an affinity for a predetermined target, comprising the steps:

isolating a polynucleotide encoding said desired polypeptide according to the method of claim 9; and sequencing the polynucleotide to establish by deduction the amino acid sequence of said desired polypeptide.

11. A method for selecting and identifying a desired polypeptide having an affinity for a predetermined target from a population of polypeptides, comprising the steps:

(a) synthesizing each member of a population of polypeptides according to claim 1 on a separate carrier or bead;

(b) selecting or enriching the carriers or beads based on the interaction of the polypeptide with the predetermined target; and (c) identifying the polypeptide by protein characterization methodology.

12. A method for production of a desired polypeptide having an affinity for a predetermined target, comprising the steps:

isolating and identifying a desired polypeptide using the method according to claim 10; and producing said desired polypeptide.

13. A method for production of a desired polypeptide having an affinity for a predetermined target, comprising the steps:

isolating a polynucleotide encoding said desired polypeptide according to the method of claim 9; and expressing the thus isolated polynucleotide to produce said desired polypeptide.

14. A Polypeptide comprising an amino acid sequence which is at least 97% identical to (SEQ ID NO: 165)

$X_1AELDX_6X_7GVG\ AX_{12}X_{13}IKX_{16}IX_{18}X_{19}A\ X_{21}X_{22}VEX_{25}VQ$ $X_{28}X_{29}K\ QX_{32}ILAX_3$ wherein, independently of one another, $X_1$ is selected from I and L;

$X_6$ is selected from C and S;

$X_7$ is selected from K and Y;

$X_{18}$ is selected from E and Q; and each of $X_{12}$, $X_{13}$, $X_{16}$, $X_{19}$, $X_{21}$, $X_{22}$, $X_{25}$, $X_{28}$, $X_{29}$, $X_{32}$ and $X_{36}$ is any amino acid residue.

15. A Polypeptide according to claim 14, which comprises an amino acid sequence which is at least 97% identical to (SEQ ID NO: 166)

$LAEAKEAA\ X_1AELDX_6X_7GVG\ AX_{12}X_{13}IKX_{16}IX_{18}X_{19}A\ X_{21}$ $X_{22}VEX_{25}VQX_{28}X_{29}KQX_{32}ILAX_{36}\ LP$ wherein all amino acid residues denoted X are as defined in claim 14.

16. The Polypeptide according to claim 14 further comprising a second polypeptide moiety, such that the polypeptide is a fusion polypeptide comprising a first moiety which fulfils the sequence definition of claim 14, and a second moiety with a desired function.

17. A method for production of a desired polypeptide having an affinity for a predetermined target, comprising the steps:

selecting and identifying a desired polypeptide according to the method of claim 11; and producing said desired polypeptide.

18. A method for production of a desired polypeptide having an affinity for a predetermined target, comprising the steps:

(a) backtranslating a polypeptide identified using the selection and identification method according to the method of claim 11; and (b) expressing the thus isolated polynucleotide to produce said desired polypeptide.

* * * * *

SEQUENCE LISTING

<160> NUMBER OF SEQ ID NOS: 173

<210> SEQ ID NO 1
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 1

Leu Ala Glu Ala Lys Glu Ala Ala Ile Ala Glu Leu Asp Ser Lys Gly
1 5 10 15

Ile Asn Glu Ala Ile Ile Ser Lys Ile Glu Arg Ala Glu Ser Val Glu
20 25 30

Glu Val Glu Tyr Trp Lys Glu Glu Ile Leu Ala Gln Leu Pro
35 40 45

<210> SEQ ID NO 2
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 2

Leu Ala Glu Ala Lys Glu Ala Ala Leu Ala Glu Leu Asp Ser Tyr Gly
1 5 10 15

-continued

Val Val Ala Asn Leu Lys Lys Lys Ile Glu Ile Ala Lys Ser Val Glu
20 25 30

Gln Val Glu Phe Trp Lys Glu Glu Ile Leu Ala Gln Leu Pro
35 40 45

<210> SEQ ID NO 3
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 3

Leu Ala Glu Ala Lys Glu Ala Ala Leu Ala Glu Leu Asp Ser Tyr Gly
1 5 10 15

Val Asp Glu Trp Gln Lys Ser Ala Ile Glu Arg Ala Gln Ala Val Glu
20 25 30

Glu Val Glu Phe Trp Lys Glu Asp Ile Leu Ala Gly Leu Pro
35 40 45

<210> SEQ ID NO 4
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 4

Leu Ala Glu Ala Lys Glu Ala Ala Asn Ala Glu Leu Asp Ser Tyr Gly
1 5 10 15

Val Asp Ala Asp Leu Ile Lys Lys Ile Glu Arg Ala Glu Ser Val Glu
20 25 30

Glu Val Glu Phe Trp Lys Glu Glu Ile Leu Ala His Leu Pro
35 40 45

<210> SEQ ID NO 5
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 5

Leu Ala Glu Ala Lys Glu Ala Ala Ile Ala Glu Leu Asp Ser Ala Gly
1 5 10 15

Val Asn Glu Val Gln Lys Ser Lys Ile Glu Gln Ala Ser Ser Val Glu
20 25 30

Glu Val Glu Phe Trp Lys Glu Glu Ile Leu Ala Gln Leu Pro
35 40 45

<210> SEQ ID NO 6
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 6

Leu Ala Glu Ala Lys Glu Ala Ala Ile Ala Glu Leu Asp Ser Tyr Gly
1 5 10 15

Val Val Ala Asn Leu Lys Lys Lys Ile Glu Ile Ala Lys Ser Val Glu
20 25 30

```
Gln Val Glu Phe Trp Lys Glu Glu Ile Leu Ala Gln Leu Pro
        35                  40                  45


<210> SEQ ID NO 7
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 7

Leu Ala Glu Ala Lys Glu Ala Ala Leu Ala Glu Leu Asp Ser Lys Gly
1               5                   10                  15

Ile Asn Glu Ala Ile Ile Ser Lys Ile Glu Arg Ala Glu Ser Val Glu
            20                  25                  30

Glu Val Glu Tyr Trp Lys Glu Glu Ile Leu Ala Gln Leu Pro
        35                  40                  45


<210> SEQ ID NO 8
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 8

Leu Ala Glu Ala Lys Glu Ala Ala Ile Ala Glu Leu Asp Ser Tyr Gly
1               5                   10                  15

Ile Thr Glu Glu Leu Ile Ser Lys Ile Glu His Ala Gly Ser Val Glu
            20                  25                  30

Glu Val Glu Trp Trp Lys Glu Glu Ile Leu Ala Gln Leu Pro
        35                  40                  45


<210> SEQ ID NO 9
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 9

Leu Ala Glu Ala Lys Glu Ala Ala Leu Ala Glu Leu Asp Ser Ala Gly
1               5                   10                  15

Val Asp Glu Trp Ser Ile Lys Lys Ile Glu Ala Ala Lys Ile Val Glu
            20                  25                  30

Glu Val Glu Phe Trp Lys Glu Glu Ile Leu Ala Gln Leu Pro
        35                  40                  45


<210> SEQ ID NO 10
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 10

Leu Ala Glu Ala Lys Glu Ala Ala Ile Ala Glu Leu Asp Ser Lys Gly
1               5                   10                  15

Val His Asp Ala His Lys Glu Arg Ile Glu Arg Ala Tyr Ser Val Glu
            20                  25                  30

Gln Val Glu Phe Trp Lys Glu Glu Ile Leu Ala Gln Leu Pro
        35                  40                  45
```

<210> SEQ ID NO 11
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 11

```
Leu Ala Glu Ala Lys Glu Ala Ala Ile Ala Glu Leu Asp Ser Ala Gly
1               5                   10                  15

Val Lys Glu His Asn Ile Ser Lys Ile Glu Lys Ala Leu Ser Val Glu
            20                  25                  30

Glu Val Glu Tyr Trp Lys Glu Glu Ile Leu Ala Gln Leu Pro
        35                  40                  45
```

<210> SEQ ID NO 12
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 12

```
Leu Ala Glu Ala Lys Glu Ala Ala Ile Ala Glu Leu Asp Ser Tyr Gly
1               5                   10                  15

Val Thr Ala Val Leu Lys Ser Lys Ile Glu Lys Ala Val Ser Val Glu
            20                  25                  30

Ala Val Glu Phe Trp Lys Glu Glu Ile Leu Ala Tyr Leu Pro
        35                  40                  45
```

<210> SEQ ID NO 13
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 13

```
Leu Ala Glu Ala Lys Glu Ala Ala Ile Ala Glu Leu Asp Ser Tyr Gly
1               5                   10                  15

Ile Tyr Asp Ser Arg Lys Ser Lys Ile Glu Asn Ala Gln Ile Val Glu
            20                  25                  30

Glu Val Glu Phe Trp Lys Glu Glu Ile Leu Ala Gln Leu Pro
        35                  40                  45
```

<210> SEQ ID NO 14
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 14

```
Leu Ala Glu Ala Lys Glu Ala Ala Ile Ala Glu Leu Asp Ser Ala Gly
1               5                   10                  15

Val Ser Asp Asn Leu Lys Ser Lys Ile Glu Arg Gly Leu Ser Val Glu
            20                  25                  30

Glu Val Glu Phe Trp Lys Glu Glu Ile Leu Ala Tyr Leu Pro
        35                  40                  45
```

<210> SEQ ID NO 15

<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 15

```
Leu Ala Glu Ala Lys Glu Ala Ala Leu Ala Glu Leu Asp Ser Ala Gly
1               5                   10                  15

Ile Gln Asp Ala Trp Ile Ser Trp Ile Glu Arg Ala Tyr Ser Val Glu
            20                  25                  30

Glu Val Glu Phe Lys Lys Glu Glu Ile Leu Ala Gln Leu Pro
        35                  40                  45
```

<210> SEQ ID NO 16
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 16

```
Leu Ala Glu Ala Lys Glu Ala Ala Ile Ala Glu Leu Asp Ser Ala Gly
1               5                   10                  15

Val His Asp Ala His Ile Ser Lys Ile Glu Trp Ala Ala Ala Val Glu
            20                  25                  30

Glu Val Glu Phe Trp Lys Glu Glu Ile Leu Ala Gln Leu Pro
        35                  40                  45
```

<210> SEQ ID NO 17
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 17

```
Leu Ala Glu Ala Lys Glu Ala Ala Leu Ala Glu Leu Asp Ser Tyr Gly
1               5                   10                  15

Val Asp Glu Trp Gln Lys Ser Thr Ile Glu Arg Ala Gln Ala Val Glu
            20                  25                  30

Glu Val Glu Phe Trp Lys Glu Asp Ile Leu Ala Gly Leu Pro
        35                  40                  45
```

<210> SEQ ID NO 18
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 18

```
Leu Ala Glu Ala Lys Glu Ala Ala Ile Ala Glu Leu Asp Ser Lys Gly
1               5                   10                  15

Ile Asn Glu Ala Ile Ile Lys Lys Ile Glu Arg Ala Glu Ser Val Glu
            20                  25                  30

Glu Val Glu Tyr Trp Lys Glu Glu Ile Leu Ala Gln Leu Pro
        35                  40                  45
```

<210> SEQ ID NO 19
<211> LENGTH: 46
<212> TYPE: PRT
<213> ORGANISM: Artificial Sequence -continued
<220> FEATURE:
<223> OTHER INFORMATION: Engineered C4 binding Y variant

<400> SEQUENCE: 19

Leu Ala Glu Ala Lys Glu Ala Ala Ile Ala Glu Leu Asp Ser Lys Gly
1 5 10 15

Val Asn Glu Ala Ile Ile Lys Lys Ile Glu Arg Ala Glu Ser Val Glu
20 25 30

Glu Val Glu Tyr Trp Lys Glu Glu Ile Leu Ala Gln Leu Pro
35 40 45

<210> SEQ ID NO 20
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 20

Leu Ala Glu Ala Lys Glu Ala Ala Ile Ala Glu Leu Asp Ser Lys Gly
1 5 10 15

Ile Ser Glu Ala Ile Ile Lys Lys Ile Glu Arg Ala Glu Ser Val Glu
20 25 30

Glu Val Glu Tyr Trp Lys Glu Glu Ile Leu Ala Gln Leu Pro
35 40 45

<210> SEQ ID NO 21
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 21

Leu Ala Glu Ala Lys Glu Ala Ala Ile Ala Glu Leu Asp Ser Lys Gly
1 5 10 15

Ile Asn Ala Ala Ile Ile Lys Lys Ile Glu Arg Ala Glu Ser Val Glu
20 25 30

Glu Val Glu Tyr Trp Lys Glu Glu Ile Leu Ala Gln Leu Pro
35 40 45

<210> SEQ ID NO 22
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 22

Leu Ala Glu Ala Lys Glu Ala Ala Ile Ala Glu Leu Asp Ser Lys Gly
1 5 10 15

Ile Asn Glu Ala Ile Lys Lys Lys Ile Glu Arg Ala Glu Ser Val Glu
20 25 30

Glu Val Glu Tyr Trp Lys Glu Glu Ile Leu Ala Gln Leu Pro
35 40 45

<210> SEQ ID NO 23
<211> LENGTH: 46
<212> TYPE: PRT
<213> ORGANISM: Artificial Sequence
<220> FEATURE:
<223> OTHER INFORMATION: Engineered C4 binding Y variant -continued

<400> SEQUENCE: 23

```
Leu Ala Glu Ala Lys Glu Ala Ala Ile Ala Glu Leu Asp Ser Lys Gly
1               5                   10                  15

Ile Asn Glu Ala Ile Ile Lys Lys Ile Gln Arg Ala Glu Ser Val Glu
            20                  25                  30

Glu Val Glu Tyr Trp Lys Glu Glu Ile Leu Ala Gln Leu Pro
        35                  40                  45
```

<210> SEQ ID NO 24
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 24

```
Leu Ala Glu Ala Lys Glu Ala Ala Ile Ala Glu Leu Asp Ser Lys Gly
1               5                   10                  15

Ile Asn Glu Ala Ile Ile Lys Lys Ile Glu Arg Ala Glu Ser Val Glu
            20                  25                  30

Glu Val Gln Tyr Trp Lys Glu Glu Ile Leu Ala Gln Leu Pro
        35                  40                  45
```

<210> SEQ ID NO 25
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 25

```
Leu Ala Glu Ala Lys Glu Ala Ala Ile Ala Glu Leu Asp Ser Lys Gly
1               5                   10                  15

Ile Asn Glu Ala Ile Ile Lys Lys Ile Glu Arg Ala Glu Ser Val Glu
            20                  25                  30

Glu Val Glu Tyr Trp Lys Gln Glu Ile Leu Ala Gln Leu Pro
        35                  40                  45
```

<210> SEQ ID NO 26
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 26

```
Leu Ala Glu Ala Lys Glu Ala Ala Ile Ala Glu Leu Asp Ser Lys Gly
1               5                   10                  15

Ile Asn Glu Ala Ile Ile Lys Lys Ile Glu Arg Ala Glu Ser Val Glu
            20                  25                  30

Glu Val Gln Tyr Trp Lys Gln Glu Ile Leu Ala Gln Leu Pro
        35                  40                  45
```

<210> SEQ ID NO 27
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 27

```
Leu Ala Glu Ala Lys Glu Ala Ala Ile Ala Glu Leu Asp Ser Lys Gly
```

```
1               5                   10                  15

Ile Asn Glu Ala Ile Ile Lys Lys Ile Glu Arg Ala Glu Ser Val Glu
            20                  25                  30

Glu Val Gln Tyr Trp Lys Glu Glu Ile Leu Lys Gln Leu Pro
        35                  40                  45


<210> SEQ ID NO 28
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 28

Leu Ala Glu Ala Lys Glu Ala Ala Ile Ala Glu Leu Asp Ser Lys Gly
1               5                   10                  15

Ile Asn Glu Ala Ile Ile Lys Lys Ile Glu Arg Ala Glu Ser Val Glu
            20                  25                  30

Glu Val Gln Tyr Trp Lys Gln Glu Ile Leu Lys Gln Leu Pro
        35                  40                  45


<210> SEQ ID NO 29
<211> LENGTH: 46
<212> TYPE: PRT
<213> ORGANISM: Artificial Sequence
<220> FEATURE:
<223> OTHER INFORMATION: Engineered C4 binding Y variant

<400> SEQUENCE: 29

Leu Ala Glu Ala Lys Glu Ala Ala Ile Ala Glu Leu Asp Ser Lys Gly
1               5                   10                  15

Val Gly Ala Ala Ile Ile Lys Lys Ile Gln Arg Ala Glu Ser Val Glu
            20                  25                  30

Glu Val Gln Tyr Trp Lys Gln Glu Ile Leu Ala Gln Leu Pro
        35                  40                  45


<210> SEQ ID NO 30
<211> LENGTH: 51
<212> TYPE: PRT
<213> ORGANISM: Artificial Sequence
<220> FEATURE:
<223> OTHER INFORMATION: Engineered C4 binding Y variant

<400> SEQUENCE: 30

Leu Ala Glu Ala Lys Glu Ala Ala Ile Ala Glu Leu Asp Ser Lys Gly
1               5                   10                  15

Val Gly Ala Ala Ile Ile Lys Lys Ile Gln Arg Ala Glu Ser Val Glu
            20                  25                  30

Glu Val Gln Tyr Trp Lys Gln Glu Ile Leu Ala Gln Leu Pro Ala Ser
        35                  40                  45

Tyr Gly Ser
    50


<210> SEQ ID NO 31
<211> LENGTH: 49
<212> TYPE: PRT
<213> ORGANISM: Artificial Sequence
<220> FEATURE:
<223> OTHER INFORMATION: Engineered C4 binding Y variant

<400> SEQUENCE: 31

Leu Ala Glu Ala Lys Glu Ala Ala Ile Ala Glu Leu Asp Ser Lys Gly
```

```
1               5                   10                  15

Val Gly Ala Ala Ile Ile Lys Lys Ile Gln Arg Ala Glu Ser Val Glu
            20                  25                  30

Glu Val Gln Tyr Trp Lys Gln Glu Ile Leu Ala Gln Leu Pro Gly Tyr
        35                  40                  45

Ser


<210> SEQ ID NO 32
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 32

Leu Ala Glu Ala Lys Glu Ala Ala Ile Ala Glu Leu Asp Ser Lys Gly
1               5                   10                  15

Val Gly Ala Asp Leu Ile Lys Lys Ile Gln Gln Ala Ser Ser Val Glu
            20                  25                  30

Gly Val Gln Phe Trp Lys Gln Glu Ile Leu Ala Gln Leu Pro Ala
        35                  40                  45


<210> SEQ ID NO 33
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 33

Leu Ala Glu Ala Lys Glu Ala Ala Ile Ala Glu Leu Asp Ser Lys Gly
1               5                   10                  15

Val Gly Ala Met Trp Ile Lys Tyr Ile Gln Arg Ala Lys Asp Val Glu
            20                  25                  30

Gly Val Gln Lys Trp Lys Gln Gly Ile Leu Ala Leu Leu Pro Ala
        35                  40                  45


<210> SEQ ID NO 34
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 34

Leu Ala Glu Ala Lys Glu Ala Ala Ile Ala Glu Leu Asp Ser Lys Gly
1               5                   10                  15

Val Gly Ala Glu Glu Ile Lys Trp Ile Gln Asn Ala Trp Ser Val Glu
            20                  25                  30

Gly Val Gln Ile Met Lys Gln Gln Ile Leu Ala Glu Leu Pro Ala
        35                  40                  45


<210> SEQ ID NO 35
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 35

Leu Ala Glu Ala Lys Glu Ala Ala Ile Ala Glu Leu Asp Ser Lys Gly
1               5                   10                  15
```

```
Val Gly Ala Asp Leu Ile Lys Lys Ile Gln Lys Ala Glu Ser Val Glu
            20                  25                  30

Gly Val Gln Phe Trp Lys Gln Glu Ile Leu Ala Thr Leu Pro Ala
        35                  40                  45


<210> SEQ ID NO 36
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 36

Leu Ala Glu Ala Lys Glu Ala Ala Ile Ala Glu Leu Asp Ser Lys Gly
1               5                   10                  15

Val Gly Ala Asp Leu Ile Lys Lys Ile Gln Tyr Ala Asp Thr Val Glu
            20                  25                  30

Gly Val Gln Phe Trp Lys Gln Glu Ile Leu Ala Trp Leu Pro Ala
        35                  40                  45


<210> SEQ ID NO 37
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 37

Leu Ala Glu Ala Lys Glu Ala Ala Ile Ala Glu Leu Asp Ser Lys Gly
1               5                   10                  15

Val Gly Ala Glu Leu Ile Lys Lys Ile Gln His Ala Glu Ser Val Glu
            20                  25                  30

Gly Val Gln Phe Trp Lys Gln Glu Ile Leu Ala Tyr Leu Pro Ala
        35                  40                  45


<210> SEQ ID NO 38
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 38

Leu Ala Glu Ala Lys Glu Ala Ala Ile Ala Glu Leu Asp Ser Lys Gly
1               5                   10                  15

Val Gly Ala Ala Glu Ile Lys Trp Ile Gln His Ala Ser Thr Val Glu
            20                  25                  30

Gly Val Gln Gly Arg Lys Gln Gln Ile Leu Ala Glu Leu Pro Ala
        35                  40                  45


<210> SEQ ID NO 39
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 39

Leu Ala Glu Ala Lys Glu Ala Ala Ile Ala Glu Leu Asp Ser Lys Gly
1               5                   10                  15

Val Gly Ala Asp Asp Ile Lys Leu Ile Gln Asp Ala Pro Ser Val Glu
            20                  25                  30
```

Gly Val Gln Glu Ile Lys Gln Phe Ile Leu Ala Gln Leu Pro Ala
35 40 45

<210> SEQ ID NO 40
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 40

Leu Ala Glu Ala Lys Glu Ala Ala Leu Ala Glu Leu Asp Ser Lys Gly
1 5 10 15

Val Gly Ala Asp Leu Ile Lys Lys Ile Gln Gln Ala Ser Ser Val Glu
20 25 30

Gly Val Gln Phe Trp Lys Gln Glu Ile Leu Ala Gln Leu Pro Ala
35 40 45

<210> SEQ ID NO 41
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 41

Leu Ala Glu Ala Lys Glu Ala Ala Ile Ala Glu Leu Asp Ser Tyr Gly
1 5 10 15

Val Gly Ala Asp Leu Ile Lys Lys Ile Gln Gln Ala Ser Ser Val Glu
20 25 30

Gly Val Gln Phe Trp Lys Gln Glu Ile Leu Ala Gln Leu Pro Ala
35 40 45

<210> SEQ ID NO 42
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 42

Leu Ala Glu Ala Lys Glu Ala Ala Ile Ala Glu Leu Asp Ser Lys Gly
1 5 10 15

Val Gly Ala Asp Leu Ile Lys Lys Ile Glu Gln Ala Ser Ser Val Glu
20 25 30

Gly Val Gln Phe Trp Lys Gln Glu Ile Leu Ala Gln Leu Pro Ala
35 40 45

<210> SEQ ID NO 43
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 43

Leu Ala Glu Ala Lys Glu Ala Ala Leu Ala Glu Leu Asp Ser Lys Gly
1 5 10 15

Val Gly Ala Glu Leu Ile Lys Lys Ile Gln His Ala Glu Ser Val Glu
20 25 30

Gly Val Gln Phe Trp Lys Gln Glu Ile Leu Ala Tyr Leu Pro Ala
35 40 45

<210> SEQ ID NO 44
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 44

Leu Ala Glu Ala Lys Glu Ala Ala Ile Ala Glu Leu Asp Ser Tyr Gly
1 5 10 15

Val Gly Ala Glu Leu Ile Lys Lys Ile Gln His Ala Glu Ser Val Glu
20 25 30

Gly Val Gln Phe Trp Lys Gln Glu Ile Leu Ala Tyr Leu Pro Ala
35 40 45

<210> SEQ ID NO 45
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 45

Leu Ala Glu Ala Lys Glu Ala Ala Ile Ala Glu Leu Asp Ser Lys Gly
1 5 10 15

Val Gly Ala Glu Leu Ile Lys Lys Ile Glu His Ala Glu Ser Val Glu
20 25 30

Gly Val Gln Phe Trp Lys Gln Glu Ile Leu Ala Tyr Leu Pro Ala
35 40 45

<210> SEQ ID NO 46
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 46

Leu Ala Glu Ala Lys Glu Ala Ala Ile Ala Glu Leu Asp Ser Tyr Gly
1 5 10 15

Val Gly Ala Asp Leu Ile Lys Lys Ile Glu Gln Ala Ser Ser Val Glu
20 25 30

Gly Val Gln Phe Trp Lys Gln Glu Ile Leu Ala Gln Leu Pro Ala
35 40 45

<210> SEQ ID NO 47
<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 47

Leu Ala Glu Ala Lys Glu Ala Ala Ile Ala Glu Leu Asp Ser Tyr Gly
1 5 10 15

Val Gly Ala Asp Leu Ile Lys Lys Ile Glu Lys Ala Glu Ser Val Glu
20 25 30

Gly Val Gln Phe Trp Lys Gln Glu Ile Leu Ala Thr Leu Pro Ala
35 40 45

<210> SEQ ID NO 48

<211> LENGTH: 47
<212> TYPE: PRT
<213> ORGANISM: Artificial Sequence
<220> FEATURE:
<223> OTHER INFORMATION: Engineered C4 binding Y variant

<400> SEQUENCE: 48

```
Leu Ala Glu Ala Lys Glu Ala Ala Ile Ala Glu Leu Asp Ser Tyr Gly
1               5                   10                  15

Val Gly Ala Glu Leu Ile Lys Lys Ile Glu His Ala Glu Ser Val Glu
            20                  25                  30

Gly Val Gln Phe Trp Lys Gln Glu Ile Leu Ala Tyr Leu Pro Ala
        35                  40                  45
```

<210> SEQ ID NO 49
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 49

```
Leu Ala Glu Ala Lys Glu Ala Ala Asn Ala Glu Leu Asp Ser Ala Gly
1               5                   10                  15

Ile Lys Glu Ile Asn Lys Glu His Ile Glu Leu Ala Glu Ile Val Glu
            20                  25                  30

Leu Val Glu Leu Leu Lys Glu Glu Ile Leu Lys Lys Leu Pro
        35                  40                  45
```

<210> SEQ ID NO 50
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 50

```
Leu Ala Glu Ala Lys Glu Ala Ala Asn Ala Glu Leu Asp Ser Tyr Gly
1               5                   10                  15

Val Gln Ala Asn Ser Ile Glu Ala Ile Glu Gln Gly Leu Phe Val Glu
            20                  25                  30

Val Val Glu Leu Leu Lys Glu Leu Ile Leu Ala Ala Leu Pro
        35                  40                  45
```

<210> SEQ ID NO 51
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 51

```
Leu Ala Glu Ala Lys Glu Ala Ala Asn Ala Glu Leu Asp Ser Lys Gly
1               5                   10                  15

Val Gln Asp Arg Ser Ile Ser Lys Ile Glu Ala Gly Tyr Phe Val Glu
            20                  25                  30

Val Val Glu Leu Leu Lys Glu Leu Ile Leu Ala Ala Leu Pro
        35                  40                  45
```

<210> SEQ ID NO 52
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 52

Leu Ala Glu Ala Lys Glu Ala Ala Ile Ala Glu Leu Asp Ser Ala Gly
1 5 10 15

Val His Ala His Ala Lys Ser Ser Ile Glu Ser Ala Leu Trp Val Glu
20 25 30

Val Val Glu Leu Leu Lys Glu Asn Ile Leu Ala Thr Leu Pro
35 40 45

<210> SEQ ID NO 53
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 53

Leu Ala Glu Ala Lys Glu Ala Ala Ile Ala Glu Leu Asp Ser Ala Gly
1 5 10 15

Ile Gln Asp Glu Asp Ile Ser Ile Ile Glu Glu Ala Leu Trp Val Glu
20 25 30

Val Val Glu Leu Leu Lys Glu Leu Ile Leu Ala Ser Leu Pro
35 40 45

<210> SEQ ID NO 54
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 54

Leu Ala Glu Ala Lys Glu Ala Ala Ile Ala Glu Leu Asp Ser Ala Gly
1 5 10 15

Val Gln Glu Glu Arg Ile Glu Val Ile Glu Ala Gly Leu Trp Val Glu
20 25 30

Val Val Glu Leu Leu Lys Glu Ala Ile Leu Ala Ala Leu Pro
35 40 45

<210> SEQ ID NO 55
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 55

Leu Ala Glu Ala Lys Glu Ala Ala Ile Ala Glu Leu Asp Ser Ala Gly
1 5 10 15

Val Asp Asp Ile Asp Lys Lys Val Ile Glu Glu Gly Leu Trp Val Glu
20 25 30

Val Val Glu Leu Leu Lys Glu Ala Ile Leu Ala Ala Leu Pro
35 40 45

<210> SEQ ID NO 56
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 56

Leu Ala Glu Ala Lys Glu Ala Ala Ile Ala Glu Leu Asp Ser Ala Gly
1 5 10 15

Ile His Glu Gln Ser Ile Lys Ser Ile Glu Glu Ala Leu Trp Val Glu
20 25 30

Val Val Glu Leu Leu Lys Glu Ser Ile Leu Ala Val Leu Pro
35 40 45

<210> SEQ ID NO 57
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 57

Leu Ala Glu Ala Lys Glu Ala Ala Ile Ala Glu Leu Asp Ser Ala Gly
1 5 10 15

Val Asn Asp Ile Gln Ile Glu Leu Ile Glu Lys Gly Leu Trp Val Glu
20 25 30

Val Val Glu Leu Leu Lys Glu Leu Ile Leu Ala Ala Leu Pro
35 40 45

<210> SEQ ID NO 58
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 58

Leu Ala Glu Ala Lys Glu Ala Ala Ile Ala Glu Leu Asp Ser Ala Gly
1 5 10 15

Val Lys Glu Leu Glu Ile Lys Ala Ile Glu His Ala Leu Trp Val Glu
20 25 30

Val Val Glu Leu Leu Lys Glu Asn Ile Leu Ala Ala Leu Pro
35 40 45

<210> SEQ ID NO 59
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 59

Leu Ala Glu Ala Lys Glu Ala Ala Ile Ala Glu Leu Asp Ser Tyr Gly
1 5 10 15

Val Thr Glu Val Ser Lys Ser Phe Ile Glu Ser Gly Glu Trp Val Glu
20 25 30

Val Val Glu Leu Leu Lys Glu Leu Ile Leu Ala Thr Leu Pro
35 40 45

<210> SEQ ID NO 60
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 60

Leu Ala Glu Ala Lys Glu Ala Ala Ile Ala Glu Leu Asp Ser Ala Gly

```
1               5                   10                  15

Val Asp Ala Val Gln Ile Ser Glu Ile Glu Arg Gly Glu Trp Val Glu
            20                  25                  30

Val Val Glu Leu Leu Lys Glu Ile Ile Leu Ala Val Leu Pro
        35                  40                  45


<210> SEQ ID NO 61
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 61

Leu Ala Glu Ala Lys Glu Ala Ala Leu Ala Glu Leu Asp Ser Lys Gly
1               5                   10                  15

Ile Glu Glu Lys Ser Ile Ser Glu Ile Glu Ala Gly Leu Trp Val Glu
            20                  25                  30

Val Val Glu Leu Leu Lys Glu Ser Ile Leu Ala Val Leu Pro
        35                  40                  45


<210> SEQ ID NO 62
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 62

Leu Ala Glu Ala Lys Glu Ala Ala Asn Ala Glu Leu Asp Ser Tyr Gly
1               5                   10                  15

Val Ala Glu Ile Glu Lys Glu Glu Ile Glu Lys Gly Leu Trp Val Glu
            20                  25                  30

Val Val Glu Leu Leu Lys Glu Asn Ile Leu Ala Ser Leu Pro
        35                  40                  45


<210> SEQ ID NO 63
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 63

Leu Ala Glu Ala Lys Glu Ala Ala Asn Ala Glu Leu Asp Ser Lys Gly
1               5                   10                  15

Val Asp Ala Glu Arg Ile Glu Ile Ile Glu Glu Gly Leu Trp Val Glu
            20                  25                  30

Val Val Glu Leu Leu Lys Glu Asn Ile Leu Ala Ala Leu Pro
        35                  40                  45


<210> SEQ ID NO 64
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 64

Leu Ala Glu Ala Lys Glu Ala Ala Asn Ala Glu Leu Asp Ser Lys Gly
1               5                   10                  15

Val Thr Ala Lys Arg Lys Ser Ala Ile Glu Ser Gly Leu Phe Val Glu
```

20 25 30

Val Val Glu Leu Leu Lys Glu Asn Ile Leu Ala Ala Leu Pro
35 40 45

<210> SEQ ID NO 65
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 65

Leu Ala Glu Ala Lys Glu Ala Ala Asn Ala Glu Leu Asp Ser Tyr Gly
1 5 10 15

Val Val Asp Asp Ser Ile Lys Arg Ile Glu His Gly Leu Trp Val Glu
20 25 30

Val Val Glu Leu Ile Lys Glu Asn Ile Leu Ala Val Leu Pro
35 40 45

<210> SEQ ID NO 66
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 66

Leu Ala Glu Ala Lys Glu Ala Ala Asn Ala Glu Leu Asp Ser Ala Gly
1 5 10 15

Val Tyr Glu Gly Arg Ile Ser Thr Ile Glu Gln Gly Leu Phe Val Glu
20 25 30

Val Val Glu Leu Leu Lys Glu Leu Ile Leu Ala Thr Leu Pro
35 40 45

<210> SEQ ID NO 67
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 67

Leu Ala Glu Ala Lys Glu Ala Ala Asn Ala Glu Leu Asp Ser Ala Gly
1 5 10 15

Val Thr Glu Tyr Lys Ile Glu Thr Ile Glu Gln Gly Leu Trp Val Glu
20 25 30

Leu Val Glu Leu Leu Lys Glu Asn Ile Leu Ala Ala Leu Pro
35 40 45

<210> SEQ ID NO 68
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 68

Leu Ala Glu Ala Lys Glu Ala Ala Asn Ala Glu Leu Asp Ser Ala Gly
1 5 10 15

Ile Ser Asp Gln Gln Ile Glu Ser Ile Glu Arg Gly Leu Trp Val Glu
20 25 30

Val Val Glu Leu Leu Lys Glu Ala Ile Leu Ala Val Leu Pro 35 40 45

<210> SEQ ID NO 69
<211> LENGTH: 46
<212> TYPE: PRT
<213> ORGANISM: Artificial Sequence
<220> FEATURE:
<223> OTHER INFORMATION: Engineered IL-6 binding Y variant

<400> SEQUENCE: 69

Leu Ala Glu Ala Lys Glu Ala Ala Leu Ala Glu Leu Asp Ser Tyr Gly
1 5 10 15

Ile Asp Glu Phe His Lys Ser Tyr Ile Glu Gln Ala Gly Gly Val Glu
20 25 30

Glu Val Glu Trp Tyr Lys Glu Ile Ile Leu Lys Ser Leu Pro
35 40 45

<210> SEQ ID NO 70
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 70

Leu Ala Glu Ala Lys Glu Ala Ala Ile Ala Glu Leu Asp Ser Lys Gly
1 5 10 15

Val Gly Ala Asp Thr Ile Lys Asp Ile Gln Pro Ala Ile Leu Val Glu
20 25 30

Ile Val Gln Leu Leu Lys Gln Ala Ile Leu Ala Val Leu Pro Ala
35 40 45

<210> SEQ ID NO 71
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 71

Leu Ala Glu Ala Lys Glu Ala Ala Ile Ala Glu Leu Asp Ser Lys Gly
1 5 10 15

Val Gly Ala Asp Gly Ile Lys Glu Ile Gln Gln Ala Met Leu Val Glu
20 25 30

Ile Val Gln Leu Leu Lys Gln Ala Ile Leu Ala Val Leu Pro Ala
35 40 45

<210> SEQ ID NO 72
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 72

Leu Ala Glu Ala Lys Glu Ala Ala Ile Ala Glu Leu Asp Ser Lys Gly
1 5 10 15

Val Gly Ala Ala Glu Ile Lys Arg Ile Gln Ala Ala Glu Leu Val Glu
20 25 30

Ile Val Gln Leu Leu Lys Gln Ala Ile Leu Ala Val Leu Pro Ala
35 40 45

<210> SEQ ID NO 73
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 73

```
Leu Ala Glu Ala Lys Glu Ala Ala Ile Ala Glu Leu Asp Ser Lys Gly
1               5                   10                  15

Val Gly Ala Arg Asp Ile Lys Leu Ile Gln Glu Ala Met Leu Val Glu
            20                  25                  30

Ile Val Gln Leu Leu Lys Gln Ala Ile Leu Ala Val Leu Pro Ala
        35                  40                  45
```

<210> SEQ ID NO 74
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 74

```
Leu Ala Glu Ala Lys Glu Ala Ala Ile Ala Glu Leu Asp Ser Lys Gly
1               5                   10                  15

Val Gly Ala Gly Asp Ile Lys Asp Ile Gln Asp Ala Leu Leu Val Glu
            20                  25                  30

Ile Val Gln Leu Leu Lys Gln Ala Ile Leu Ala Val Leu Pro Ala
        35                  40                  45
```

<210> SEQ ID NO 75
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 75

```
Leu Ala Glu Ala Lys Glu Ala Ala Ile Ala Glu Leu Asp Ser Lys Gly
1               5                   10                  15

Val Gly Ala Val Glu Ile Lys Gln Ile Gln Glu Ala Leu Leu Val Glu
            20                  25                  30

Ile Val Gln Leu Leu Lys Gln Ala Ile Leu Ala Val Leu Pro Ala
        35                  40                  45
```

<210> SEQ ID NO 76
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 76

```
Leu Ala Glu Ala Lys Glu Ala Ala Ile Ala Glu Leu Asp Ser Lys Gly
1               5                   10                  15

Val Gly Ala His Gly Ile Lys Glu Ile Gln Asp Ala Ile Leu Val Glu
            20                  25                  30

Ile Val Gln Leu Leu Lys Gln Ala Ile Leu Ala Ala Leu Pro Ala
        35                  40                  45
```

<210> SEQ ID NO 77
<211> LENGTH: 47
<212> TYPE: PRT

<213> ORGANISM: Artificial Sequence
<220> FEATURE:
<223> OTHER INFORMATION: Engineered IL-6 binding Y variant

<400> SEQUENCE: 77

Leu Ala Glu Ala Lys Glu Ala Ala Ile Ala Glu Leu Asp Ser Lys Gly
1 5 10 15

Val Gly Ala Tyr Ile Ile Lys Asp Ile Gln Leu Ala Met Met Val Glu
20 25 30

Ile Val Gln Met Leu Lys Gln Ala Ile Leu Ala Ser Leu Pro Ala
35 40 45

<210> SEQ ID NO 78
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 78

Leu Ala Glu Ala Lys Glu Ala Ala Ile Ala Glu Leu Asp Ser Lys Gly
1 5 10 15

Val Gly Ala Asn His Ile Lys Ala Ile Gln His Ala Gln Phe Val Glu
20 25 30

Ile Val Gln Leu Leu Lys Gln Ala Ile Leu Ala Val Leu Pro Ala
35 40 45

<210> SEQ ID NO 79
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 79

Leu Ala Glu Ala Lys Glu Ala Ala Ile Ala Glu Leu Asp Ser Lys Gly
1 5 10 15

Val Gly Ala Glu Glu Ile Lys Glu Ile Gln Gly Ala Met Leu Val Glu
20 25 30

Ile Val Gln Leu Leu Lys Gln Ala Ile Leu Ala Val Leu Pro Ala
35 40 45

<210> SEQ ID NO 80
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 80

Leu Ala Glu Ala Lys Glu Ala Ala Ile Ala Glu Leu Asp Ser Lys Gly
1 5 10 15

Val Gly Ala His Glu Ile Lys Glu Ile Gln Ile Ala Glu Leu Val Glu
20 25 30

Ile Val Gln Leu Leu Lys Gln Ala Ile Leu Ala Val Leu Pro Ala
35 40 45

<210> SEQ ID NO 81
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 81

Leu Ala Glu Ala Lys Glu Ala Ala Leu Ala Glu Leu Asp Ser Lys Gly
1               5                   10                  15

Val Gly Ala Val Glu Ile Lys Gln Ile Gln Glu Ala Leu Leu Val Glu
            20                  25                  30

Ile Val Gln Leu Leu Lys Gln Ala Ile Leu Ala Val Leu Pro Ala
        35                  40                  45

<210> SEQ ID NO 82
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 82

Leu Ala Glu Ala Lys Glu Ala Ala Ile Ala Glu Leu Asp Ser Tyr Gly
1               5                   10                  15

Val Gly Ala Val Glu Ile Lys Gln Ile Gln Glu Ala Leu Leu Val Glu
            20                  25                  30

Ile Val Gln Leu Leu Lys Gln Ala Ile Leu Ala Val Leu Pro Ala
        35                  40                  45

<210> SEQ ID NO 83
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 83

Leu Ala Glu Ala Lys Glu Ala Ala Ile Ala Glu Leu Asp Ser Lys Gly
1               5                   10                  15

Val Gly Ala Val Glu Ile Lys Gln Ile Glu Glu Ala Leu Leu Val Glu
            20                  25                  30

Ile Val Gln Leu Leu Lys Gln Ala Ile Leu Ala Val Leu Pro Ala
        35                  40                  45

<210> SEQ ID NO 84
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 84

Leu Ala Glu Ala Lys Glu Ala Ala Leu Ala Glu Leu Asp Ser Lys Gly
1               5                   10                  15

Val Gly Ala Gly Asp Ile Lys Asp Ile Gln Asp Ala Leu Leu Val Glu
            20                  25                  30

Ile Val Gln Leu Leu Lys Gln Ala Ile Leu Ala Val Leu Pro Ala
        35                  40                  45

<210> SEQ ID NO 85
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 85

-continued

Leu Ala Glu Ala Lys Glu Ala Ala Ile Ala Glu Leu Asp Ser Tyr Gly
1 5 10 15

Val Gly Ala Gly Asp Ile Lys Asp Ile Gln Asp Ala Leu Leu Val Glu
20 25 30

Ile Val Gln Leu Leu Lys Gln Ala Ile Leu Ala Val Leu Pro Ala
35 40 45

<210> SEQ ID NO 86
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 86

Leu Ala Glu Ala Lys Glu Ala Ala Ile Ala Glu Leu Asp Ser Lys Gly
1 5 10 15

Val Gly Ala Gly Asp Ile Lys Asp Ile Glu Asp Ala Leu Leu Val Glu
20 25 30

Ile Val Gln Leu Leu Lys Gln Ala Ile Leu Ala Val Leu Pro Ala
35 40 45

<210> SEQ ID NO 87
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 87

Leu Ala Glu Ala Lys Glu Ala Ala Ile Ala Glu Leu Asp Ser Tyr Gly
1 5 10 15

Val Gly Ala Val Glu Ile Lys Gln Ile Glu Glu Ala Leu Leu Val Glu
20 25 30

Ile Val Gln Leu Leu Lys Gln Ala Ile Leu Ala Val Leu Pro Ala
35 40 45

<210> SEQ ID NO 88
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 88

Leu Ala Glu Ala Lys Glu Ala Ala Ile Ala Glu Leu Asp Ser Tyr Gly
1 5 10 15

Val Gly Ala Ala Glu Ile Lys Arg Ile Glu Ala Ala Glu Leu Val Glu
20 25 30

Ile Val Gln Leu Leu Lys Gln Ala Ile Leu Ala Val Leu Pro Ala
35 40 45

<210> SEQ ID NO 89
<211> LENGTH: 47
<212> TYPE: PRT
<213> ORGANISM: Artificial Sequence
<220> FEATURE:
<223> OTHER INFORMATION: Engineered IL-6 binding Y variant

<400> SEQUENCE: 89

Leu Ala Glu Ala Lys Glu Ala Ala Ile Ala Glu Leu Asp Ser Tyr Gly
1 5 10 15

```
Val Gly Ala Gly Asp Ile Lys Asp Ile Glu Asp Ala Leu Leu Val Glu
            20                  25                  30

Ile Val Gln Leu Leu Lys Gln Ala Ile Leu Ala Val Leu Pro Ala
        35                  40                  45


<210> SEQ ID NO 90
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 90

Leu Ala Glu Ala Lys Glu Ala Ala Ile Ala Glu Leu Asp Ser Lys Gly
1               5                   10                  15

Val Gly Ala Tyr Gln Lys Ser Phe Ile Glu Leu Ala Lys Ser Val Glu
            20                  25                  30

His Val Glu Leu Leu Lys Glu Ala Ile Leu Ala Asp Leu Pro
        35                  40                  45


<210> SEQ ID NO 91
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 91

Leu Ala Glu Ala Lys Glu Ala Ala Leu Ala Glu Leu Asp Ser Lys Gly
1               5                   10                  15

Ile Gly Glu Arg Gln Ile Lys Trp Ile Glu Asn Ala Trp Ser Val Glu
            20                  25                  30

Val Val Glu Trp Leu Lys Glu Gln Ile Leu Lys Glu Leu Pro
        35                  40                  45


<210> SEQ ID NO 92
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 92

Leu Ala Glu Ala Lys Glu Ala Ala Leu Ala Glu Leu Asp Ser Ala Gly
1               5                   10                  15

Val Asn Glu Arg Glu Lys Lys Trp Ile Glu Asp Ala Gln His Val Glu
            20                  25                  30

Val Val Glu Trp Leu Lys Glu Arg Ile Leu Lys Ser Leu Pro
        35                  40                  45


<210> SEQ ID NO 93
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 93

Leu Ala Glu Ala Lys Glu Ala Ala Leu Ala Glu Leu Asp Ser Lys Gly
1               5                   10                  15

Ile Asp Ala Arg Phe Lys Glu Trp Ile Glu Asn Ala Trp Ser Val Glu
            20                  25                  30
```

```
Thr Val Glu Trp Leu Lys Glu Asn Ile Leu Lys Ala Leu Pro
        35                  40                  45


<210> SEQ ID NO 94
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 94

Leu Ala Glu Ala Lys Glu Ala Ala Ile Ala Glu Leu Asp Ser Tyr Gly
1               5                   10                  15

Ile Asn Asp His Tyr Lys Lys Ile Ile Glu Arg Ala Trp Arg Val Glu
            20                  25                  30

Gln Val Glu Trp Ala Lys Glu Ala Ile Leu Lys Asp Leu Pro
        35                  40                  45


<210> SEQ ID NO 95
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 95

Leu Ala Glu Ala Lys Glu Ala Ala Ile Ala Glu Leu Asp Ser Lys Gly
1               5                   10                  15

Ile Asp Glu Arg Lys Ile Ser Trp Ile Glu Arg Ala Gly His Val Glu
            20                  25                  30

Val Val Glu Trp Leu Lys Glu Arg Ile Leu Ala Gln Leu Pro
        35                  40                  45


<210> SEQ ID NO 96
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 96

Leu Ala Glu Ala Lys Glu Ala Ala Ile Ala Glu Leu Asp Ser Tyr Gly
1               5                   10                  15

Val Lys Ala Leu Val Ile Glu Ile Ile Glu Ser Ala His Ser Val Glu
            20                  25                  30

Glu Val Glu Gln Val Lys Glu Phe Ile Leu Ala Lys Leu Pro
        35                  40                  45


<210> SEQ ID NO 97
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 97

Leu Ala Glu Ala Lys Glu Ala Ala Ile Ala Glu Leu Asp Ser Tyr Gly
1               5                   10                  15

Ile Lys Ala Ser Leu Lys Glu Ile Ile Glu His Ala Ser Asp Val Glu
            20                  25                  30

Glu Val Glu Lys Ile Lys Glu Arg Ile Leu Ala Lys Leu Pro
        35                  40                  45
```

<210> SEQ ID NO 98
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 98

Leu Ala Glu Ala Lys Glu Ala Ala Leu Ala Glu Leu Asp Ser Tyr Gly
1 5 10 15

Val Thr Asp Val Arg Lys Ser Trp Ile Glu Lys Ala Gln Arg Val Glu
20 25 30

Val Val Glu Trp Leu Lys Glu Arg Ile Leu Ala Glu Leu Pro
35 40 45

<210> SEQ ID NO 99
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 99

Leu Ala Glu Ala Lys Glu Ala Ala Leu Ala Glu Leu Asp Ser Lys Gly
1 5 10 15

Val Ala Ala Phe Gln Ile Ser Trp Ile Glu Lys Ala Ser Ser Val Glu
20 25 30

Val Val Glu Trp Leu Lys Glu Ala Ile Leu Ala Glu Leu Pro
35 40 45

<210> SEQ ID NO 100
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 100

Leu Ala Glu Ala Lys Glu Ala Ala Leu Ala Glu Leu Asp Ser Lys Gly
1 5 10 15

Val Val Glu Val Gln Lys Glu Trp Ile Glu Arg Ala His Ser Val Glu
20 25 30

Val Val Glu Trp Leu Lys Glu Arg Ile Leu Ala Gln Leu Pro
35 40 45

<210> SEQ ID NO 101
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 101

Leu Ala Glu Ala Lys Glu Ala Ala Ile Ala Glu Leu Asp Ser Tyr Gly
1 5 10 15

Val Asp Ala Arg Phe Ile Lys Trp Ile Glu Thr Ala His Gln Val Glu
20 25 30

Val Val Glu Tyr Phe Lys Glu Arg Ile Leu Ala Asp Leu Pro
35 40 45

<210> SEQ ID NO 102
<211> LENGTH: 46

<212> TYPE: PRT
<213> ORGANISM: Artificial Sequence
<220> FEATURE:
<223> OTHER INFORMATION: Engineered insulin binding Y variant

<400> SEQUENCE: 102

```
Leu Ala Glu Ala Lys Glu Ala Ala Ile Ala Glu Leu Asp Ser Tyr Gly
1               5                   10                  15

Val Ser Glu Gly Phe Ile Lys Trp Ile Glu Gln Ala Ser Tyr Val Glu
            20                  25                  30

Val Val Glu Trp Leu Lys Glu Arg Ile Leu Lys Asp Leu Pro
        35                  40                  45
```

<210> SEQ ID NO 103
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 103

```
Leu Ala Glu Ala Lys Glu Ala Ala Leu Ala Glu Leu Asp Ser Lys Gly
1               5                   10                  15

Val His Glu Arg Phe Ile Glu Trp Ile Glu Gly Ala His Ser Val Glu
            20                  25                  30

Val Val Glu Trp Leu Lys Glu Gln Ile Leu Ala Ala Leu Pro
        35                  40                  45
```

<210> SEQ ID NO 104
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 104

```
Leu Ala Glu Ala Lys Glu Ala Ala Leu Ala Glu Leu Asp Ser Ala Gly
1               5                   10                  15

Val Gly Ala Gly Trp Lys Ser Leu Ile Glu Gly Ala Glu His Val Glu
            20                  25                  30

Thr Val Glu Trp Phe Lys Glu Arg Ile Leu Lys Asp Leu Pro
        35                  40                  45
```

<210> SEQ ID NO 105
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 105

```
Leu Ala Glu Ala Lys Glu Ala Ala Ile Ala Glu Leu Asp Ser Ala Gly
1               5                   10                  15

Val Thr Asp Arg Lys Ile Ser Trp Ile Glu Glu Ala Ser Ser Val Glu
            20                  25                  30

Val Val Glu Trp Leu Lys Glu Arg Ile Leu Ala Asp Leu Pro
        35                  40                  45
```

<210> SEQ ID NO 106
<211> LENGTH: 46
<212> TYPE: PRT
<213> ORGANISM: Artificial Sequence
<220> FEATURE:

<223> OTHER INFORMATION: Engineered insulin binding Y variant

<400> SEQUENCE: 106

Leu Ala Glu Ala Lys Glu Ala Ala Asn Ala Glu Leu Asp Ser Lys Gly
1 5 10 15

Val Gly Ala Tyr Gln Lys Ser Phe Ile Glu Leu Ala Lys Ser Val Glu
20 25 30

His Val Glu Leu Leu Lys Glu Ala Ile Leu Ala Asp Leu Pro
35 40 45

<210> SEQ ID NO 107
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 107

Leu Ala Glu Ala Lys Glu Ala Ala Ile Ala Glu Leu Asp Ser Tyr Gly
1 5 10 15

Val Glu Glu Lys Trp Ile Lys Val Ile Glu Gly Ala Trp Ser Val Glu
20 25 30

Val Val Glu Trp Phe Lys Glu Arg Ile Leu Lys Asp Leu Pro
35 40 45

<210> SEQ ID NO 108
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 108

Leu Ala Glu Ala Lys Glu Ala Ala Ile Ala Glu Leu Asp Ser Ala Gly
1 5 10 15

Val Gln Ala Lys Phe Ile Lys Trp Ile Glu Lys Ala Glu His Val Glu
20 25 30

Thr Val Glu Trp Leu Lys Glu Arg Ile Leu Lys Asp Leu Pro
35 40 45

<210> SEQ ID NO 109
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 109

Leu Ala Glu Ala Lys Glu Ala Ala Ile Ala Glu Leu Asp Ser Ala Gly
1 5 10 15

Ile Tyr Asp Gly Phe Lys Glu Trp Ile Glu Gly Ala Phe His Val Glu
20 25 30

Val Val Glu Tyr Leu Lys Glu Arg Ile Leu Ala Asp Leu Pro
35 40 45

<210> SEQ ID NO 110
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 110

Leu Ala Glu Ala Lys Glu Ala Ala Ile Ala Glu Leu Lys Ser Lys Gly
1 5 10 15

Val Gly Ala Tyr Gln Lys Ser Phe Ile Glu Leu Ala Lys Ser Val Glu
20 25 30

His Val Glu Leu Leu Lys Glu Ala Ile Leu Ala Asp Leu Pro
35 40 45

<210> SEQ ID NO 111
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 111

Leu Ala Glu Ala Lys Glu Ala Ala Ile Ala Glu Leu Asp Ser Tyr Gly
1 5 10 15

Val Gly Ala Tyr Gln Lys Ser Phe Ile Glu Leu Ala Lys Ser Val Glu
20 25 30

His Val Glu Leu Leu Lys Glu Ala Ile Leu Ala Asp Leu Pro
35 40 45

<210> SEQ ID NO 112
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 112

Leu Ala Glu Ala Lys Glu Ala Ala Ile Ala Glu Leu Asp Ser Lys Gly
1 5 10 15

Ile Gly Ala Tyr Gln Lys Ser Phe Ile Glu Leu Ala Lys Ser Val Glu
20 25 30

His Val Glu Leu Leu Lys Glu Ala Ile Leu Ala Asp Leu Pro
35 40 45

<210> SEQ ID NO 113
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 113

Leu Ala Glu Ala Lys Glu Ala Ala Ile Ala Glu Leu Asp Ser Lys Gly
1 5 10 15

Val Ser Ala Tyr Gln Lys Ser Phe Ile Glu Leu Ala Lys Ser Val Glu
20 25 30

His Val Glu Leu Leu Lys Glu Ala Ile Leu Ala Asp Leu Pro
35 40 45

<210> SEQ ID NO 114
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 114

Leu Ala Glu Ala Lys Glu Ala Ala Ile Ala Glu Leu Asp Ser Lys Gly
1 5 10 15

Val Gly Glu Tyr Gln Lys Ser Phe Ile Glu Leu Ala Lys Ser Val Glu
20 25 30

His Val Glu Leu Leu Lys Glu Ala Ile Leu Ala Asp Leu Pro
35 40 45

<210> SEQ ID NO 115
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 115

Leu Ala Glu Ala Lys Glu Ala Ala Ile Ala Glu Leu Asp Ser Lys Gly
1 5 10 15

Val Gly Ala Tyr Gln Ile Ser Phe Ile Glu Leu Ala Lys Ser Val Glu
20 25 30

His Val Glu Leu Leu Lys Glu Ala Ile Leu Ala Asp Leu Pro
35 40 45

<210> SEQ ID NO 116
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 116

Leu Ala Glu Ala Lys Glu Ala Ala Ile Ala Glu Leu Asp Ser Lys Gly
1 5 10 15

Val Gly Ala Tyr Gln Lys Lys Phe Ile Glu Leu Ala Lys Ser Val Glu
20 25 30

His Val Glu Leu Leu Lys Glu Ala Ile Leu Ala Asp Leu Pro
35 40 45

<210> SEQ ID NO 117
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 117

Leu Ala Glu Ala Lys Glu Ala Ala Ile Ala Glu Leu Asp Ser Lys Gly
1 5 10 15

Val Gly Ala Tyr Gln Ile Lys Phe Ile Glu Leu Ala Lys Ser Val Glu
20 25 30

His Val Glu Leu Leu Lys Glu Ala Ile Leu Ala Asp Leu Pro
35 40 45

<210> SEQ ID NO 118
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 118

Leu Ala Glu Ala Lys Glu Ala Ala Ile Ala Glu Leu Asp Ser Lys Gly
1 5 10 15

Val Gly Ala Tyr Gln Lys Ser Phe Ile Gln Leu Ala Lys Ser Val Glu
20 25 30

```
His Val Glu Leu Leu Lys Glu Ala Ile Leu Ala Asp Leu Pro
        35                  40                  45


<210> SEQ ID NO 119
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 119

Leu Ala Glu Ala Lys Glu Ala Ala Ile Ala Glu Leu Asp Ser Lys Gly
1               5                   10                  15

Val Gly Ala Tyr Gln Lys Ser Phe Ile Glu Leu Gly Lys Ser Val Glu
            20                  25                  30

His Val Glu Leu Leu Lys Glu Ala Ile Leu Ala Asp Leu Pro
        35                  40                  45


<210> SEQ ID NO 120
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 120

Leu Ala Glu Ala Lys Glu Ala Ala Ile Ala Glu Leu Asp Ser Lys Gly
1               5                   10                  15

Val Gly Ala Tyr Gln Lys Ser Phe Ile Glu Leu Ala Lys Ser Val Gln
            20                  25                  30

His Val Glu Leu Leu Lys Glu Ala Ile Leu Ala Asp Leu Pro
        35                  40                  45


<210> SEQ ID NO 121
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 121

Leu Ala Glu Ala Lys Glu Ala Ala Ile Ala Glu Leu Asp Ser Lys Gly
1               5                   10                  15

Val Gly Ala Tyr Gln Lys Ser Phe Ile Glu Leu Ala Lys Ser Val Glu
            20                  25                  30

His Val Gln Leu Leu Lys Glu Ala Ile Leu Ala Asp Leu Pro
        35                  40                  45


<210> SEQ ID NO 122
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 122

Leu Ala Glu Ala Lys Glu Ala Ala Ile Ala Glu Leu Asp Ser Lys Gly
1               5                   10                  15

Val Gly Ala Tyr Gln Lys Ser Phe Ile Glu Leu Ala Lys Ser Val Glu
            20                  25                  30

His Val Glu Leu Leu Lys Gln Ala Ile Leu Ala Asp Leu Pro
        35                  40                  45
```

<210> SEQ ID NO 123
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 123

```
Leu Ala Glu Ala Lys Glu Ala Ala Ile Ala Glu Leu Asp Ser Lys Gly
1               5                   10                  15

Val Gly Ala Tyr Gln Lys Ser Phe Ile Glu Leu Ala Lys Ser Val Glu
            20                  25                  30

His Val Glu Leu Leu Lys Glu Ala Ile Leu Lys Asp Leu Pro
        35                  40                  45
```

<210> SEQ ID NO 124
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 124

```
Leu Ala Glu Ala Lys Glu Ala Ala Ile Ala Glu Leu Asp Ser Lys Gly
1               5                   10                  15

Val Gly Ala Tyr Gln Lys Lys Phe Ile Glu Leu Ala Lys Ser Val Glu
            20                  25                  30

His Val Gln Leu Leu Lys Gln Ala Ile Leu Ala Asp Leu Pro
        35                  40                  45
```

<210> SEQ ID NO 125
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 125

```
Leu Ala Glu Ala Lys Glu Ala Ala Ile Ala Glu Leu Asp Ser Lys Gly
1               5                   10                  15

Val Gly Ala Tyr Gln Ile Lys Phe Ile Glu Leu Ala Lys Ser Val Glu
            20                  25                  30

His Val Gln Leu Leu Lys Gln Ala Ile Leu Ala Asp Leu Pro
        35                  40                  45
```

<210> SEQ ID NO 126
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 126

```
Leu Ala Glu Ala Lys Glu Ala Ala Ile Ala Glu Leu Asp Ser Lys Gly
1               5                   10                  15

Val Gly Ala Tyr Gln Ile Lys Phe Ile Glu Leu Ala Lys Ser Val Glu
            20                  25                  30

His Val Gln Leu Leu Lys Glu Ala Ile Leu Lys Asp Leu Pro
        35                  40                  45
```

<210> SEQ ID NO 127

<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 127

```
Leu Ala Glu Ala Lys Glu Ala Ala Ile Ala Glu Leu Asp Ser Lys Gly
1               5                   10                  15

Val Gly Ala Tyr Gln Ile Lys Phe Ile Glu Leu Ala Lys Ser Val Glu
            20                  25                  30

His Val Gln Leu Leu Lys Gln Ala Ile Leu Lys Asp Leu Pro
        35                  40                  45
```

<210> SEQ ID NO 128
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 128

```
Leu Ala Glu Ala Lys Glu Ala Ala Ile Ala Glu Leu Asp Ser Lys Gly
1               5                   10                  15

Val Gly Ala Tyr Gln Ile Lys Phe Ile Gln Leu Ala Lys Ser Val Glu
            20                  25                  30

His Val Gln Leu Leu Lys Gln Ala Ile Leu Ala Asp Leu Pro
        35                  40                  45
```

<210> SEQ ID NO 129
<211> LENGTH: 51
<212> TYPE: PRT
<213> ORGANISM: Artificial Sequence
<220> FEATURE:
<223> OTHER INFORMATION: Engineered insulin binding Y variant

<400> SEQUENCE: 129

```
Leu Ala Glu Ala Lys Glu Ala Ala Ile Ala Glu Leu Asp Ser Lys Gly
1               5                   10                  15

Val Gly Ala Tyr Gln Ile Lys Phe Ile Gln Leu Ala Lys Ser Val Glu
            20                  25                  30

His Val Gln Leu Leu Lys Gln Ala Ile Leu Ala Asp Leu Pro Ala Ser
        35                  40                  45

Tyr Gly Ser
    50
```

<210> SEQ ID NO 130
<211> LENGTH: 49
<212> TYPE: PRT
<213> ORGANISM: Artificial Sequence
<220> FEATURE:
<223> OTHER INFORMATION: Engineered insulin binding Y variant

<400> SEQUENCE: 130

```
Leu Ala Glu Ala Lys Glu Ala Ala Ile Ala Glu Leu Asp Ser Lys Gly
1               5                   10                  15

Val Gly Ala Tyr Gln Ile Lys Phe Ile Gln Leu Ala Lys Ser Val Glu
            20                  25                  30

His Val Gln Leu Leu Lys Gln Ala Ile Leu Ala Asp Leu Pro Gly Tyr
        35                  40                  45

Ser
```

<210> SEQ ID NO 131
<211> LENGTH: 52
<212> TYPE: PRT
<213> ORGANISM: Artificial Sequence
<220> FEATURE:
<223> OTHER INFORMATION: Engineered insulin binding Y variant

<400> SEQUENCE: 131

```
Thr Ile Asp Glu Trp Leu Leu Ala Glu Ala Lys Glu Ala Ala Ile Ala
1               5                   10                  15

Glu Leu Asp Ser Lys Gly Val Gly Ala Tyr Gln Ile Lys Phe Ile Gln
            20                  25                  30

Leu Ala Lys Ser Val Glu His Val Gln Leu Leu Lys Gln Ala Ile Leu
        35                  40                  45

Ala Asp Leu Pro
    50
```

<210> SEQ ID NO 132
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 132

```
Leu Ala Glu Ala Lys Glu Ala Ala Ile Ala Glu Leu Asp Ser Lys Gly
1               5                   10                  15

Val Gly Ala Tyr Gln Ile Lys Phe Ile Gln Val Ala Lys Thr Val Glu
            20                  25                  30

Gln Val Gln Ile Leu Lys Gln Ala Ile Leu Ala Asp Leu Pro Ala
        35                  40                  45
```

<210> SEQ ID NO 133
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 133

```
Leu Ala Glu Ala Lys Glu Ala Ala Ile Ala Glu Leu Asp Ser Lys Gly
1               5                   10                  15

Val Gly Ala Arg Gln Ile Lys Trp Ile Gln Gln Ala Lys Ser Val Glu
            20                  25                  30

Val Val Gln Trp Leu Lys Gln Ala Ile Leu Ala Asp Leu Pro Ala
        35                  40                  45
```

<210> SEQ ID NO 134
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 134

```
Leu Ala Glu Ala Lys Glu Ala Ala Ile Ala Glu Leu Asp Ser Lys Gly
1               5                   10                  15

Val Gly Ala Tyr Gln Ile Lys Phe Ile Gln Val Ala His Asp Val Glu
            20                  25                  30

Glu Val Gln Ile Leu Lys Gln Ala Ile Leu Ala Asp Leu Pro Ala
        35                  40                  45
```

<210> SEQ ID NO 135
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 135

```
Leu Ala Glu Ala Lys Glu Ala Ala Ile Ala Glu Leu Asp Ser Lys Gly
1               5                   10                  15

Val Gly Ala Tyr Gln Ile Lys Phe Ile Gln Ile Ala His Thr Val Glu
            20                  25                  30

Glu Val Gln Leu Met Lys Gln Ala Ile Leu Ala Asp Leu Pro Ala
        35                  40                  45
```

<210> SEQ ID NO 136
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 136

```
Leu Ala Glu Ala Lys Glu Ala Ala Ile Ala Glu Leu Asp Ser Lys Gly
1               5                   10                  15

Val Gly Ala Lys Tyr Ile Lys Met Ile Gln Met Ala Lys His Val Glu
            20                  25                  30

Thr Val Gln Tyr Met Lys Gln Ala Ile Leu Ala Ser Leu Pro Ala
        35                  40                  45
```

<210> SEQ ID NO 137
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 137

```
Leu Ala Glu Ala Lys Glu Ala Ala Ile Ala Glu Leu Asp Ser Lys Gly
1               5                   10                  15

Val Gly Ala Tyr Leu Ile Lys Phe Ile Gln Ile Ala Lys Asn Val Glu
            20                  25                  30

Ala Val Gln Phe Leu Lys Gln Ala Ile Leu Ala Asp Leu Pro Ala
        35                  40                  45
```

<210> SEQ ID NO 138
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 138

```
Leu Ala Glu Ala Lys Glu Ala Ala Ile Ala Glu Leu Asp Ser Lys Gly
1               5                   10                  15

Val Gly Ala Tyr Gln Ile Lys Phe Ile Gln Val Ala Lys Thr Val Glu
            20                  25                  30

Ala Val Gln Ala Ile Lys Gln Ala Ile Leu Ala Asp Leu Pro Ala
        35                  40                  45
```

<210> SEQ ID NO 139
<211> LENGTH: 47

<212> TYPE: PRT
<213> ORGANISM: Artificial Sequence
<220> FEATURE:
<223> OTHER INFORMATION: Engineered insulin binding Y variant

<400> SEQUENCE: 139

Leu Ala Glu Ala Lys Glu Ala Ala Ile Ala Glu Leu Asp Ser Lys Gly
1               5                   10                  15

Val Gly Ala Lys Glu Ile Lys Trp Ile Gln Met Ala Ser His Val Glu
            20                  25                  30

Val Val Gln Trp Leu Lys Gln Ala Ile Leu Ala Ser Leu Pro Ala
        35                  40                  45

<210> SEQ ID NO 140
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 140

Leu Ala Glu Ala Lys Glu Ala Ala Ile Ala Glu Leu Asp Ser Lys Gly
1               5                   10                  15

Val Gly Ala Lys Tyr Ile Lys Met Ile Gln His Ala His Tyr Val Glu
            20                  25                  30

Val Val Gln Trp Leu Lys Gln Ala Ile Leu Ala His Leu Pro
        35                  40                  45

<210> SEQ ID NO 141
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 141

Leu Ala Glu Ala Lys Glu Ala Ala Ile Ala Glu Leu Asp Ser Lys Gly
1               5                   10                  15

Val Gly Ala Lys Tyr Ile Lys Met Ile Gln His Ala His Tyr Val Glu
            20                  25                  30

Val Val Gln Trp Leu Lys Gln Ala Ile Leu Ala His Leu Pro Ala
        35                  40                  45

<210> SEQ ID NO 142
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 142

Leu Ala Glu Ala Lys Glu Ala Ala Ile Ala Glu Leu Asp Ser Lys Gly
1               5                   10                  15

Val Gly Ala Ala Lys Ile Lys Trp Ile Gln Asp Ala Lys Ser Val Glu
            20                  25                  30

Thr Val Gln Phe Leu Lys Gln Ala Ile Leu Ala Glu Leu Pro Ala
        35                  40                  45

<210> SEQ ID NO 143
<211> LENGTH: 47
<212> TYPE: PRT
<213> ORGANISM: Artificial Sequence
<220> FEATURE:

<223> OTHER INFORMATION: Engineered insulin binding Y variant

<400> SEQUENCE: 143

```
Leu Ala Glu Ala Lys Glu Ala Ala Ile Ala Glu Leu Asp Ser Lys Gly
1               5                   10                  15

Val Gly Ala Tyr Trp Ile Lys Ala Ile Gln Gln Ala Tyr Tyr Val Glu
            20                  25                  30

Met Val Gln Trp Phe Lys Gln Ala Ile Leu Ala His Leu Pro Ala
        35                  40                  45
```

<210> SEQ ID NO 144
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 144

```
Leu Ala Glu Ala Lys Glu Ala Ala Ile Ala Glu Leu Asp Ser Lys Gly
1               5                   10                  15

Val Gly Ala Lys Phe Ile Lys Met Ile Gln Ser Ala Lys Leu Val Glu
            20                  25                  30

Thr Val Gln Leu Leu Lys Gln Ala Ile Leu Ala Asp Leu Pro Ala
        35                  40                  45
```

<210> SEQ ID NO 145
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 145

```
Leu Ala Glu Ala Lys Glu Ala Ala Ile Ala Glu Leu Asp Ser Lys Gly
1               5                   10                  15

Val Gly Ala Lys Tyr Ile Lys Tyr Ile Gln Lys Ala Trp Thr Val Glu
            20                  25                  30

Gly Val Gln Tyr Leu Lys Gln Ala Ile Leu Ala Ser Leu Pro Ala
        35                  40                  45
```

<210> SEQ ID NO 146
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 146

```
Leu Ala Glu Ala Lys Glu Ala Ala Ile Ala Glu Leu Asp Ser Tyr Gly
1               5                   10                  15

Val Gly Ala Lys Tyr Ile Lys Met Ile Gln His Ala His Tyr Val Glu
            20                  25                  30

Val Val Gln Trp Leu Lys Gln Ala Ile Leu Ala His Leu Pro
        35                  40                  45
```

<210> SEQ ID NO 147
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 147

```
Leu Ala Glu Ala Lys Glu Ala Ala Ile Ala Glu Leu Asp Ser Lys Gly
1               5                   10                  15

Val Gly Ala Lys Tyr Ile Lys Met Ile Glu His Ala His Tyr Val Glu
            20                  25                  30

Val Val Gln Trp Leu Lys Gln Ala Ile Leu Ala His Leu Pro
        35                  40                  45


<210> SEQ ID NO 148
<211> LENGTH: 46
<212> TYPE: PRT
<213> ORGANISM: Artificial Sequence
<220> FEATURE:
<223> OTHER INFORMATION: Engineered insulin binding Y variant

<400> SEQUENCE: 148

Leu Ala Glu Ala Lys Glu Ala Ala Leu Ala Glu Leu Asp Ser Lys Gly
1               5                   10                  15

Val Gly Ala Lys Tyr Ile Lys Met Ile Gln His Ala His Tyr Val Glu
            20                  25                  30

Val Val Gln Trp Leu Lys Gln Ala Ile Leu Ala His Leu Pro
        35                  40                  45


<210> SEQ ID NO 149
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 149

Leu Ala Glu Ala Lys Glu Ala Ala Leu Ala Glu Leu Asp Ser Lys Gly
1               5                   10                  15

Val Gly Ala Ala Lys Ile Lys Trp Ile Gln Asp Ala Lys Ser Val Glu
            20                  25                  30

Thr Val Gln Phe Leu Lys Gln Ala Ile Leu Ala Glu Leu Pro Ala
        35                  40                  45


<210> SEQ ID NO 150
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 150

Leu Ala Glu Ala Lys Glu Ala Ala Ile Ala Glu Leu Asp Ser Tyr Gly
1               5                   10                  15

Val Gly Ala Ala Lys Ile Lys Trp Ile Gln Asp Ala Lys Ser Val Glu
            20                  25                  30

Thr Val Gln Phe Leu Lys Gln Ala Ile Leu Ala Glu Leu Pro Ala
        35                  40                  45


<210> SEQ ID NO 151
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 151

Leu Ala Glu Ala Lys Glu Ala Ala Ile Ala Glu Leu Asp Ser Lys Gly
1               5                   10                  15
```

Val Gly Ala Ala Lys Ile Lys Trp Ile Glu Asp Ala Lys Ser Val Glu
20 25 30

Thr Val Gln Phe Leu Lys Gln Ala Ile Leu Ala Glu Leu Pro Ala
35 40 45

<210> SEQ ID NO 152
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 152

Leu Ala Glu Ala Lys Glu Ala Ala Leu Ala Glu Leu Asp Ser Lys Gly
1 5 10 15

Val Gly Ala Tyr Gln Ile Lys Phe Ile Gln Ile Ala His Thr Val Glu
20 25 30

Glu Val Gln Leu Met Lys Gln Ala Ile Leu Ala Asp Leu Pro Ala
35 40 45

<210> SEQ ID NO 153
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 153

Leu Ala Glu Ala Lys Glu Ala Ala Ile Ala Glu Leu Asp Ser Tyr Gly
1 5 10 15

Val Gly Ala Tyr Gln Ile Lys Phe Ile Gln Ile Ala His Thr Val Glu
20 25 30

Glu Val Gln Leu Met Lys Gln Ala Ile Leu Ala Asp Leu Pro Ala
35 40 45

<210> SEQ ID NO 154
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 154

Leu Ala Glu Ala Lys Glu Ala Ala Ile Ala Glu Leu Asp Ser Lys Gly
1 5 10 15

Val Gly Ala Tyr Gln Ile Lys Phe Ile Glu Ile Ala His Thr Val Glu
20 25 30

Glu Val Gln Leu Met Lys Gln Ala Ile Leu Ala Asp Leu Pro Ala
35 40 45

<210> SEQ ID NO 155
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 155

Leu Ala Glu Ala Lys Glu Ala Ala Ile Ala Glu Leu Asp Ser Tyr Gly
1 5 10 15

Val Gly Ala Ala Lys Ile Lys Trp Ile Glu Asp Ala Lys Ser Val Glu
20 25 30

Thr Val Gln Phe Leu Lys Gln Ala Ile Leu Ala Glu Leu Pro Ala
35 40 45

<210> SEQ ID NO 156
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 156

Leu Ala Glu Ala Lys Glu Ala Ala Ile Ala Glu Leu Asp Ser Tyr Gly
1 5 10 15

Val Gly Ala Arg Gln Ile Lys Trp Ile Glu Gln Ala Lys Ser Val Glu
20 25 30

Val Val Gln Trp Leu Lys Gln Ala Ile Leu Ala Asp Leu Pro Ala
35 40 45

<210> SEQ ID NO 157
<211> LENGTH: 47
<212> TYPE: PRT
<213> ORGANISM: Artificial Sequence
<220> FEATURE:
<223> OTHER INFORMATION: Engineered insulin binding Y variant

<400> SEQUENCE: 157

Leu Ala Glu Ala Lys Glu Ala Ala Ile Ala Glu Leu Asp Ser Tyr Gly
1 5 10 15

Val Gly Ala Tyr Gln Ile Lys Phe Ile Glu Ile Ala His Thr Val Glu
20 25 30

Glu Val Gln Leu Met Lys Gln Ala Ile Leu Ala Asp Leu Pro Ala
35 40 45

<210> SEQ ID NO 158
<211> LENGTH: 46
<212> TYPE: PRT
<213> ORGANISM: Streptococcus sp. G148

<400> SEQUENCE: 158

Leu Ala Glu Ala Lys Val Leu Ala Asn Arg Glu Leu Asp Lys Tyr Gly
1 5 10 15

Val Ser Asp Tyr Tyr Lys Asn Leu Ile Asn Asn Ala Lys Thr Val Glu
20 25 30

Gly Val Lys Ala Leu Ile Asp Glu Ile Leu Ala Ala Leu Pro
35 40 45

<210> SEQ ID NO 159
<211> LENGTH: 46
<212> TYPE: PRT
<213> ORGANISM: Artificial Sequence
<220> FEATURE:
<223> OTHER INFORMATION: Engineered ABD variant

<400> SEQUENCE: 159

Leu Ala Glu Ala Lys Glu Ala Ala Asn Ala Glu Leu Asp Ser Tyr Gly
1 5 10 15

Val Ser Asp Phe Tyr Lys Arg Leu Ile Asp Lys Ala Lys Thr Val Glu
20 25 30

Gly Val Glu Ala Leu Lys Asp Ala Ile Leu Ala Ala Leu Pro
35 40 45

```
<210> SEQ ID NO 160
<211> LENGTH: 58
<212> TYPE: PRT
<213> ORGANISM: Artificial Sequence
<220> FEATURE:
<223> OTHER INFORMATION: Engineered Taq binding Z variant

<400> SEQUENCE: 160

Val Asp Asn Lys Phe Asn Lys Glu Leu Gly Trp Ala Thr Trp Glu Ile
1               5                   10                  15

Phe Asn Leu Pro Asn Leu Asn Gly Val Gln Val Lys Ala Phe Ile Asp
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55


<210> SEQ ID NO 161
<211> LENGTH: 100
<212> TYPE: PRT
<213> ORGANISM: Artificial Sequence
<220> FEATURE:
<223> OTHER INFORMATION: Engineered fusion of insulin-binding variant
      and ABD variant

<400> SEQUENCE: 161

Gly Ser Ser Leu Ala Glu Ala Lys Glu Ala Ala Ile Ala Glu Leu Asp
1               5                   10                  15

Ser Lys Gly Val Gly Ala Lys Tyr Ile Lys Met Ile Gln His Ala His
            20                  25                  30

Tyr Val Glu Val Val Gln Trp Leu Lys Gln Ala Ile Leu Ala His Leu
        35                  40                  45

Pro Gly Gly Gly Gly Ser Leu Ala Glu Ala Lys Glu Ala Ala Asn Ala
    50                  55                  60

Glu Leu Asp Ser Tyr Gly Val Ser Asp Phe Tyr Lys Arg Leu Ile Asp
65                  70                  75                  80

Lys Ala Lys Thr Val Glu Gly Val Glu Ala Leu Lys Asp Ala Ile Leu
                85                  90                  95

Ala Ala Leu Pro
            100


<210> SEQ ID NO 162
<211> LENGTH: 100
<212> TYPE: PRT
<213> ORGANISM: Artificial Sequence
<220> FEATURE:
<223> OTHER INFORMATION: Engineered fusion of ABD variant and insulin-
      binding variant

<400> SEQUENCE: 162

Gly Ser Ser Leu Ala Glu Ala Lys Glu Ala Ala Asn Ala Glu Leu Asp
1               5                   10                  15

Ser Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
        35                  40                  45

Pro Gly Gly Gly Gly Ser Leu Ala Glu Ala Lys Glu Ala Ala Ile Ala
    50                  55                  60

Glu Leu Asp Ser Lys Gly Val Gly Ala Lys Tyr Ile Lys Met Ile Gln
65                  70                  75                  80
```

-continued

```
His Ala His Tyr Val Glu Val Val Gln Trp Leu Lys Gln Ala Ile Leu
                85                  90                  95

Ala His Leu Pro
            100
```

<210> SEQ ID NO 163
<211> LENGTH: 181
<212> TYPE: DNA
<213> ORGANISM: Artificial Sequence
<220> FEATURE:
<223> OTHER INFORMATION: Cloning oligo for library #1
<220> FEATURE:
<221> NAME/KEY: variation
<222> LOCATION: (42)..(44)
<223> OTHER INFORMATION: Codon encoding any amino acid
<220> FEATURE:
<221> NAME/KEY: misc_feature
<222> LOCATION: (42)..(44)
<223> OTHER INFORMATION: n is a, c, g, or t
<220> FEATURE:
<221> NAME/KEY: variation
<222> LOCATION: (60)..(62)
<223> OTHER INFORMATION: Codon encoding any amino acid
<220> FEATURE:
<221> NAME/KEY: misc_feature
<222> LOCATION: (60)..(62)
<223> OTHER INFORMATION: n is a, c, g, or t
<220> FEATURE:
<221> NAME/KEY: variation
<222> LOCATION: (66)..(89)
<223> OTHER INFORMATION: Codons encoding any amino acid
<220> FEATURE:
<221> NAME/KEY: misc_feature
<222> LOCATION: (66)..(89)
<223> OTHER INFORMATION: n is a, c, g, or t
<220> FEATURE:
<221> NAME/KEY: variation
<222> LOCATION: (96)..(107)
<223> OTHER INFORMATION: Codons encoding any amino acid
<220> FEATURE:
<221> NAME/KEY: misc_feature
<222> LOCATION: (96)..(107)
<223> OTHER INFORMATION: n is a, c, g, or t
<220> FEATURE:
<221> NAME/KEY: variation
<222> LOCATION: (114)..(116)
<223> OTHER INFORMATION: Codon encoding any amino acid
<220> FEATURE:
<221> NAME/KEY: misc_feature
<222> LOCATION: (114)..(116)
<223> OTHER INFORMATION: n is a, c, g, or t
<220> FEATURE:
<221> NAME/KEY: variation
<222> LOCATION: (123)..(128)
<223> OTHER INFORMATION: Codons encoding any amino acid
<220> FEATURE:
<221> NAME/KEY: misc_feature
<222> LOCATION: (123)..(128)
<223> OTHER INFORMATION: n is a, c, g, or t
<220> FEATURE:
<221> NAME/KEY: variation
<222> LOCATION: (135)..(137)
<223> OTHER INFORMATION: Codon encoding any amino acid
<220> FEATURE:
<221> NAME/KEY: misc_feature
<222> LOCATION: (135)..(137)
<223> OTHER INFORMATION: n is a, c, g, or t
<220> FEATURE:
<221> NAME/KEY: variation
<222> LOCATION: (144)..(149)
<223> OTHER INFORMATION: Codons encoding any amino acid
<220> FEATURE:
<221> NAME/KEY: misc_feature
<222> LOCATION: (144)..(149)
<223> OTHER INFORMATION: n is a, c, g, or t

<400> SEQUENCE: 163

```
aaataaatgg atccagcctg gctgaggcga aagaagccgc gnnngccgag ctggatagcn     60

nnggtnnnnn nnnnnnnnnn nnnnnnnnna tcgagnnnnn nnnnnnngtt gagnnngttg    120

aannnnnnaa agaannnatt ctgnnnnnnc tgccggcgag cggtagcgtc gacattattt    180

a                                                                    181


<210> SEQ ID NO 164
<211> LENGTH: 117
<212> TYPE: DNA
<213> ORGANISM: Artificial Sequence
<220> FEATURE:
<223> OTHER INFORMATION: Cloning oligo for library #2
<220> FEATURE:
<221> NAME/KEY: variation
<222> LOCATION: (22)..(27)
<223> OTHER INFORMATION: Two codons each encoding any amino acid except
      C and P
<220> FEATURE:
<221> NAME/KEY: misc_feature
<222> LOCATION: (22)..(27)
<223> OTHER INFORMATION: n is a, c, g, or t
<220> FEATURE:
<221> NAME/KEY: variation
<222> LOCATION: (34)..(36)
<223> OTHER INFORMATION: Codon encoding any amino acid except C and P
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: variation
<222> LOCATION: (43)..(45)
<223> OTHER INFORMATION: Codon encoding any amino acid except C
<220> FEATURE:
<221> NAME/KEY: misc_feature
<222> LOCATION: (43)..(45)
<223> OTHER INFORMATION: n is a, c, g, or t
<220> FEATURE:
<221> NAME/KEY: variation
<222> LOCATION: (49)..(54)
<223> OTHER INFORMATION: Two codons each encoding any amino acid except
      C
<220> FEATURE:
<221> NAME/KEY: misc_feature
<222> LOCATION: (49)..(54)
<223> OTHER INFORMATION: n is a, c, g, or t
<220> FEATURE:
<221> NAME/KEY: variation
<222> LOCATION: (61)..(63)
<223> OTHER INFORMATION: Codon encoding any amino acid except C, 50% G
      and even distribution of rest
<220> FEATURE:
<221> NAME/KEY: misc_feature
<222> LOCATION: (61)..(63)
<223> OTHER INFORMATION: n is a, c, g, or t
<220> FEATURE:
<221> NAME/KEY: variation
<222> LOCATION: (70)..(75)
<223> OTHER INFORMATION: Two codons each encoding any amino acid except
      C and P
<220> FEATURE:
<221> NAME/KEY: misc_feature
<222> LOCATION: (70)..(75)
<223> OTHER INFORMATION: n is a, c, g, or t
<220> FEATURE:
<221> NAME/KEY: variation
<222> LOCATION: (82)..(84)
<223> OTHER INFORMATION: Codon encoding any amino acid except C, 50% A
      and even distribution of rest
<220> FEATURE:
<221> NAME/KEY: misc_feature
<222> LOCATION: (82)..(84)
<223> OTHER INFORMATION: n is a, c, g, or t
<220> FEATURE:
<221> NAME/KEY: variation
```

<222> LOCATION: (94)..(96)
<223> OTHER INFORMATION: Codon encoding any amino acid except C and P
<220> FEATURE:
<221> NAME/KEY: misc_feature
<222> LOCATION: (94)..(96)
<223> OTHER INFORMATION: n is a, c, g, or t

<400> SEQUENCE: 164
gatagcaaag gtgttggtgc annnnnnatt aaannnattc agnnngcann nnnngttgag 60
nnngttcaan nnnnnaaaca gnnnattctg gcgnnnctgc cggcgagcgg tagcgtc 117

<210> SEQ ID NO 165
<211> LENGTH: 36
<212> TYPE: PRT
<213> ORGANISM: Artificial Sequence
<220> FEATURE:
<223> OTHER INFORMATION: Short scaffold sequence
<220> FEATURE:
<221> NAME/KEY: VARIANT
<222> LOCATION: (1)..(1)
<223> OTHER INFORMATION: I or L
<220> FEATURE:
<221> NAME/KEY: VARIANT
<222> LOCATION: (6)..(6)
<223> OTHER INFORMATION: C or S
<220> FEATURE:
<221> NAME/KEY: VARIANT
<222> LOCATION: (7)..(7)
<223> OTHER INFORMATION: K or Y
<220> FEATURE:
<221> NAME/KEY: VARIANT
<222> LOCATION: (12)..(13)
<223> OTHER INFORMATION: Any amino acid
<220> FEATURE:
<221> NAME/KEY: VARIANT
<222> LOCATION: (16)..(16)
<223> OTHER INFORMATION: Any amino acid
<220> FEATURE:
<221> NAME/KEY: VARIANT
<222> LOCATION: (18)..(18)
<223> OTHER INFORMATION: E or Q
<220> FEATURE:
<221> NAME/KEY: VARIANT
<222> LOCATION: (19)..(19)
<223> OTHER INFORMATION: Any amino acid
<220> FEATURE:
<221> NAME/KEY: VARIANT
<222> LOCATION: (21)..(22)
<223> OTHER INFORMATION: Any amino acid
<220> FEATURE:
<221> NAME/KEY: VARIANT
<222> LOCATION: (25)..(25)
<223> OTHER INFORMATION: Any amino acid
<220> FEATURE:
<221> NAME/KEY: VARIANT
<222> LOCATION: (28)..(29)
<223> OTHER INFORMATION: Any amino acid
<220> FEATURE:
<221> NAME/KEY: VARIANT
<222> LOCATION: (32)..(32)
<223> OTHER INFORMATION: Any amino acid
<220> FEATURE:
<221> NAME/KEY: VARIANT
<222> LOCATION: (36)..(36)
<223> OTHER INFORMATION: Any amino acid

<400> SEQUENCE: 165

Xaa Ala Glu Leu Asp Xaa Xaa Gly Val Gly Ala Xaa Xaa Ile Lys Xaa
1 5 10 15

Ile Xaa Xaa Ala Xaa Xaa Val Glu Xaa Val Gln Xaa Xaa Lys Gln Xaa
20 25 30

Ile Leu Ala Xaa
35

<210> SEQ ID NO 166
<211> LENGTH: 46
<212> TYPE: PRT
<213> ORGANISM: Artificial Sequence
<220> FEATURE:
<223> OTHER INFORMATION: Long scaffold sequence
<220> FEATURE:
<221> NAME/KEY: VARIANT
<222> LOCATION: (9)..(9)
<223> OTHER INFORMATION: I or L
<220> FEATURE:
<221> NAME/KEY: VARIANT
<222> LOCATION: (14)..(14)
<223> OTHER INFORMATION: C or S
<220> FEATURE:
<221> NAME/KEY: VARIANT
<222> LOCATION: (15)..(15)
<223> OTHER INFORMATION: K or Y
<220> FEATURE:
<221> NAME/KEY: VARIANT
<222> LOCATION: (20)..(21)
<223> OTHER INFORMATION: Any amino acid
<220> FEATURE:
<221> NAME/KEY: VARIANT
<222> LOCATION: (24)..(24)
<223> OTHER INFORMATION: Any amino acid
<220> FEATURE:
<221> NAME/KEY: VARIANT
<222> LOCATION: (26)..(26)
<223> OTHER INFORMATION: E or Q
<220> FEATURE:
<221> NAME/KEY: VARIANT
<222> LOCATION: (27)..(27)
<223> OTHER INFORMATION: Any amino acid
<220> FEATURE:
<221> NAME/KEY: VARIANT
<222> LOCATION: (29)..(30)
<223> OTHER INFORMATION: Any amino acid
<220> FEATURE:
<221> NAME/KEY: VARIANT
<222> LOCATION: (33)..(33)
<223> OTHER INFORMATION: Any amino acid
<220> FEATURE:
<221> NAME/KEY: VARIANT
<222> LOCATION: (36)..(37)
<223> OTHER INFORMATION: Any amino acid
<220> FEATURE:
<221> NAME/KEY: VARIANT
<222> LOCATION: (40)..(40)
<223> OTHER INFORMATION: Any amino acid
<220> FEATURE:
<221> NAME/KEY: VARIANT
<222> LOCATION: (44)..(44)
<223> OTHER INFORMATION: Any amino acid

<400> SEQUENCE: 166

```
Leu Ala Glu Ala Lys Glu Ala Ala Xaa Ala Glu Leu Asp Xaa Xaa Gly
1               5                   10                  15

Val Gly Ala Xaa Xaa Ile Lys Xaa Ile Xaa Xaa Ala Xaa Xaa Val Glu
            20                  25                  30

Xaa Val Gln Xaa Xaa Lys Gln Xaa Ile Leu Ala Xaa Leu Pro
        35                  40                  45
```

<210> SEQ ID NO 167
<211> LENGTH: 65
<212> TYPE: PRT
<213> ORGANISM: Artificial Sequence
<220> FEATURE:
<223> OTHER INFORMATION: Engineered, His6-tagged Y variant
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid

<400> SEQUENCE: 167

Met Gly Ser Ser His His His His His His Gly Ser Ser Leu Ala Glu
1 5 10 15

Ala Lys Glu Ala Ala Xaa Ala Glu Leu Asp Xaa Xaa Gly Val Gly Ala
20 25 30

Xaa Xaa Ile Lys Xaa Ile Xaa Xaa Ala Xaa Xaa Val Glu Xaa Val Gln
35 40 45

Xaa Xaa Lys Gln Xaa Ile Leu Ala Xaa Leu Pro Ala Ser Gly Ser Val
50 55 60

Asp
65

<210> SEQ ID NO 168
<211> LENGTH: 59
<212> TYPE: PRT
<213> ORGANISM: Artificial Sequence
<220> FEATURE:
<223> OTHER INFORMATION: Engineered, His6-tagged Y variant
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid

<400> SEQUENCE: 168

```
Met Gly Ser Ser His His His His His His Gly Ser Ser Leu Ala Glu
1               5                   10                  15

Ala Lys Glu Ala Ala Xaa Ala Glu Leu Asp Xaa Xaa Gly Val Gly Ala
            20                  25                  30

Xaa Xaa Ile Lys Xaa Ile Xaa Xaa Ala Xaa Xaa Val Glu Xaa Val Gln
        35                  40                  45

Xaa Xaa Lys Gln Xaa Ile Leu Ala Xaa Leu Pro
    50                  55
```

<210> SEQ ID NO 169
<211> LENGTH: 64
<212> TYPE: PRT
<213> ORGANISM: Artificial Sequence
<220> FEATURE:
<223> OTHER INFORMATION: Engineered, His6-tagged Y variant
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (53)..(53)

```
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid

<400> SEQUENCE: 169

Met Gly Ser Ser His His His His His His Gly Ser Ser Leu Ala Glu
1               5                   10                  15

Ala Lys Glu Ala Ala Xaa Ala Glu Leu Asp Xaa Xaa Gly Val Gly Ala
            20                  25                  30

Xaa Xaa Ile Lys Xaa Ile Xaa Xaa Ala Xaa Xaa Val Glu Xaa Val Gln
        35                  40                  45

Xaa Xaa Lys Gln Xaa Ile Leu Ala Xaa Leu Pro Ala Ser Tyr Gly Ser
    50                  55                  60


<210> SEQ ID NO 170
<211> LENGTH: 62
<212> TYPE: PRT
<213> ORGANISM: Artificial Sequence
<220> FEATURE:
<223> OTHER INFORMATION: Engineered, His6-tagged Y variant
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid

<400> SEQUENCE: 170

Met Gly Ser Ser His His His His His His Gly Ser Ser Leu Ala Glu
1               5                   10                  15

Ala Lys Glu Ala Ala Xaa Ala Glu Leu Asp Xaa Xaa Gly Val Gly Ala
            20                  25                  30

Xaa Xaa Ile Lys Xaa Ile Xaa Xaa Ala Xaa Xaa Val Glu Xaa Val Gln
        35                  40                  45
```

-continued

Xaa Xaa Lys Gln Xaa Ile Leu Ala Xaa Leu Pro Gly Tyr Ser
    50                  55                  60

<210> SEQ ID NO 171
<211> LENGTH: 62
<212> TYPE: PRT
<213> ORGANISM: Artificial Sequence
<220> FEATURE:
<223> OTHER INFORMATION: Engineered, His6-tagged Y variant
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid

<400> SEQUENCE: 171

Met Gly Ser Ser His His His His His His Thr Ile Asp Glu Trp Leu
1               5                   10                  15

Leu Ala Glu Ala Lys Glu Ala Ala Xaa Ala Glu Leu Asp Xaa Xaa Gly
            20                  25                  30

Val Gly Ala Xaa Xaa Ile Lys Xaa Ile Xaa Xaa Ala Xaa Xaa Val Glu
        35                  40                  45

Xaa Val Gln Xaa Xaa Lys Gln Xaa Ile Leu Ala Xaa Leu Pro
    50                  55                  60

<210> SEQ ID NO 172
<211> LENGTH: 60
<212> TYPE: PRT
<213> ORGANISM: Artificial Sequence
<220> FEATURE:
<223> OTHER INFORMATION: Engineered, His6-tagged Y variant
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (27)..(28)

<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid

<400> SEQUENCE: 172

```
Met Gly Ser Ser His His His His His His Gly Ser Ser Leu Ala Glu
1               5                   10                  15

Ala Lys Glu Ala Ala Xaa Ala Glu Leu Asp Xaa Xaa Gly Val Gly Ala
            20                  25                  30

Xaa Xaa Ile Lys Xaa Ile Xaa Xaa Ala Xaa Xaa Val Glu Xaa Val Gln
        35                  40                  45

Xaa Xaa Lys Gln Xaa Ile Leu Ala Xaa Leu Pro Ala
    50                  55                  60
```

<210> SEQ ID NO 173
<211> LENGTH: 115
<212> TYPE: PRT
<213> ORGANISM: Artificial Sequence
<220> FEATURE:
<223> OTHER INFORMATION: Engineered Y variant in fusion with Z03639
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid -continued

```
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid

<400> SEQUENCE: 173

Gly Ser Ser Leu Ala Glu Ala Lys Glu Ala Ala Xaa Ala Glu Leu Asp
1               5                   10                  15

Xaa Xaa Gly Val Gly Ala Xaa Xaa Ile Lys Xaa Ile Xaa Xaa Ala Xaa
            20                  25                  30

Xaa Val Glu Xaa Val Gln Xaa Xaa Lys Gln Xaa Ile Leu Ala Xaa Leu
        35                  40                  45

Pro Ala Ser Gly Ser Val Asp Asn Lys Phe Asn Lys Glu Leu Gly Trp
    50                  55                  60

Ala Thr Trp Glu Ile Phe Asn Leu Pro Asn Leu Asn Gly Val Gln Val
65                  70                  75                  80

Lys Ala Phe Ile Asp Ser Leu Arg Asp Asp Pro Ser Gln Ser Ala Asn
                85                  90                  95

Leu Leu Ala Glu Ala Lys Lys Leu Asn Asp Ala Gln Ala Pro Lys Tyr
            100                 105                 110

Val Pro Gly
        115
```